United States Patent
Bolotina

(10) Patent No.: US 10,390,521 B2
(45) Date of Patent: Aug. 27, 2019

(54) PARKINSONS DISEASE MODEL AND METHODS

(71) Applicant: Boston Medical Center Corporation, Boston, MA (US)

(72) Inventor: Victoria Bolotina, North Andover, MA (US)

(73) Assignee: BOSTON MEDICAL CENTER CORPORATION, Boston, MA (US)

( * ) Notice: Subject to any disclaimer, the term of this patent is extended or adjusted under 35 U.S.C. 154(b) by 0 days.

(21) Appl. No.: 15/464,047

(22) Filed: Mar. 20, 2017

(65) Prior Publication Data

US 2017/0290309 A1 Oct. 12, 2017

Related U.S. Application Data

(62) Division of application No. 14/213,359, filed on Mar. 14, 2014, now Pat. No. 9,599,605.

(60) Provisional application No. 61/792,916, filed on Mar. 15, 2013.

(51) Int. Cl.
| | |
|---|---|
| A01K 67/027 | (2006.01) |
| A61K 38/46 | (2006.01) |
| C12N 5/0793 | (2010.01) |
| C12N 9/18 | (2006.01) |
| G01N 33/50 | (2006.01) |
| C12N 9/20 | (2006.01) |
| A61K 48/00 | (2006.01) |

(52) U.S. Cl.
CPC ........ *A01K 67/0276* (2013.01); *A61K 38/465* (2013.01); *C12N 5/0619* (2013.01); *C12N 9/18* (2013.01); *C12N 9/20* (2013.01); *C12Y 301/01004* (2013.01); *G01N 33/5044* (2013.01); *G01N 33/5091* (2013.01); *A01K 2217/056* (2013.01); *A01K 2217/075* (2013.01); *A01K 2227/105* (2013.01); *A01K 2267/0318* (2013.01); *A61K 48/00* (2013.01); *C12N 2510/00* (2013.01)

(58) Field of Classification Search
None
See application file for complete search history.

(56) References Cited

U.S. PATENT DOCUMENTS 8,187,811 B2 5/2012 Eriksson et al.

OTHER PUBLICATIONS

Roger L Albin et al., "The functional anatomy of disorders of the basal ganglia.," Trends Neuroscience, vol. 18, pp. 63-64 (1995).
Shunzhong Bao et al., "Male Mice That Do Not Express Group VIA Phospholipase A2 Produce Spermatozoa with Impaired Motility and Have Greatly Reduced Fertility.," Journal of Biological Chemistry, vol. 279, No. 37, pp. 38194-38200 (2004).
Boichi Beck, et al., "Neuroaxonal Dystrophy i n Calcium-Independent Phospholipase A2B Deficiency Results from Insufficient Remodeling and Degeneration of Mitochondrial and Presynaptic Membrane," The Journal of Neuroscience, vol. 31, No. 31, pp. 11411-11420 (2011).
C. Savio Chan, et al., "Calcium Homeostasis, selective vulnerability and Parkinson's disease.," Trends in Neuroscience, vol. 32, No. 5, pp. 249-256 (2009).
Edward A. Dennis, et al., "Phospholipase A2 Enzymes: Physical Structure, Biological Function, Disease Implication, Chemical Inhibition, and Therapeutic Intervention.," Chem Rev, vol. 111, No. 10, pp. 6130-6185 (2011).
Laura A. Engel, et al., "Catalytic Function of PLA2G6 Is Impaired by Mutations Associated with Infantile Neuroaxonal Dstrophy but Not Dystonia-Parkinsonism," PLoS ONE 5(9): e12897. doi:10.1371/journal.pone.0012897 (2010).
A. Gregory et al., "Clinical and genetic delineation of neurodegeneration with brain iron accumulation.," J Med Genet, vol. 46, pp. 73-80 (2008).
A. Gregory et al., "Neurodegeneration associated with genetic defects in phopholipase A2 Symbol," Neurology, vol. 71, pp. 1402-1409 (2008).
Kai Michael Kauther, et al., "The PLA2G6 Gene in Early-Onset Parkinson's Disease," Movement Disorders, vol. 26, No. 13, pp. 2415-2437 (2011).
Chin-Song Lu, et al., "PLA3G6 mutations in PARK14-linked young-onset parkinsonism and sporadic Parkinson's disease,"Am J Med Genet Part B, vol. 159B, pp. 183-191 (2011).

(Continued)

*Primary Examiner* — Robert M Kelly
(74) *Attorney, Agent, or Firm* — Arrigo, Lee, Guttman & Mouta-Bellum LLP

(57) ABSTRACT

This application provides a novel mouse model (PLA2g6 KO$^{Ex2}$) in which genetic deletion of the N terminus of PLA2g6 results in a loss of dopaminergic (DA) neurons in substantia nigra (SN), and development of PD-like motor deficits that can be significantly improved by L-DOPA. Based in part on experimental results demonstrated with this model, this disclosure provides genetically modified animals and genetically modified animal cells that comprise a mutant allele of PLA2g6 and in which store-operated Ca$^{2+}$ entry (SOCE) is impaired and ER Ca$^{2+}$ stores are depleted. This disclosure also provides methods of screening a compound for an effect on the SOCE pathway and/or ER Ca$^{2+}$ by administering the compound to such a genetically modified animal or genetically modified animal cell. This disclosure also provides methods of treating or preventing PD-related deficit(s) in an animal by characterizing a compound as a SOCE activator using the screening methods and then administering an effective amount of the compound to an animal. This disclosure also provides methods of restoring normal store-operated Ca$^{2+}$ entry (SOCE) pathway and ER Ca$^{2+}$ in a cell, comprising introducing a caspase-3 cleavage-resistant PLA2g6 protein into the cell. This disclosure also provides methods of treating or preventing a PD-related deficit(s) in an animal, comprising administering a caspase-3 cleavage-resistant PLA2g6 protein to the animal.

13 Claims, 35 Drawing Sheets
Specification includes a Sequence Listing.

(56) References Cited

OTHER PUBLICATIONS

Ibrahim Malik, et al., "Disrupted Membrane Homeostasis and Accumulation of Ubiquitinated Proteins in a Mouse Model of Infantile Neuroaxonal Dystrophy Caused by PLA2G6 Mutations," The American Journal of Pathology, vol. 172, No. 2, pp. 406-416 (2008).

Neil V Morgan et al., "PLA2G6, encoding a phopholipase A2, is mutated in neurodegenerative disorders with high brain iron," Nat Genet., vol. 38, No. 7, pp. 752-754 (2006).

Coro Paisan-Ruiz, et al., "Early-Onset L-dopa-Responsive Parkinsonism with Pyramidal Signs Due to ATP13A2, PLA2G6, FBX07 and Spatacsin Mutations," Movement Disorders, vol. 25, No. 12, pp. 1791-1800 (2010).

Coro Paisan-Ruiz, et al., "Widespread Lewy body and tau accumulation in childhood and adult onset dystonia-parkinsonism cases with PLA2G6 mutations," Neurobiology of Aging, vol. 33, pp. 814-823 (2012).

Coro Paisan-Ruiz, et al., "Characterization of PLA2G6 as a Locus for Dystonia-Parkinsonism," Ann Neurol., vol. 65, pp. 19-23 (2009).

Susanne A. Schneider, et al., "Syndromes of Neurodegeneration with Brain Iron Accumulation (NBM an Update on Clinical Presentations, Histological and Genetic Underpinnings, and Treatment Considerations," Movement Disorders, vol. 27, No. 1, pp. 42-53 (2012).

Koei Shinzawa, et al., "Neuroaxonal Dystrophy Caused by Group VIA Phospholipase A2 Deficiency in Mice: A Model of Human Neurogenerative Disease," The Journal of Neuroscience, vol. 28, No. 9, pp. 2212-2220 (2008).

F. Sina, et al., "R632W mutation in PLA2G6 segregates with dystonia-parkinsonism in a consanguineous Iranian family," European Journal of Neurology, 16, pp. 101-104 (2009).

Mikhail Strokin, et al., "Severe disturbance in the Ca+2 signaling in astrocytes from mouse models of human infantile neuroaxonal dystrophy with mutated Pla2g6," Human Molecular Genetics, vol. 21, No. 12, pp. 2807-2814 (2012).

D. James Surmeier, et al., "Calcium, cellular aging, and selective neuronal vulnerability in Parkinson's disease," Cell Calcium, vol. 47, pp. 175-182 (2010).

D. J. Surmeier, et al., "The Role of Calcium and Mitochondrial Oxidant Stress in the Loss of Substantia Nigra Pars Compacta Dopaminergic Neurons in Parkinson's Disease," Neuroscience vol. 198, pp. 221-231 (2011).

D. James Surmeier, et al., "A Lethal Convergence of Dopamine and Calcium," Neuron vol. 62, pp. 163-164 (2009).

Hiroyuki Tomiyama, et al., "PLA3G6 variant Parkinson's disease," Journal of Human Genetics, vol. 56, pp. 401-403 (2011).

A Tonelli, et al., "Novel splice-site mutations and a large intragenic deletion in PLA2G6 associated with a severe and rapidly progressive form of infantile neuroaxonal dystrophy," Clin Genet, vol. 78, pp. 432-440 2010.

Haruka Wada, et al., "Establishment of an Improved Mouse Model for Infantile Neuroaxonal Dystrophy That shows Early Disease Onset and Bears a Point Mutation in Pla2g6," The American Journal of Pathology, vol. 175, No. 6, pp. 2257-2263 (2009).

H. Yoshino, et al., "Phenotypic spectrum of patients with PLA2G6 mutation and PARK14-linked parkinsonism," Neurology, vol. 75, pp. 1356-1361 (2010).

Zhengshan Zhao, et al., "Genetic Ablation of PLA2G6 in Mice Leads to Cerebellar Atrophy Characterized by Purkinje Cell Loss and Glial Cell Activation," PLoS ONE 6(10): e26991. doi:10.1371/journal.pone.0026991 (2011).

Alexander Zimprich, et al., "Genetics of Parkinson's disease and essential tremor," Curr. Opin. Neurol., vol. 24, pp. 318-323 (2011).

Victoria M. Bolotina, "Orai1, STIM1, and iPLA2B Determine Arterial Vasoconstriction," Arteriosclerosis, Thrombosis, and Vascular Biology, vol. 32, pp. 1066-1067 (2012).

Lu, et al. (2011) "PLA2G6 Mutations in PARK14-Linked Young-Onset Parkinsonism and Sporadic Parkinson's Disease", American Journal of Medical Genetics, Part B, 159B: 183-91.

Oslowski, et al. (2013) "New causal relationship between PLA2g6. store-operated Ca2+ entry, refilling of Ca2+ stores and ER stress in mouse embryonic fibroblasts", FASEB J., 27(Meeting Abstract Supplement): 1198.2.

Polster, et al. (2010) "Expression of PLA2G6 in human fetal development: Implications for infantile neuroaxonal dystrophy", Brain Research Bulletin, 83(6): 374-79.

Zhou et al (Jan. 12, 2016) "Impairment of PARK14-depenedent Ca2+ signaling is a novel determinant of Parkinson's disease", Nature Communications, 7:10332, pp. 1-14.

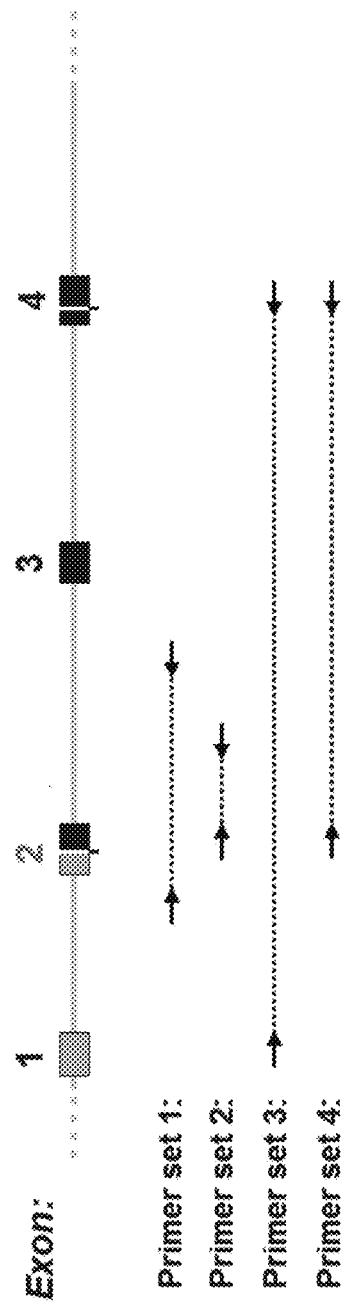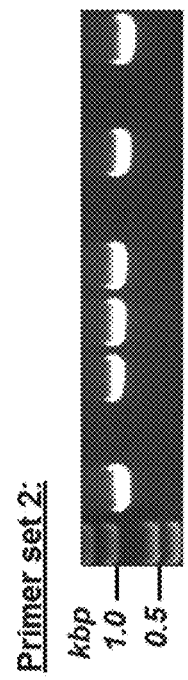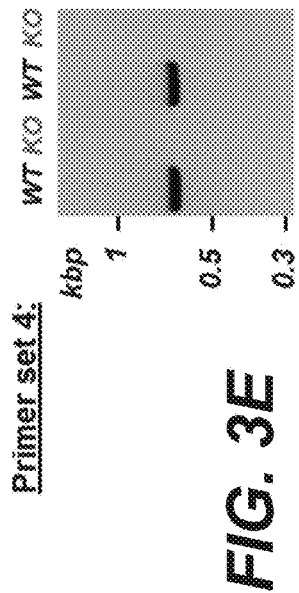
FIG. 3A
FIG. 3B
FIG. 3C
FIG. 3D
FIG. 3E

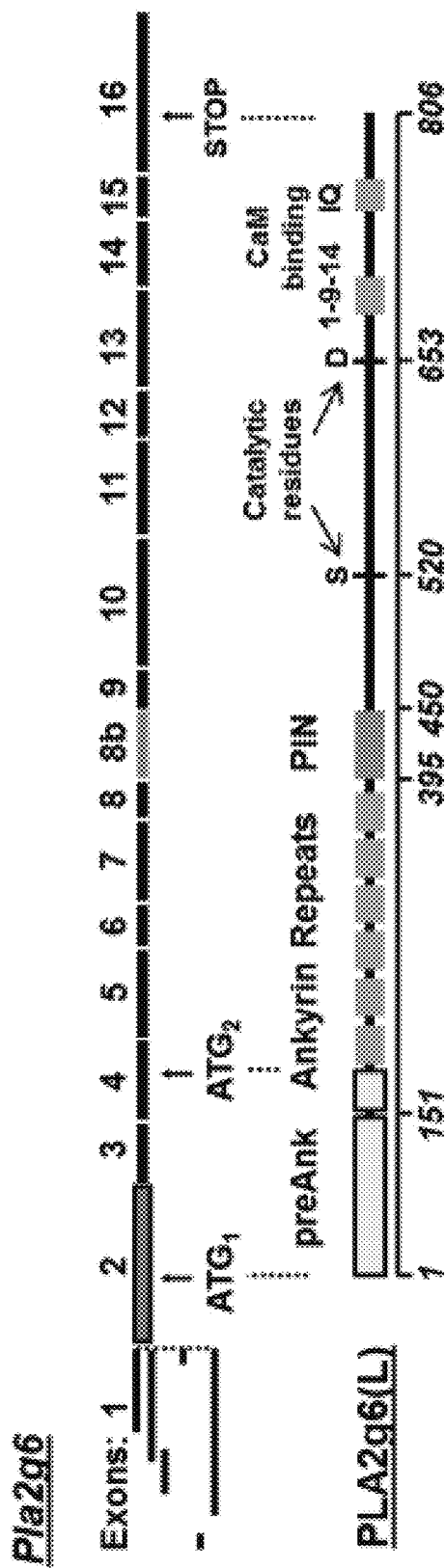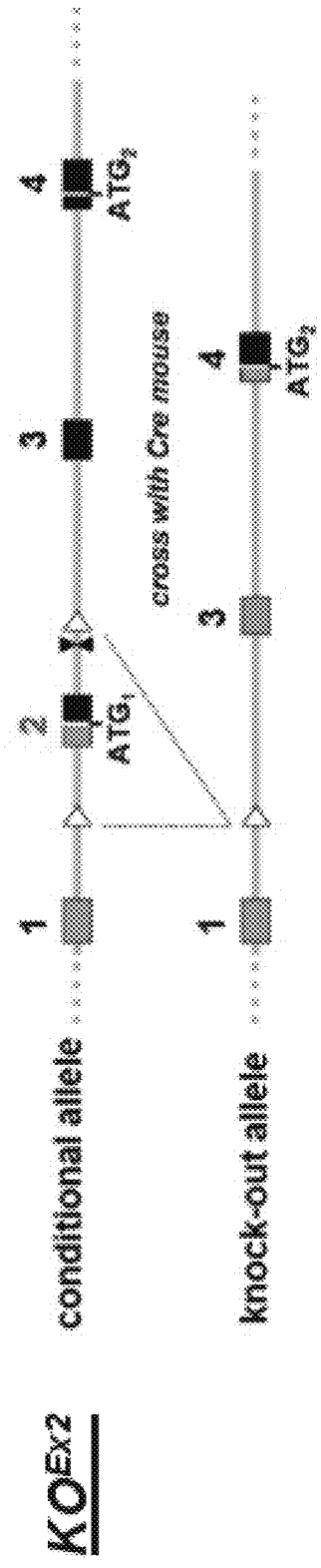
FIG. 6A
FIG. 6B

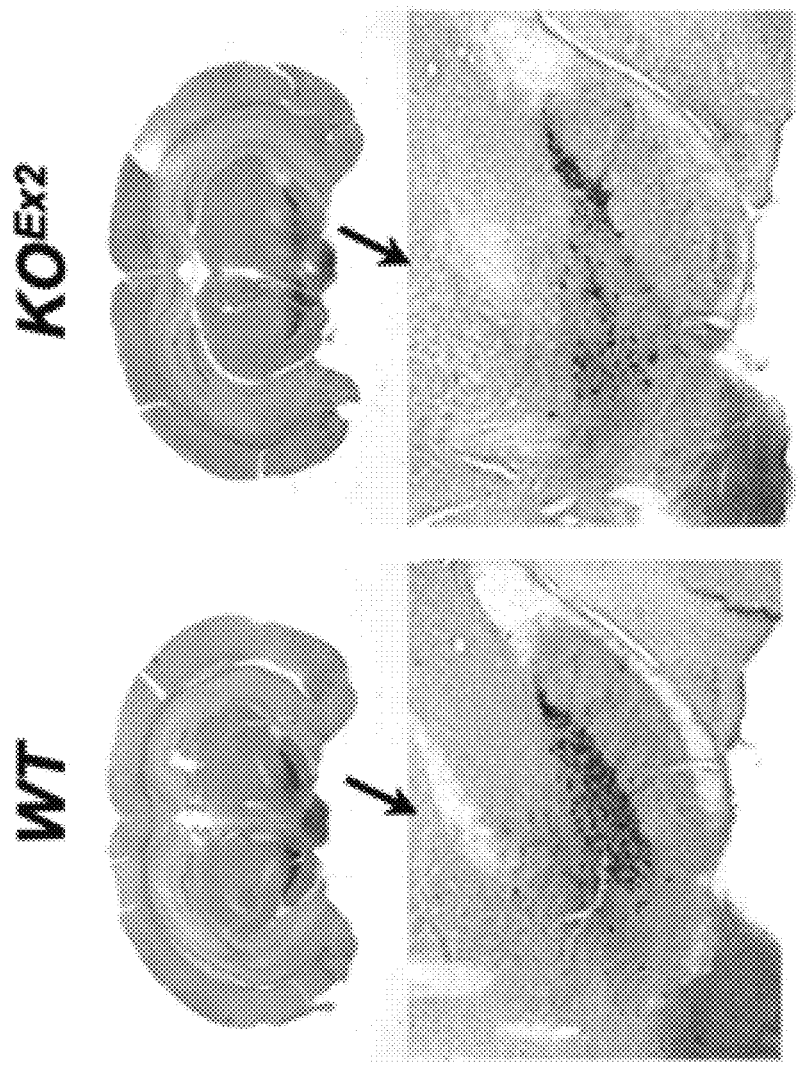

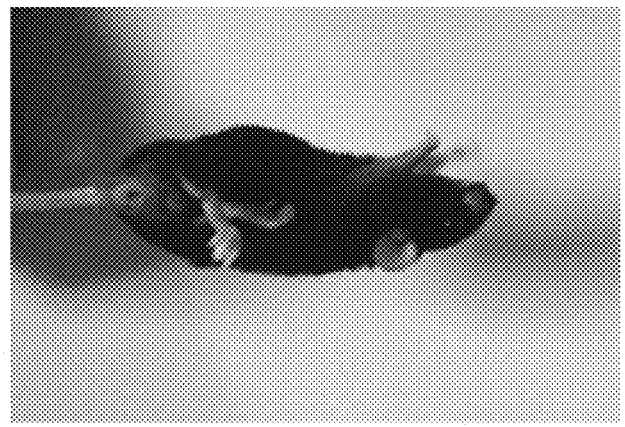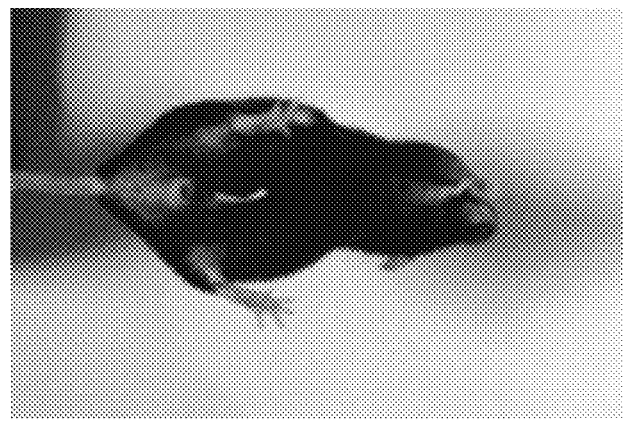
FIG. 10A

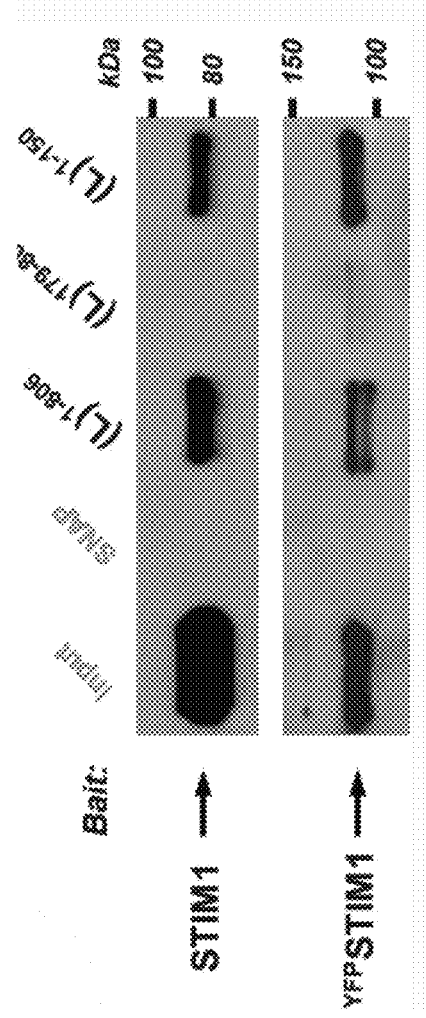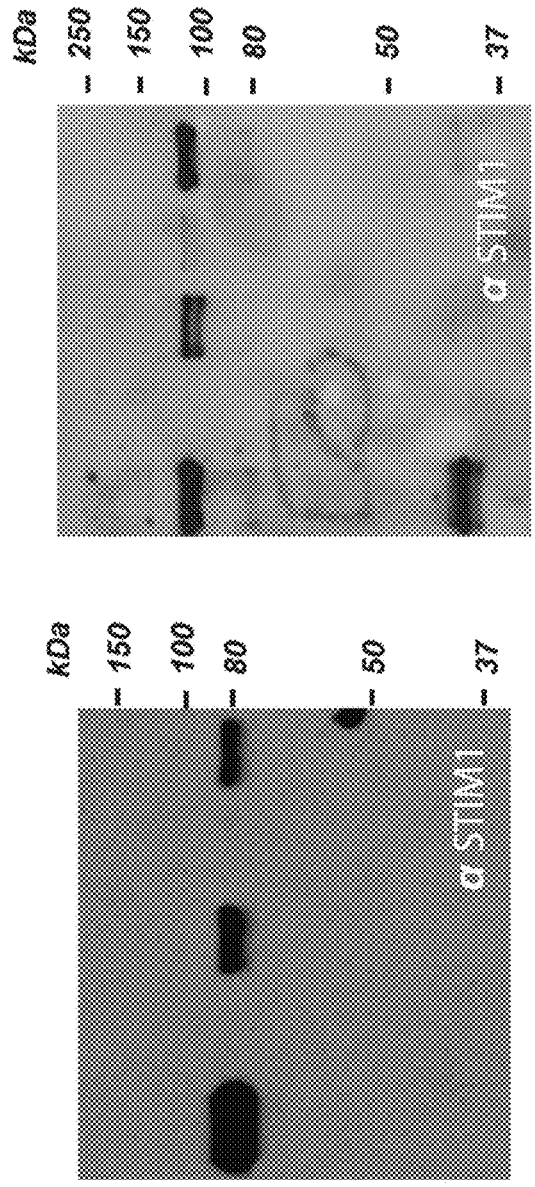
FIG. 12A
FIG. 12B
FIG. 12C

```
Human    1    MQFFGRLVNTFSGVTNLFSNPFRVKEVAVADYTSSDRVREEGQLILFQNTPNRTWDCVLV    60
Mouse    1    MQFFGRLVNT S VTNLFSNPFRVKEV++ DY SS+RVREEGQLIL QN NRTWDCVLV    60
              MQFFGRLVNTLSSVTNLFSNPFRVKEVSLTDYVSSERVREEGQLILQNVSNRTWDCVLV
                                   F72L
Human   61    NPRNSQSGFRL QLELEADALVNFHQYSSQLLPFYESSPQVLHTEVLQHLTDLIRNHPSW   120
                +PRN QSGFRL QLE EADALVNF Q+SSQL PFYESS QVLH EVLQHLTDLIRNHPSW
Mouse   61    SPRNPQSGFRL QLESEADALVNFQQFSSQLPFYESSVQVLHVEVLQHLTDLIRNHPSW   120
                                                                    KO^Ex2 ↓
Human  121    SVAHLAVELGIRECFHHSRIISCANCAENEEGCTPLHLACRKGDGEILVELVQCHTQMD   180
               +V HLAVELGIRECFHHSRIISCAN  ENEEGCTPLHLACRKGD EILVELVQCH QMD
Mouse  121    TVTHLAVELGIRECFHHSRIISCANSTENEEGCTPLHLACRKGDSEILVELVQCHAQMD   180
                  D183
Human  181    VTD YKGETVFHYAVQGDNSQVLQLLGRNAVAGLNQVNNQGLTPLHLACQLGKQEMVRLL   240
              VTD KGET FHYAVQGDN QVLQLLG+NA AGLNQVNNQGLTPLHLAC++GKQEMVRLL
Mouse  181    VTDNKGETAFHYAVQGDNPQVLQLLGKNASAGLNQVNNQGLTPLHLACKMGKQEMVRLL   240

Human  241    LCNARCNIMGPNGYPIHSAMKFSQKGCAEMIISMDSSQIHSKDPRYGASPLHWAKNAEMA   300
              LCNARCNIMGP G+PIH+AMKFSQKGCAEMIISMDS+QIHSKDPRYGASPLHWAKNAEMA
Mouse  241    LCNARCNIMGPGGFPIHTAMKFSQKGCAEMIISMDSNQIHSKDPRYGASPLHWAKNAEMA   300
                                                      D331Y
Human  301    RMLLKRGCNVNSTSSAGNTALHVAVMRNRF CAIVLLTHGANADARGEHGNTPLHLAMSK   360
              RMLLKRGC+V+STSS+GNTALHVAVMRNRF C  +VLLT+GANA ARGEHGNTPLHLAMSK
Mouse  301    RMLLKRGCDVDSTSSSGNTALHVAVMRNRF CVMVLLTYGANAGARGEHGNTPLHLAMSK   360

Human  361    DNVEMIKALIVFGAEVDTPNDFGETPTFLASKIGRLVTRKAILTLLRTVGAEYCFPPIHG   420
              DN+EM+KALIVFGAEVDTPNDFGETP  +ASKI +L+TRKA+LTLL+TLLKTVGA++ FP I G
Mouse  361    DNMEMVKALIVFGAEVDTPNDFGETPALIASKISKLITRKALLITLLKTVGADHHFPIIQG   420
```

FIG. 15A

```
                                    Q452X
Human  421  VPAEQGSAAPHHP-FSLERAQPPPISLNNLEIQDLMHISRARKPAFILGSMRDEKRTHDH  479
            V  EQGSAA   HP FSL+R QPP ISLNNLEI DLM ISRARKPAFIL SMRDEKR+HDH
Mouse  421  VSTEQGSAAATHPLFSLDRTQPPAISLNNLEIQDLMPISRARKPAFILSSMRDEKRSHDH  480

Human  480  LLCLDGGGVKGLIIIQLLIAIEKASGVATKDLFDWVAGTSTGGILALAILHSKSMAYMRG  539
            LLCLDGGGVKGL+ IIQLLIAIEKASGVATKDLFDWVAGTSTGGILALAILHSKSMAYMRG
Mouse  481  LLCLDGGGVKGLVIIQLLIAIEKASGVATKDLFDWVAGTSTGGILALAILHSKSMAYMRG  540

Human  540  MYFRMKDEVFRGSRPYESGPLEEFLKREFGEHTKMTDVRKPKVMLTGTLSDRQPAELHLF  599
            +YFRMKDEVFRGSRPYESGPLEEFLKREFLKREFGEHTKMTDV+KPKVMLTGTLSDRQPAELHLF
Mouse  541  VYFRMKDEVFRGSRPYESGPLEEFLKREFLKREFGEHTKMTDVKKPKVMLTGTLSDRQPAELHLF  600
                                         R632W R635Q
Human  600  RNYDAPETVREPRFNQNVNLRPPAQPSDQLVWRAARSSGAAPTYFRPNGRFLDGGLLANN  659
            RNYDAPE VREPR NQN+NL+PP  QP+DQLVWRAARSSGAAPTYFRPNGRFLDGGLLANN
Mouse  601  RNYDAPEAVREPRCNQNINLKPPTQPADQLVWRAARSSGAAPTYFRPNGRFLDGGLLANN  660

Human  660  PTLDAMTEIHEYNQDLIRKGQANKVKKLSIVVSLGTGRSPQVPVTCVDVFRPSNPWELAK  719
            PTLDAMTEIHEYNQD+IRKGQ NKVKKLSIVVSLGTG+SPQVPVTCVDVFRPSNPWELAK
Mouse  661  PTLDAMTEIHEYNQDMIRKGQGNKVKKLSIVVSLGTGKSPQVPVTCVDVFRPSNPWELAK  720
                      R741Q R747W
Human  720  TVFGAKELGKMVDCCTDPDGRAVDRARAWCEMVGIQYFRLNPQLGTDIMLDEVSDTVLV  779
            TVFGAKELGKMVDCCTDPDGRAVDRARAWCEMVGIQYFRLNPQLG+DIMLDEVSD VLV
Mouse  721  TVFGAKELGKMVDCCTDPDGRAVDRARAWCEMVGIQYFRLNPQLGSDIMLDEVSDAVLV  780

Human  780  NALWETEVYIYEHREEFQKLIQLLLSP  806
            NALWETEVYIYEHREEFQKL+QLLLSP
Mouse  781  NALWETEVYIYEHREEFQKIVQLLLSP  807
```

*FIG. 15B*

```
hPLA2g6    1   MQFFGRLVNTFSGVTNLFSNPFRVKEVAVADYTSSDRVREEGQLIFQNTPNRTWDCVLV    60
                                F72L
hPLA2g6   61   NPRNSQSGFRL QLELEADALVNFHQYSSQLLPFYESSPQVLHTEVLQHLTDLIRNHPSW   120
                                                                  KO^Bx2 (M179+)
hPLA2g6  121   SVAHLAVELGIRECFHHSRIISCANCAENEEGCTPLHLACRKGDGEILVELVQYCHTQMD   180
               Caspase-3 cleavage site (D183)
hPLA2g6  181   VT YKGETVEHYAVQGDNSQVLQLLGRNAVAGLNQVNNQGLTPLHLACQLGKQEMVRVLL   240 hPLA2g6  241   LCNARCNIMGPNGYPIHSAMKFSQKGCAEMIISMDSSQIHSKDPRYGASPLHWAKNAEMA   300
                                         D331Y
hPLA2g6  301   RMLLKRGCNVNSTSSAGNTALHVAVMRNRF CAIVLLTHGANADARGEHGNTPLHLAMSK   360
                                                          PIN domain (396-450)
hPLA2g6  361   DNVEMIKALIVFGAEVDTPNDFGETPTFLASKIGRLVTRKAILTLLRTVGAEYCFPPIHG   420
                                                         Q452X
hPLA2g6  421   VPAEQGSAAPHHP-FSLERAQPPPISINNLEL DLMHISRARKPAFILGSMRDEKRTHDH   479
                                                              Lipase site (519 TSTG)
hPLA2g6  480   LLCLDGGVKGLIIIQLLIAIEKASGVATKDLEDWVA TSTGGILALAILHSKSMAYMRG   539 hPLA2g6  540   MYFRMKDEVFRGSRPYESGPLEEFLKREFGEHTKMTDVRKPKVMLTGTLSDRQPAELHLF   599
```

FIG. 16A

```
                   R632W  R635Q
hPLA2g6  600  RNYDAPETVREPRFNQNVNLRPPAQPSDQLVWRAASSGAAPTYFRPNGRFLDGGLLANN  659
                             1-9-14 CaM binding (676-689)
hPLA2g6  660  PTLDAMTEIHEYNQDLIRKGOANKVKKLSIVVSLGTGRSPQVPVTCVDVFRPSNPWELAK  719
                    R741Q R747W  IQ CaM binding (748-759)
hPLA2g6  720  TVFGAKELGKMVVDCCTDPDGRAVDRARAWCEMVGIQYFRINPQLGTDIMLDEVSDTVLV  779
hPLA2g6  780  NALWETEVYIYEHREEFQKLIQLILLSP  806
```

*FIG. 16B*

PARKINSONS DISEASE MODEL AND METHODS

PRIORITY INFORMATION

This application claims priority to Provisional Application No. 61/792,916, filed Mar. 15, 2013, which is hereby incorporated herein by reference.

RELATED APPLICATIONS

This application is a divisional of application Ser. No. 14/213,359, filed Mar. 14, 2014 (now U.S. Pat. No. 9,599,605), which claims priority to Provisional Application No. 61/792,916, filed Mar. 15, 2013, which is hereby incorporated herein by reference.

SEQUENCE LISTING

The instant application contains a Sequence Listing which has been submitted electronically in ASCII format and is hereby incorporated by reference in its entirety. Said ASCII copy, created on Nov. 23, 2015, is named 1006_003_US1_SL.txt and is 17,467 bytes in size.

INTRODUCTION

Parkinson's disease (PD) is a degenerative disorder of the central nervous system, which results from the death of dopamine-generating (DA) neurons in the substantia nigra, a region of the midbrain. PD affects nearly a million Americans, with 50,000 new cases diagnosed in the U.S. each year. PD is the second most common neurodegenerative disorder after Alzheimer's disease. The prevalence of PD is about 0.3% of the whole population in industrialized countries. While genetically linked familial PD has early onset (between the ages of 20 and 50), the more common sporadic PD is occurring after the age of 50 (average 57±11). PD is more common in the elderly and prevalence rises from 1% in those over 60 years of age to 4% of the population over 80. The incidence of PD has been estimated between 8 and 18 per 100,000 person years.

The main motor symptoms of PD are collectively called parkinsonism, or a "parkinsonian syndrome" Parkinson's disease is often defined as a parkinsonian syndrome that is idiopathic (having no known cause), although some cases have a genetic origin. Early in the course of the disease, the most obvious symptoms are movement-related, such as shaking, rigidity, postural instability, slowness of movement, difficulty with walking, impaired gait and tendency to fall. Later, cognitive and behavioral problems may arise, with dementia commonly occurring in the advanced stages of the disease. Other symptoms include sensory, sleep and emotional problems.

There is no effective treatment to prevent or stop PD development. Modern treatments are focused on managing the early motor symptoms of the disease, mainly through the use of levodopa and dopamine agonists. As the disease progresses and dopaminergic neurons continue to be lost, these drugs eventually become ineffective at treating the symptoms and at the same time produce a complication called dyskinesia, marked by involuntary writhing movements. Diet and some forms of rehabilitation have shown some effectiveness at alleviating symptoms. Surgery and deep brain stimulation have been used to reduce motor symptoms as a last resort in severe cases where drugs are ineffective. Medications to treat non-movement-related symptoms of PD, such as sleep disturbances and emotional problems, also exist.

Despite extraordinary research efforts (with more than 2,000 articles on PD published annually), there is still no effective treatment for this devastating disease. Accordingly, there is a need for cellular and animal models to study PD and for use in identifying agents that modulate PD and that may be useful as therapeutics to treat or prevent PD. This disclosure addresses these and other needs.

SUMMARY

Numerous mutations in the Pla2g6 gene are associated with familial and sporadic Parkinson's disease (PD) and parkinsonism (References 4-10), but the underlying mechanism is unknown. The Pla2g6 gene (FIG. 6a) encodes multiple splice variants of $Ca^{2+}$-independent phospholipase A2 group 6 (PLA2g6) protein, that has characteristic $Ca^{2+}$-independent catalytic activity regulated by inhibitory calmodulin (CaM) (for recent review, see Reference 11). It is currently unknown which cellular function and which variant of PLA2g6 protein is involved in the demise of dopaminergic (DA) neurons in the substantia nigra pars compacta (SNpc), which is a major contributing factor to motor dysfunction in PD (Reference 12). The multifaceted nature of PLA2g6 has presented additional challenges, as in contrast to PARK14 mutations in PLA2g6 that lead to PD, some other mutations in the Pla2g6 gene have been linked to INAD (infantile neuroaxonal dystrophy) and NBIA (neurodegeneration with brain iron accumulation) in human and in mouse models (References 13-20), and attributed to the loss of PLA2g6 catalytic activity and disruption of lipid remodeling (References 21-25). However, recent studies (See Reference 18) demonstrated that, in contrast to INAD mutations, PARK14 mutations do not affect catalytic activity of PLA2g6, highlighting the question of which specific function of PLA2g6 is responsible for its association with PD. Prior mouse mutants have not answered this question.

The Examples presented herein (FIGS. 1-14) provide a novel PLA2g6 mouse model ($KO^{Ex2}$) in which genetic deletion of Exon 2 results in a loss of dopaminergic (DA) neurons in substantia nigra (SN), and development of PD-like motor dysfunction that can be significantly improved by L-DOPA. The functional and molecular analysis of PLA2g6 and $Ca^{2+}$ homeostasis in the cells from $KO^{Ex2}$ mice reveals a total loss of PLA2g6 activation by the depletion of intracellular $Ca^{2+}$ stores, ablation of PLA2g6-dependent store-operated $Ca^{2+}$ entry (SOCE), and sustained depletion of intracellular $Ca^{2+}$ stores. Importantly, these deficiencies could be rescued by expression of a wild type PLA2g6(L), but not $PLA2g6^{F72L}$ mutant associated with PARK14-dependent human PD. Moreover, the N terminus of PLA2g6 (that gets ablated following deletion of Exon 2) is identified as essential for its interaction with endogenous STIM1 ($Ca^{2+}$ sensor in endoplasmic reticulum), and a specific splice variant of PLA2g6 is shown to be required for SOCE and refilling of intracellular $Ca^{2+}$ stores. Discovery of a causal relationship between impaired PARK14 (PLA2g6)-dependent SOCE, depletion of intracellular $Ca^{2+}$ stores, the loss of DA neurons in SN and development of PD-like phenotype in ageing $KO^{Ex2}$ mice unveils a novel molecular mechanism underlying familial and age-dependent PD.

In a first aspect this disclosure provides genetically modified animals, comprising a mutant allele of PLA2g6, wherein store-operated $Ca^{2+}$ entry (SOCE) is impaired in the genetically modified animal. In some embodiments the genetically modified animals comprise two mutant alleles of PLA2g6. In some embodiments the genetically modified animal is homozygous for a single mutant allele of PLA2g6. In some embodiments the mutant PLA2g6 protein(s) encoded by the mutant allele(s) retain wild-type catalytic activity. In some embodiments activation of PLA2g6 and SOCE by depletion of endoplasmic reticulum (ER) $Ca^{2+}$ stores is impaired in the genetically modified animal. In some embodiments the genetically modified animal develops PD-related deficit(s). In some embodiments the genetically modified animal develops a localized loss of dopaminergic neurons. In some embodiments the genetically modified animal is a mammal. In some embodiments the mammal is a mouse. In some embodiments the mammal is a human.

In another aspect this disclosure provides genetically modified animal cells comprising two mutant alleles of PLA2g6, wherein store-operated $Ca^{2+}$ entry (SOCE) is impaired in the genetically modified animal cell. In some embodiments the genetically modified animal cell is homozygous for a single mutant allele of PLA2g6. In some embodiments the mutant PLA2g6 protein(s) encoded by the mutant allele(s) retain a substantially wild-type catalytic activity. In some embodiments activation of PLA2g6 and SOCE by depletion of endoplasmic reticulum (ER) $Ca^{2+}$ stores is impaired in the genetically modified animal cell. In some embodiments the genetically modified animal cell is a primary cell derived from a genetically modified animal of this disclosure. In some embodiments the genetically modified animal cell is from a cell line. In some embodiments the genetically modified animal cell is a mammal cell. In some embodiments the mammal is a mouse. In some embodiments the mammal is a human.

In another aspect this disclosure provides methods of screening a compound for an effect on the SOCE pathway and/or ER $Ca^{2+}$ stores, comprising: administering the compound to a genetically modified animal comprising two mutant alleles of PLA2g6, wherein store-operated $Ca^{2+}$ entry (SOCE) is impaired in the genetically modified animal; and determining the effect of the compound on SOCE pathway activation in the animal cells. In some embodiments the genetically modified animal is homozygous for a single mutant allele of PLA2g6. In some embodiments the mutant PLA2g6 protein(s) encoded by the mutant allele(s) retain a substantially wild-type catalytic activity. In some embodiments activation of SOCE by depletion of endoplasmic reticulum (ER) $Ca^{2+}$ stores is impaired in the genetically modified animal. In some embodiments the genetically modified animal develops PD-related deficit(s). In some embodiments the genetically modified animal develops a localized loss of dopaminergic neurons. In some embodiments the genetically modified animal is a mammal. In some embodiments the mammal is a mouse or a human. In some embodiments the methods further comprise administering a control compound that activates SOCE to a genetically modified animal; determining the effect of the control compound on SOCE in the animal; and comparing the effect of the compound on SOCE in the animal to the effect of the control compound on SOCE in the animal. In some embodiments the compound activates SOCE in the genetically modified animal and is thereby identified as a SOCE activator.

In another aspect this disclosure provides methods of screening a compound for an effect on the SOCE pathway, comprising: providing the compound to a genetically modified animal cell comprising two mutant alleles of PLA2g6, wherein store-operated $Ca^{2+}$ entry (SOCE) is impaired in the genetically modified animal cells; and determining the effect of the compound on SOCE and/or ER $Ca^{2+}$ storage in the animal cells. In some embodiments the genetically modified animal cell is homozygous for a single mutant allele of PLA2g6. In some embodiments the mutant PLA2g6 protein(s) encoded by the mutant allele(s) retain a substantially wild-type catalytic activity. In some embodiments SOCE activation by depletion of endoplasmic reticulum (ER) $Ca^{2+}$ stores is impaired in the genetically modified animal cell. In some embodiments the cell is a primary cell derived from a genetically modified animal comprising a mutant allele of PLA2g6, wherein store-operated $Ca^{2+}$ entry (SOCE) is impaired in the genetically modified animal. In some embodiments the genetically modified animal cell is from a cell line. In some embodiments the genetically modified animal cell is a mammal cell. In some embodiments the mammal is a mouse or human. In some embodiments the methods further comprise administering a control compound that activates SOCE to a genetically modified animal cell; determining the effect of the control compound on SOCE in the genetically modified animal cell; and comparing the effect of the compound on SOCE in the genetically modified animal cell to the effect of the control compound on SOCE in the genetically modified animal cell. In some embodiments the compound activates SOCE in the genetically modified animal cell and is thereby identified as a SOCE activator.

In another aspect this disclosure provides methods of treating or preventing PD-related deficit(s) in an animal, comprising: a) characterizing a compound as a SOCE activator by a method of this disclosure; and b) administering an effective amount of the compound to the animal to thereby treat or prevent the PD-related deficit(s) in the animal. In some embodiments the animal is a human with Parkinson's disease.

In another aspect this disclosure provides methods of preventing impairment of store-operated $Ca^{2+}$ entry (SOCE) pathway activity in a cell, comprising introducing a caspase-3 cleavage-resistant PLA2g6 protein into the cell. In some embodiments the caspase-3 cleavage-resistant PLA2g6 protein does not comprise a wild type caspase-3 cleavage site. In some embodiments the caspase-3 cleavage-resistant PLA2g6 protein is introduced into the cell by introduction of a nucleic acid encoding the caspase-3 cleavage-resistant PLA2g6 protein into the cell. In some embodiments the nucleic acid encoding the caspase-3 cleavage-resistant PLA2g6 protein is present in a vector and operably linked to expression control sequences sufficient for expression in the cell. In some embodiments the vector is a viral vector. In some embodiments the cell is a cell that is cultured in vitro. In some embodiments the cell is an in vivo cell.

In another aspect this disclosure provides methods of treating or preventing PD-related deficit(s) in an animal, comprising introducing a caspase-3 cleavage-resistant PLA2g6 protein into neurons of the animal. In some embodiments the caspase-3 cleavage-resistant PLA2g6 protein is introduced into dopaminergic neurons of the animal. In some embodiments the caspase-3 cleavage-resistant PLA2g6 protein does not comprise a wild type caspase-3 cleavage site. In some embodiments the caspase-3 cleavage-resistant PLA2g6 protein is introduced into the neurons by introduction of a nucleic acid encoding the caspase-3 cleavage-resistant PLA2g6 protein into the neurons. In some embodiments the nucleic acid encoding the caspase-3 cleavage-resistant PLA2g6 protein is present in a vector and operably linked to expression control sequences sufficient for expression in the neurons. In some embodiments the vector is a viral vector. In some embodiments the animal is a human with Parkinson's disease.

BRIEF DESCRIPTION OF THE DRAWINGS

FIGS. 3A to 3E show PCR-based genotyping and confirmation of the constitutive knockout of PLA2g6 Exon 2 at the transcript level. A is a schematic representation of WT Pla2g6 locus with positions of four sets of primers used for PCR-based genotyping (sets 1 and 2) of the colony, or for confirmation of the lack of Pla2g6 exon 2 in transcripts from mouse brains (set 3 and 4). B and C show representative results of tail DNA genotyping for 9 animals from the colony using PCR primer sets 1 and 2. Expected length of PCR products for primer set 1 are 4028 (WT) and 2900 bp ($KO^{Ex2}$ allele), and for set 2 only WT allele (857 bp product) can be detected. Taken together, PCR with both sets of primers allowed for unambiguous determination of the Pla2g6 locus genotype for each animal within the colony. D and E show total RNA isolated from brains of two representative pairs of WT and Pla2g6Ex2 KO animals was reverse-transcribed and used as a template for PCR with primer sets 3 and 4. Expected length of PCR products for primer set 3 are 736 (WT) and 486 bp (KOEx2 allele), and for set 4 only WT allele (644 bp product) can be detected. As expected, for both animals previously genotyped as Pla2g6 $KO^{Ex2}$ (using primer sets 1 and 2), transcripts coding for PLA2g6 are present in the brain, but are missing exon 2. Additionally, the product amplified with the primer set 3 from brains of $KO^{Ex2}$ mice was cloned and sequenced, and both the expected cDNA sequence and the lack of Exon 2 were confirmed (data not shown).

B: WB showing ability of PIN antibody to recognize endogenous full length (and potentially shorter, truncated) variant of PLA2g6(L) in membrane fractions of human Jurkat and HEK293-F cells.

Figures 5A, 5B:
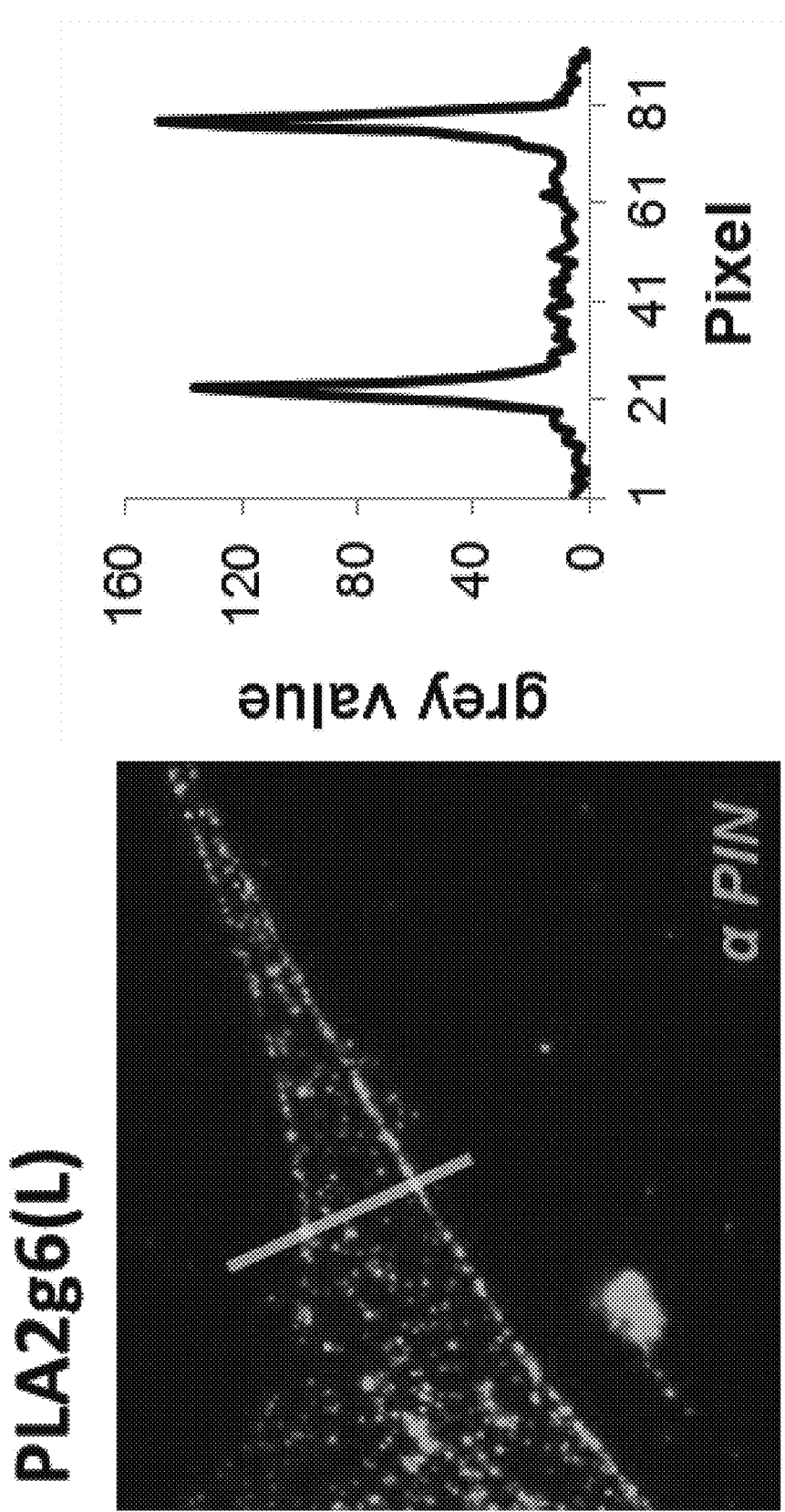

FIGS. 5A and 5B show that endogenous plasma membrane-associated PLA2g6(L) is detected by PIN antibody in MEF cells. A: Immunostaining of endogenous PLA2g6(L) in WT MEF cells with PIN antibody specific to mouse PIN region of PLA2g6(L). Fixation and staining procedure were the same as described for P-LISA in material and methods. Primary antibody dilution was 1:100 and Alexa488 anti-rabbit (1:200, Invitrogen) was used as secondary antibody. B: Line profile of fluorescence intensity in the section of the cell (shown in A) demonstrating plasma membrane localization of PIN signal. Profile analysis was done using the plot profile tool in ImageJ. The line width was set to 1 Pixel.

FIGS. 6A to 6H demonstrates that genetic oblation of N-terminus of PLA2g6 (achieved by genetic knock out of Exon 2) does not affect PLA2g6 catalytic activity, but leads to Parkinson's disease-like phenotype in a new $KO^{Ex2}$ mouse model. A: Schematic illustration of Pla2g6 (PARK14) gene (top) shows exons and ATG sites; PLA2g6 protein (bottom) shows corresponding position of functional domains. B: Simplified illustration of the approach to creation of a new $KO^{Ex2}$ mouse model. C: Results of qRT-PCR analysis (average±SD) of expression levels of (L) and (S) splice variants of PLA2g6 in brain and MEFs from WT and $KO^{Ex2}$ mice. D: Catalytic activity of PLA2g6 in homogenates of brain and MEFs from WT and $KO^{Ex2}$ mice: summary data (±SEM) from 3 independent experiments show no difference in catalytic activity of PLA2g6 in WT and $KO^{Ex2}$. E: Western blot shows the absence of the full length PLA2g6 (L) protein, but the presence of truncated product in $KO^{Ex2}$ mice: (WT) and ($KO^{Ex2}$) show endogenous protein from testis of WT and $KO^{Ex2}$ mice; $(L)^{1-806}$ and $^{(L)179-806}$ represent recombinant full-length and N-terminally truncated $^{myc}$PLA2g6(L)$^{his}$; F: age-dependent development of motor deficit in $KO^{Ex2}$, but not WT mice; (see methods); insert illustrates unstable gait of representative 18 month-old $KO^{Ex2}$ animal. G and H: Immunostaining and quantitative analysis of the number of TH$^+$ positive (brown) neurons in SNpc in the brain from WT and $KO^{Ex2}$ littermates (16 months old): images of full slices and corresponding 5× magnification of SNpc. Summary data from stereological analysis of 3 pairs of 16 months old littermates show significant (***p<0.001) reduction in the number of TH$^+$ neurons in $KO^{Ex2}$ mice.

Figure 7:
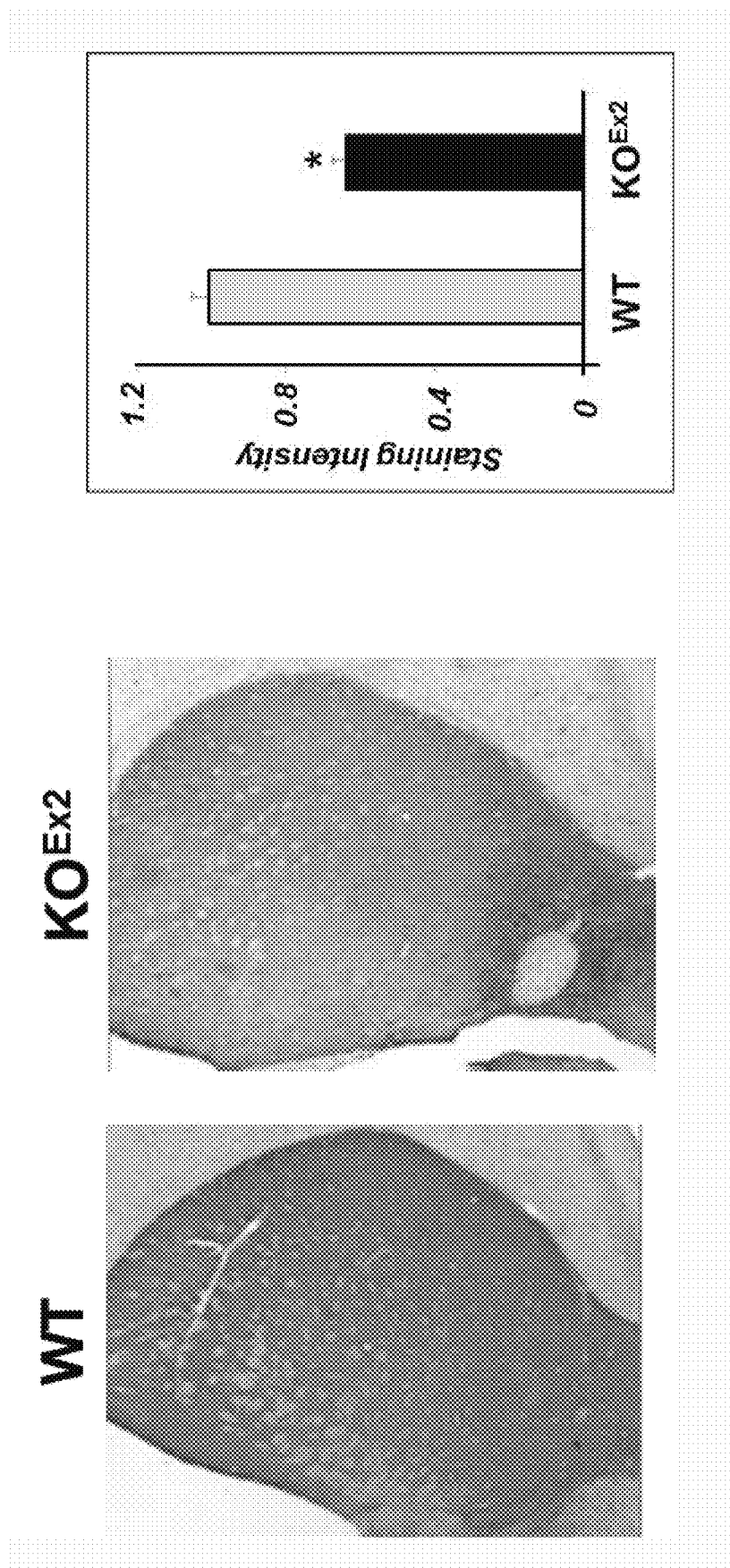

FIG. 7 shows representative staining of TH positive projections in striatum of WT and $KO^{Ex2}$ littermates. Immunostaining for TH+ in Caudate nucleus area of the brain of 16 months old littermates. Bar graph shows average±SEM intensity of staining relative to WT.

Figure 8:
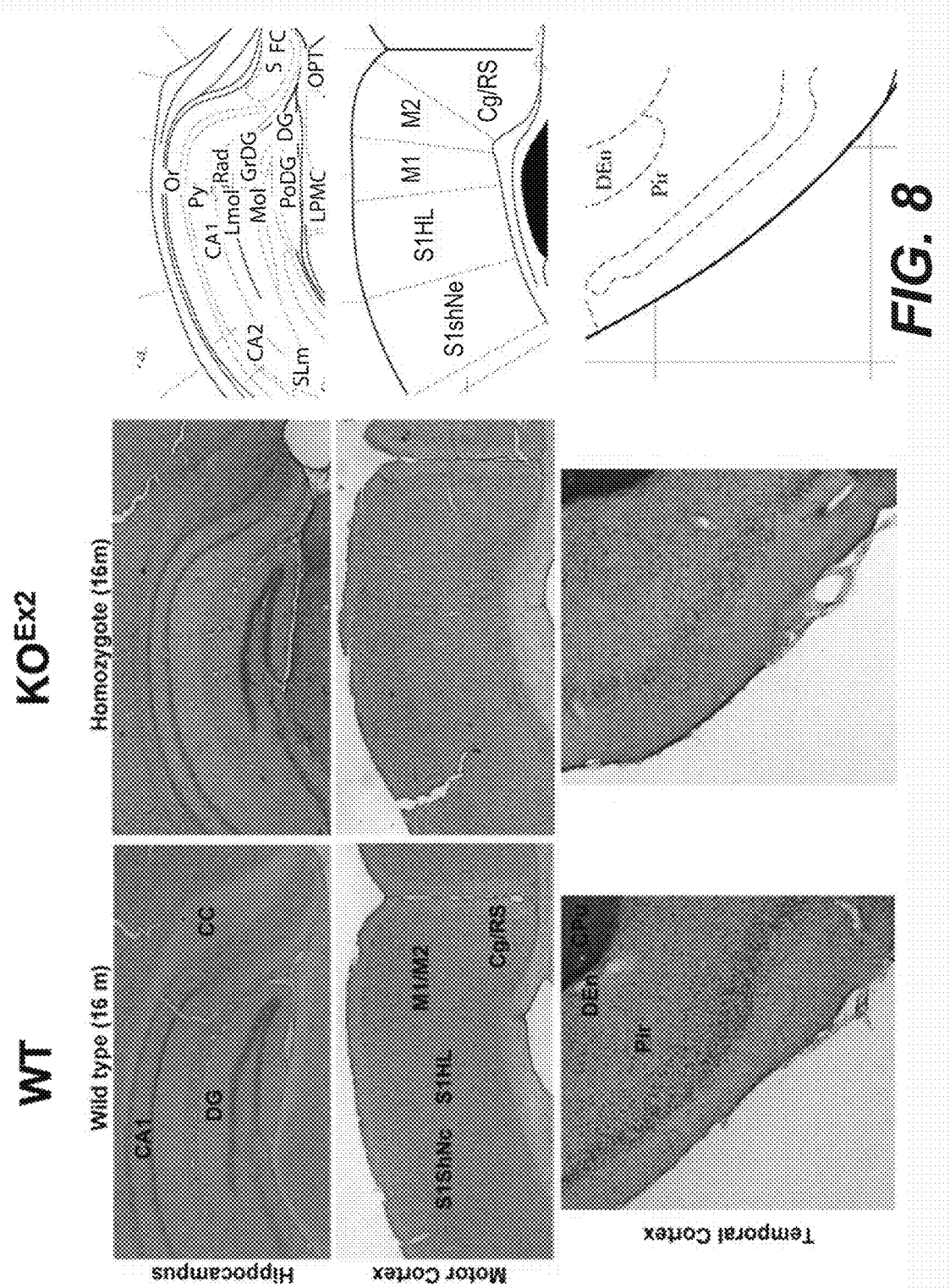

FIG. 8 shows histology of WT and $KO^{Ex2}$ mouse brain. Coronal sections of 16 month old WT and $KO^{Ex2}$ mice were stained with H&E. Upper panel, Hippocampal region: CA1 (Cornu Ammonis 1), DG (dentate gyrus), and CC (corpus callosum). Middle panel, Motor Cortex region: S1ShNc (primary somatosensory cortex, shoulder/neck region), S1HL (primary somatosensory cortex, hindlimb region), M1/M2 (primary and secondary motor corteces), Cg/RS (cingulate/retrosplenial cortex). Lower panel, Temporal cortex: Pir (piriform cortex), DEn (dorsal endopiriform nucleus), CPu (caudate putamen (striatum)). Original magnification: 4×.

Figure 9:
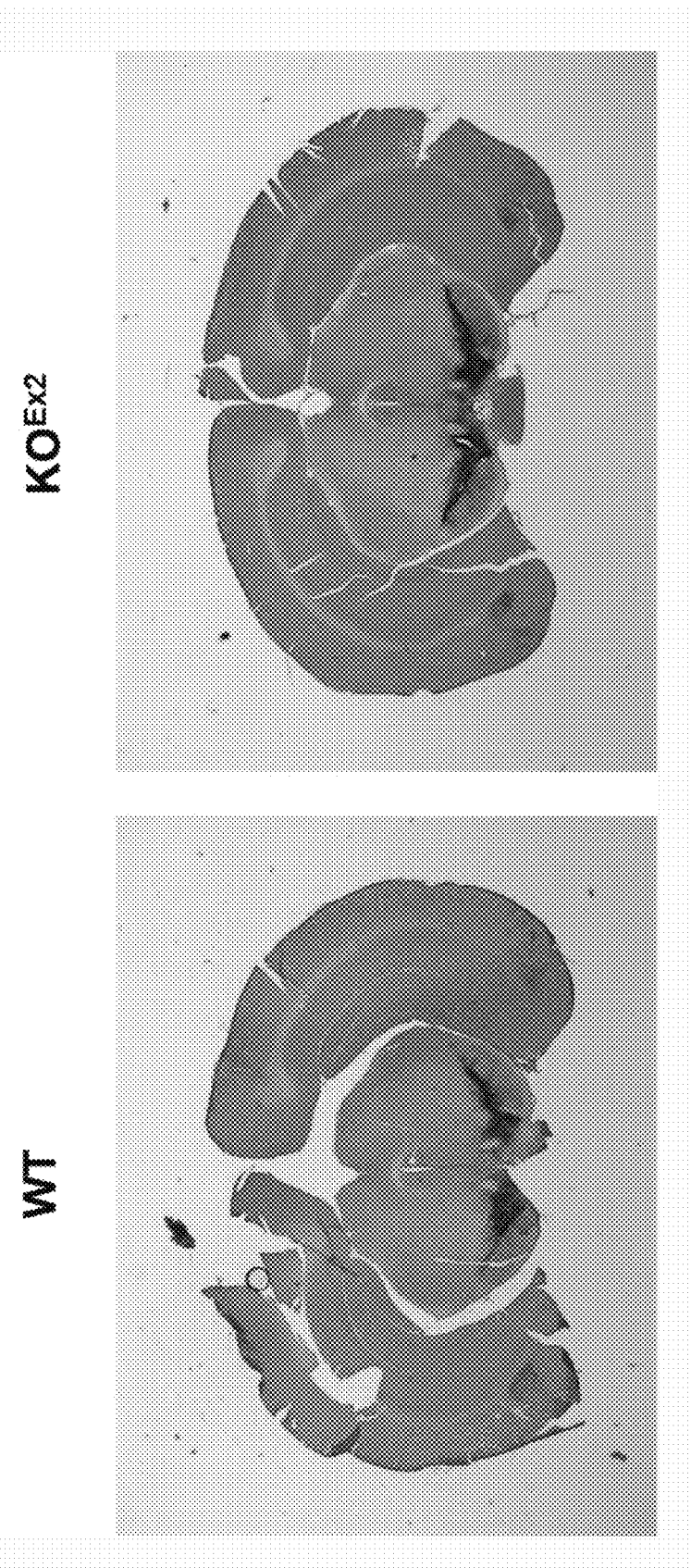

FIG. 9 shows representative brain slices from young (6 month old) WT and KO$^{Ex2}$ littermates. Immunostaining for TH+ in nigrostriatal area of the brain. Total counts of TH+ neurons show no significant differences in young WT and KO$^{Ex2}$ animals.

FIGS. 10A to 10E show that KO$^{Ex2}$ mice develop progressive age-dependent Parkinson's disease-like phenotype. Behavioral studies of the age-matched groups of WT and KO$^{Ex2}$ mice show results of: A: Limb-clasping test B: Rotarod test; C: Grip test, D: Beam balance test, E: L-DOPA test at different ages. All data are mean±SEM, with number of animals tested for each age group shown above each bar, ($p<0.01$), *($p<0.001$).

Figure 11A:
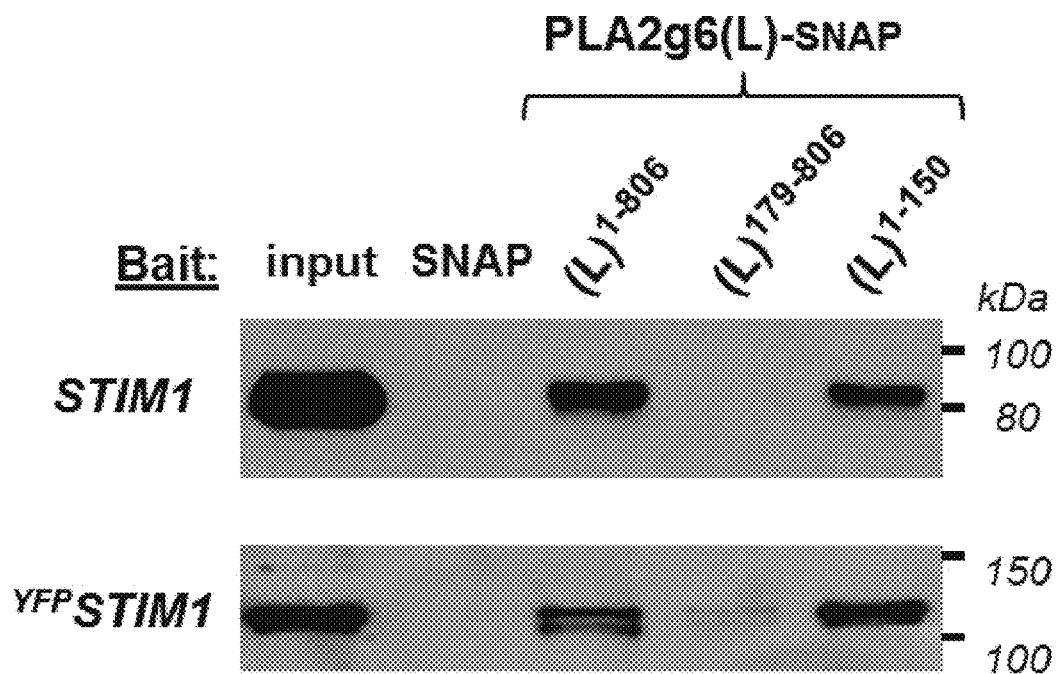
Figure 11B:
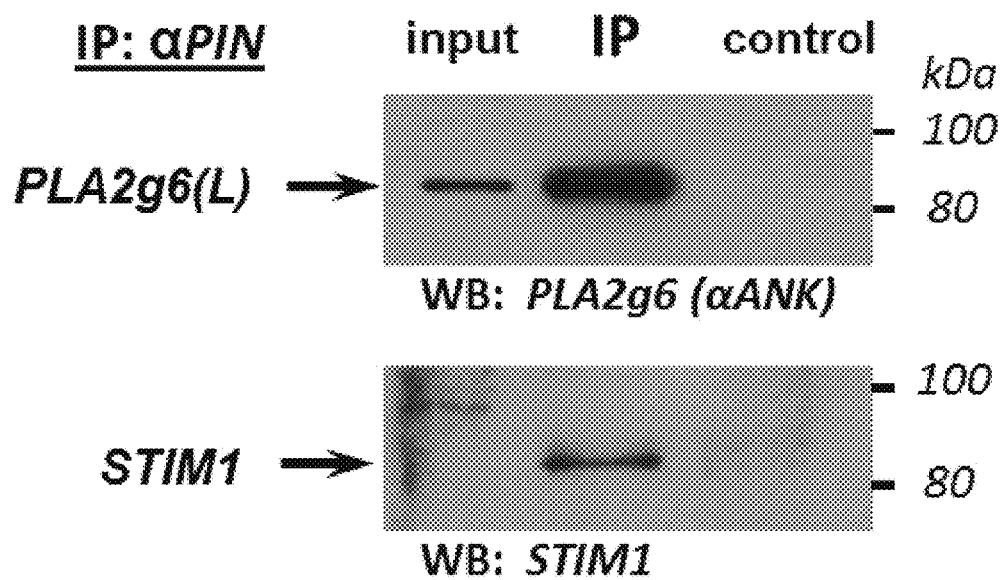
Figure 11C:
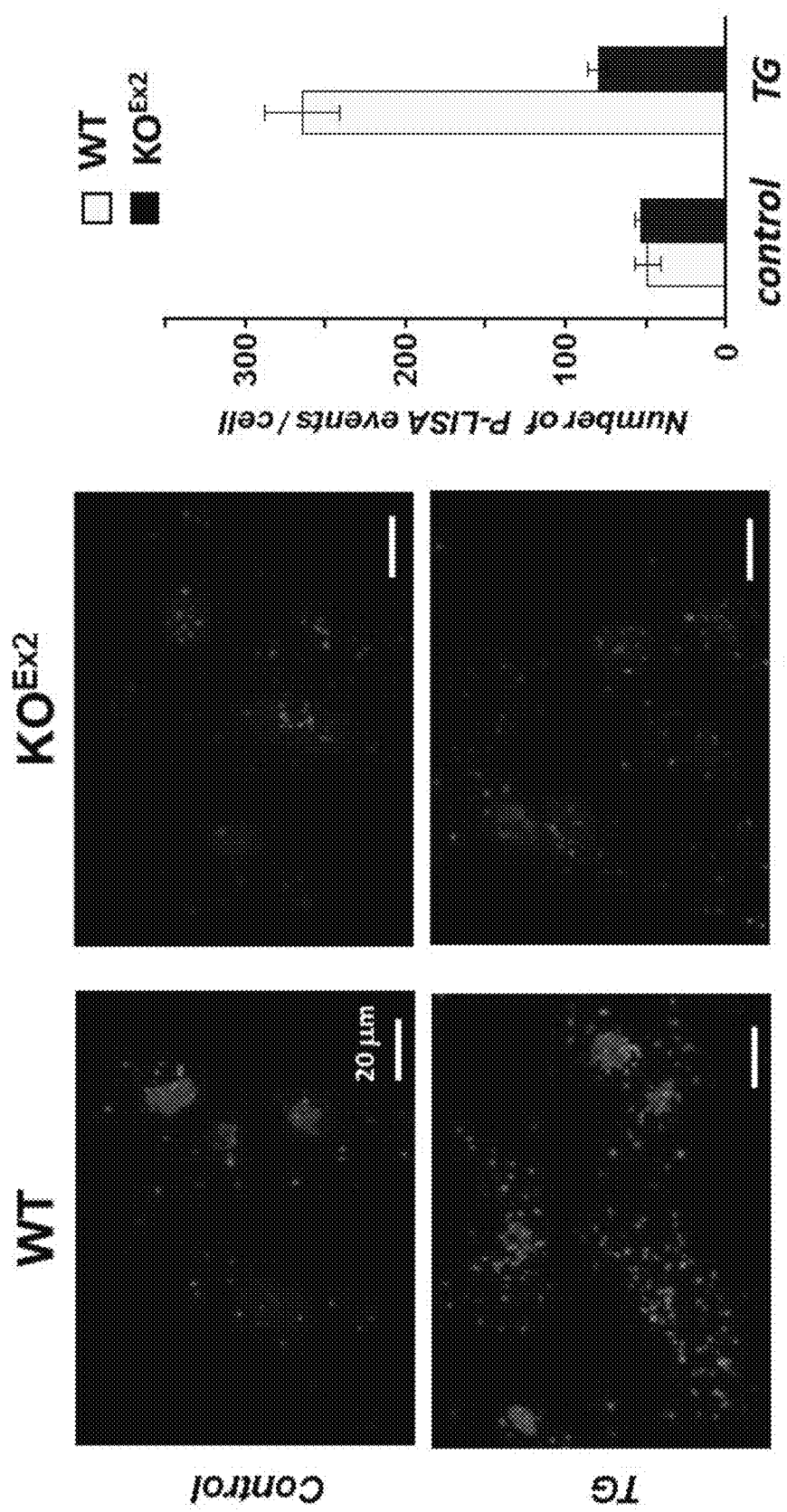

FIGS. 11A to 11C show that PLA2g6(L) interacts and co-localizes with STIM1. A: Endogenous STIM1 (upper panel), and overexpressed $^{YFP}$STIM1 (lower panel) bind to SNAP-immobilized full-length (L)$^{1-806}$ and N-terminus (L)$^{1-150}$, but not N-terminally truncated $^{(L)179-806}$ PLA2g6 (Supplementary FIG. 11). B: Endogenous STIM1 co-immunoprecipitates with endogenous PLA2g6(L) on PIN antibody (see Supplementary FIG. 12). C: Results of Proximity Ligation In Situ Assay (P-LISA) in control and TG-treated WT and KO$^{Ex2}$ MEFs (Supplementary FIG. 13-14). Images show red dots that represent P-LISA events of co-localization of endogenous PLA2g6(L) and STIM1; nuclei (DAPI) are blue. Summary data show the average number of P-LISA signals per cell (±SEM), ***($p<0.001$).

FIGS. 12A to 12C show that the N terminus of PLA2g6 is required and sufficient for in vitro complex formation with STIM1. Results of pull-down experiments as presented in FIG. 3a. A: with full-sized original images of immunoblots (B and C). Pull-down experiments show that endogenous STIM1 (from extracts of Jurkat T lymphocytes, left panel), as well as overexpressed YFPSTIM1 (from extracts of FreeStyle™ 293-F cells, right panel) bind to SNAP-immobilized full-length PLA2g6(L) (shown as (L)1-806), but not to PLA2g6(L)179-806 that mimics N-terminally truncated protein expected in KOEx2 mice. Importantly, these blots show that the first 150aa of N terminus of PLA2g6 (shown as (L)1-150) are sufficient to bind STIM1, and there is no binding to SNAP control.

Figures 13A, 13B, 13C:
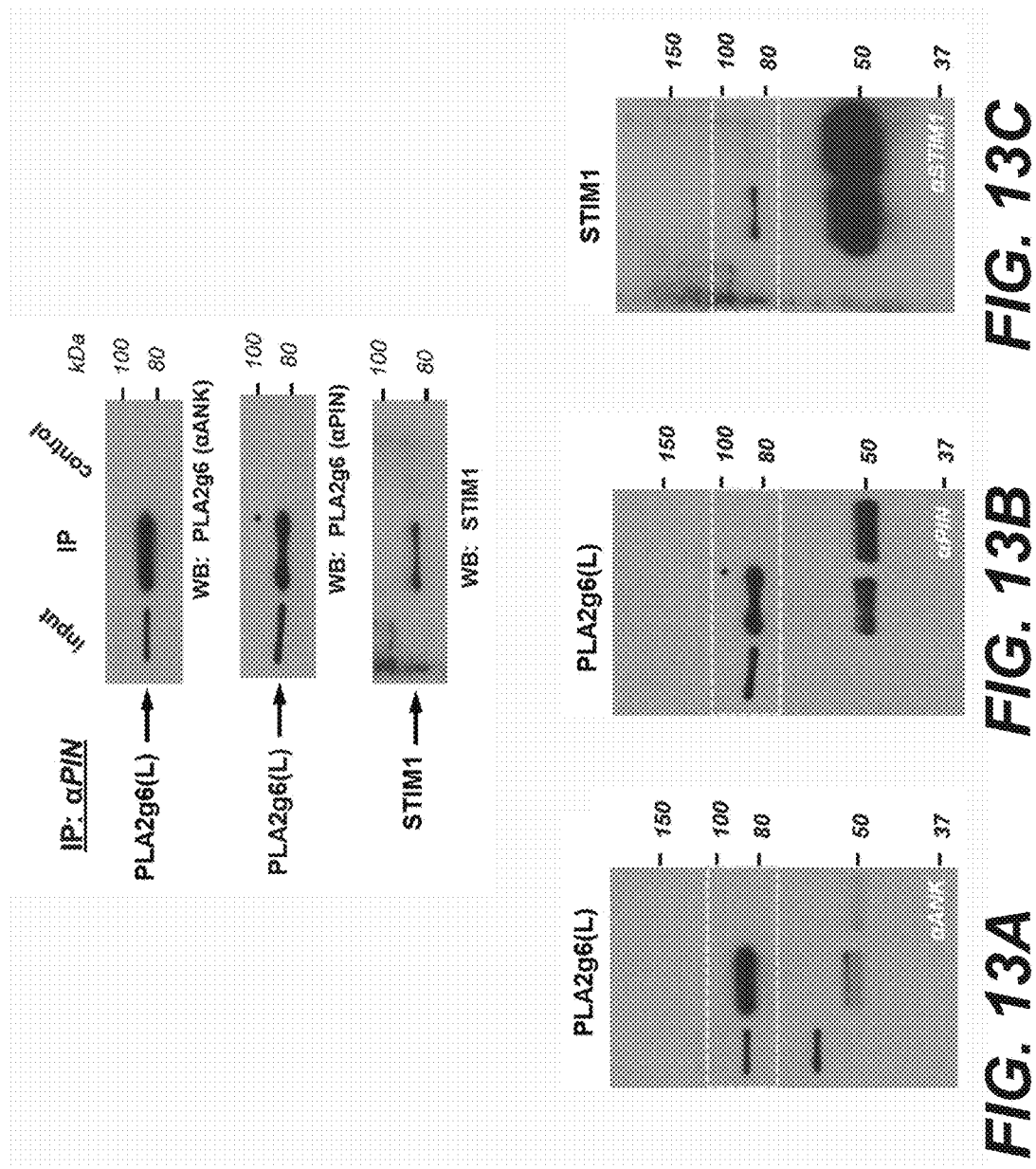

FIGS. 13A to 13C show STIM1 co-immunoprecipitates from extracts of WT mouse testes together with PLA2g6(L). Extended version of FIG. 3b (on the top) and full-sized images (A, B, C) of corresponding immunoblots. PIN antibody immunoprecipitates PLA2g6(L) from extracts of testes from WT mice in a complex with STIM1. Identity of the targeted PLA2g6 is confirmed here by immunoblotting with immunoprecipitating antibody (αPIN) and antibody directed against Ankyrin Repeats region of PLA2g6 (αANK).

Figures 14A, 14B:
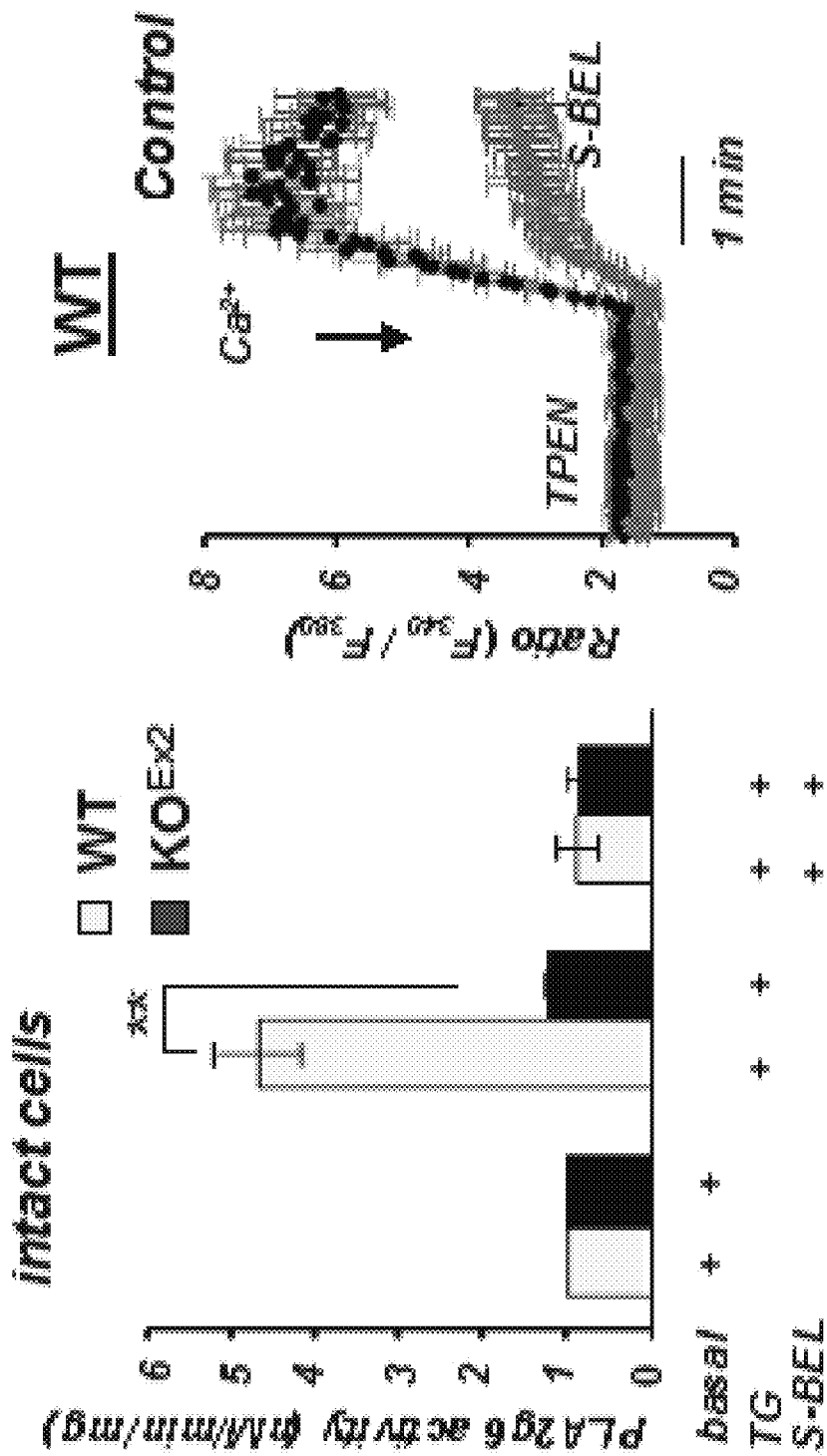
Figure 14D:
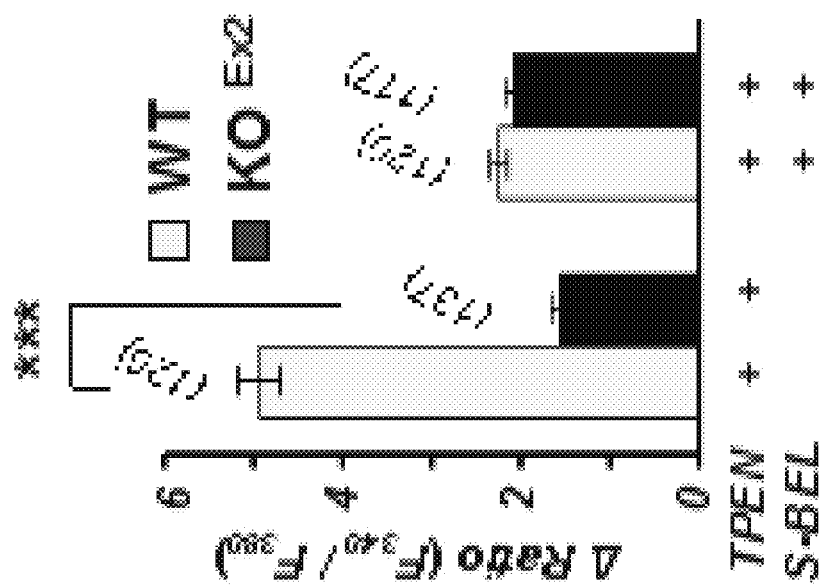
Figure 14C:
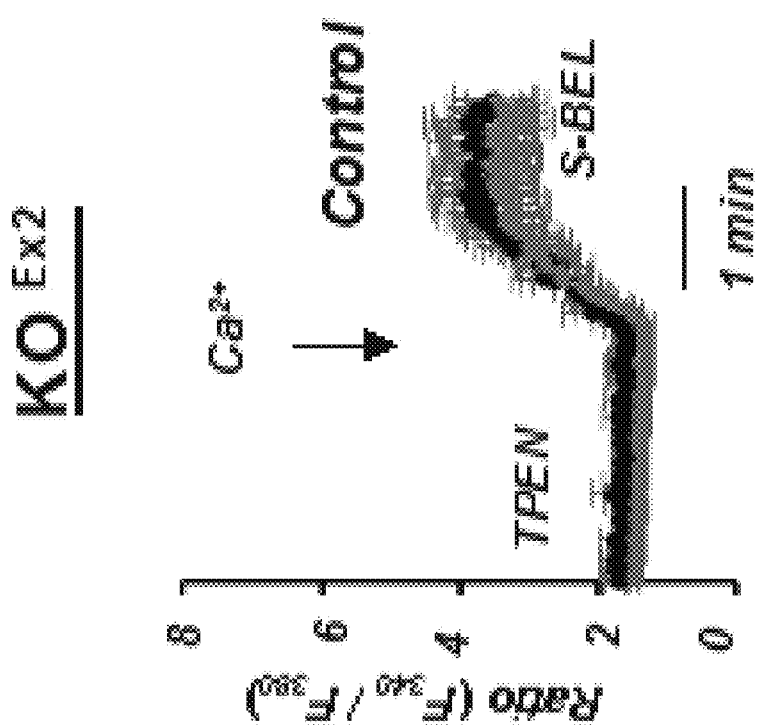
Figure 14F:
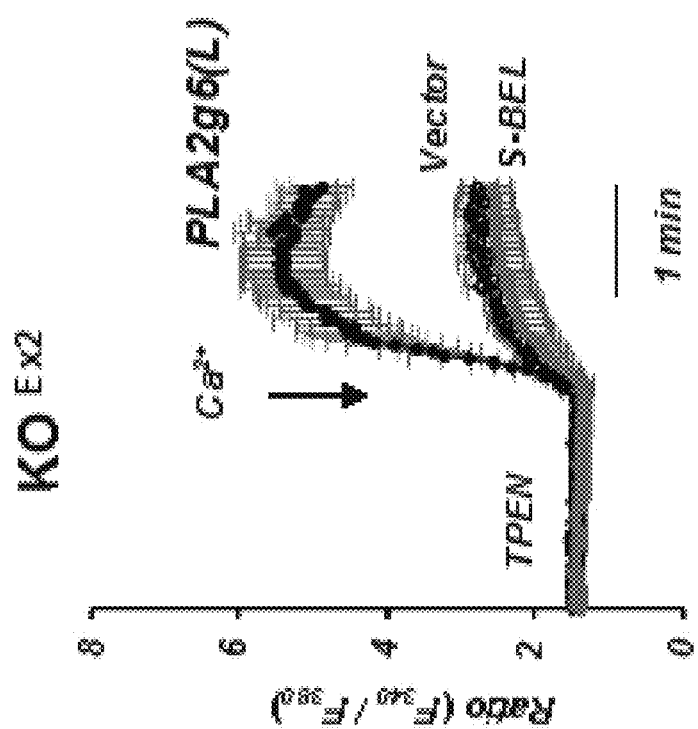
Figure 14E:
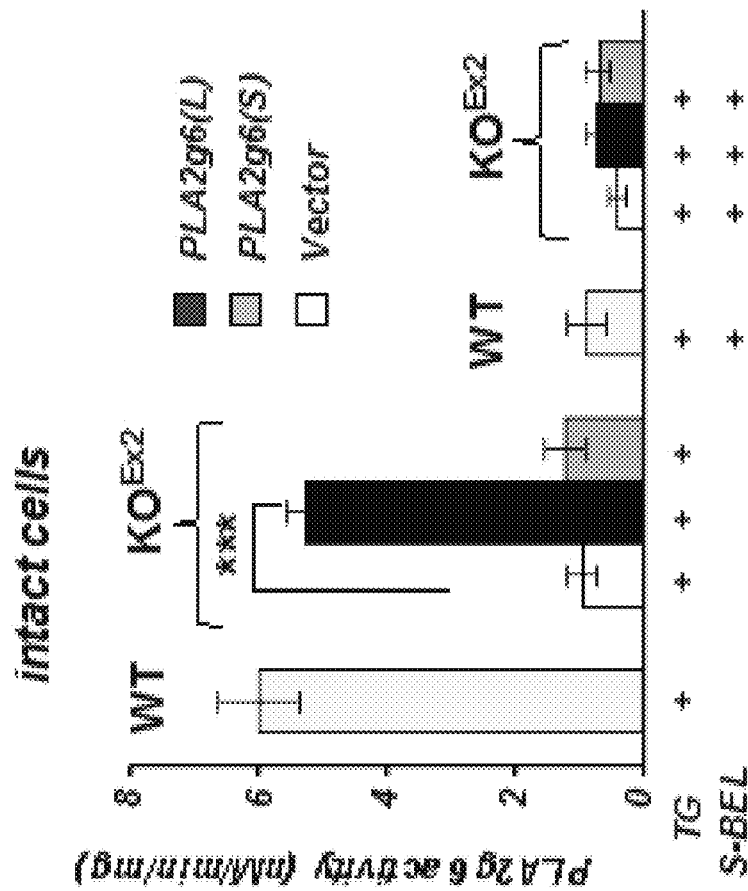
Figure 14I:
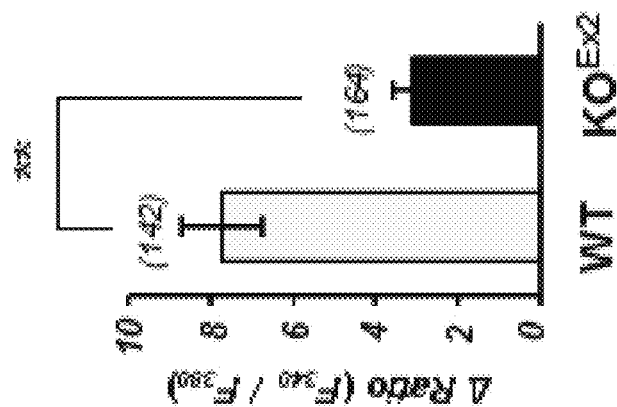
Figure 14H:
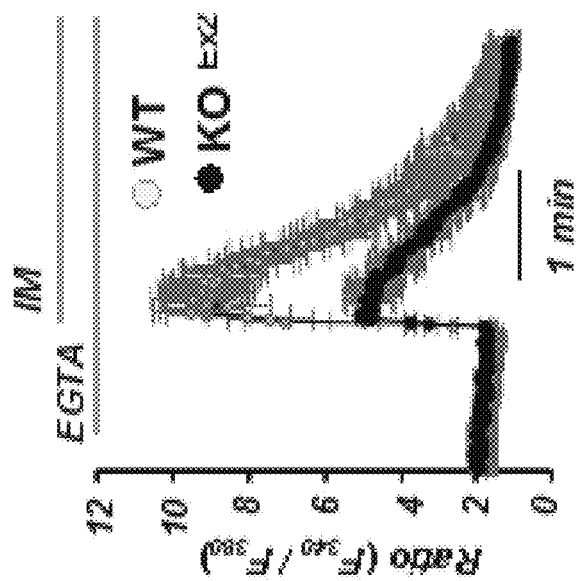
Figure 14G:
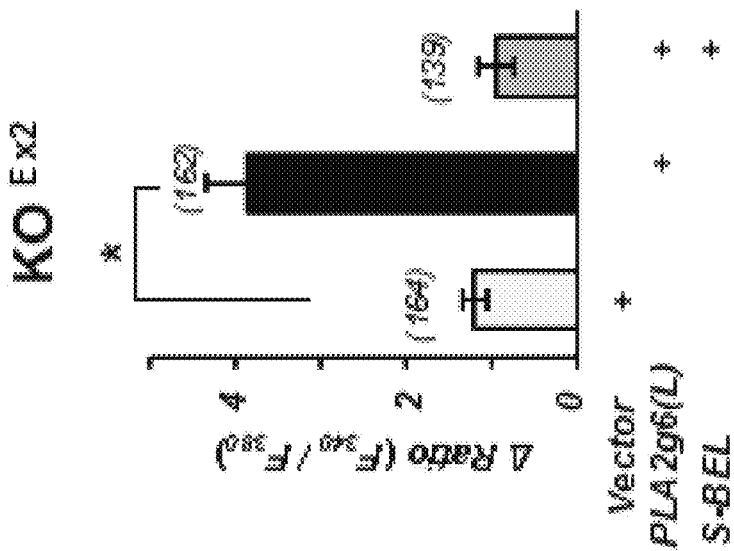
Figure 14K:
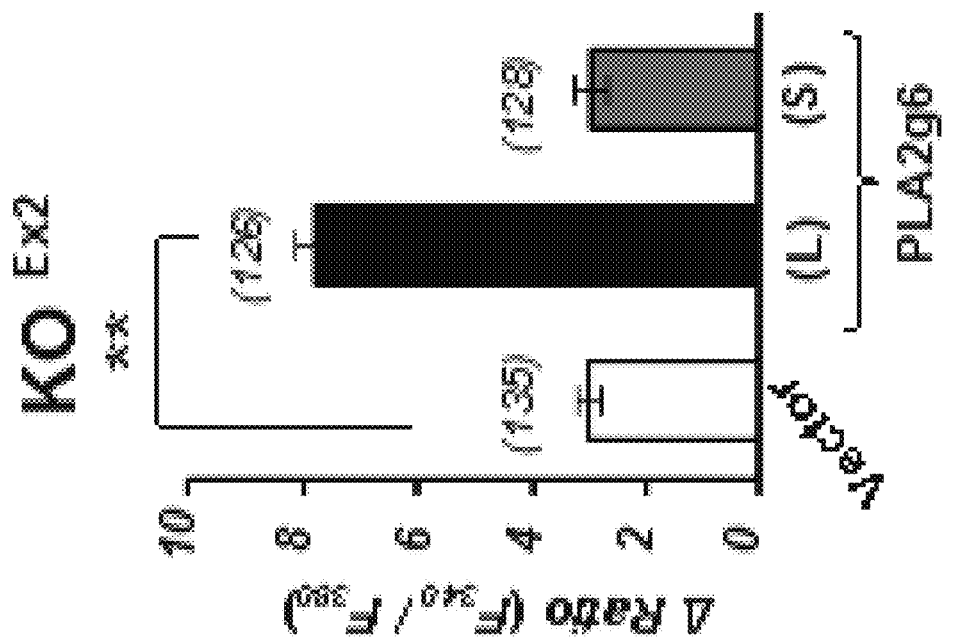
Figure 14J:
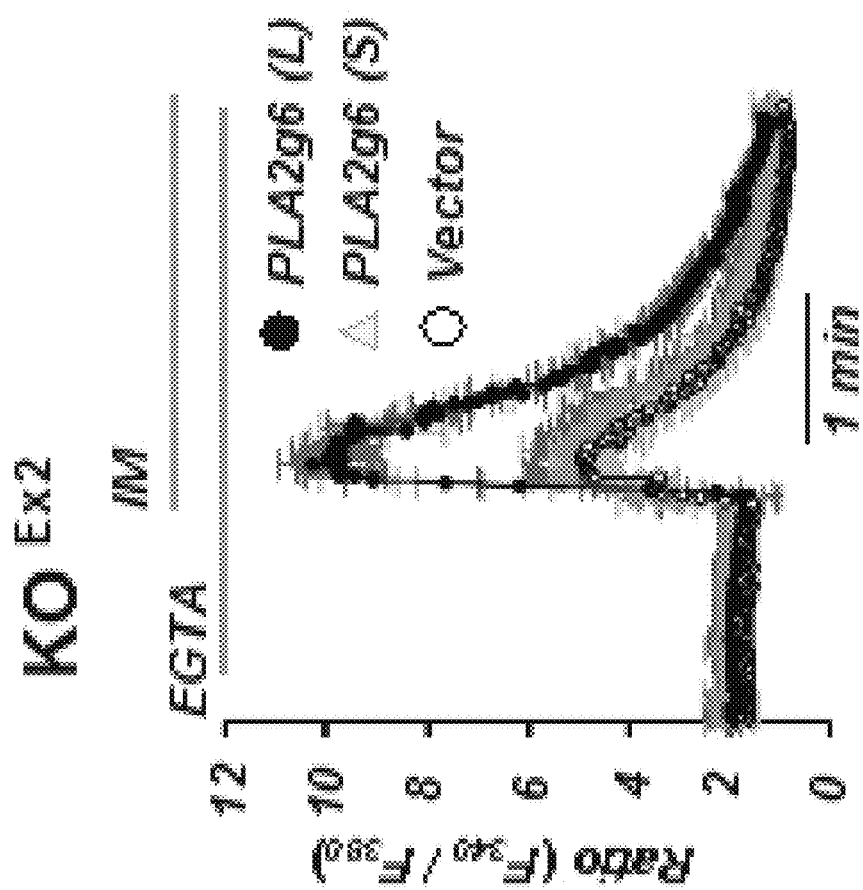
Figure 14L:
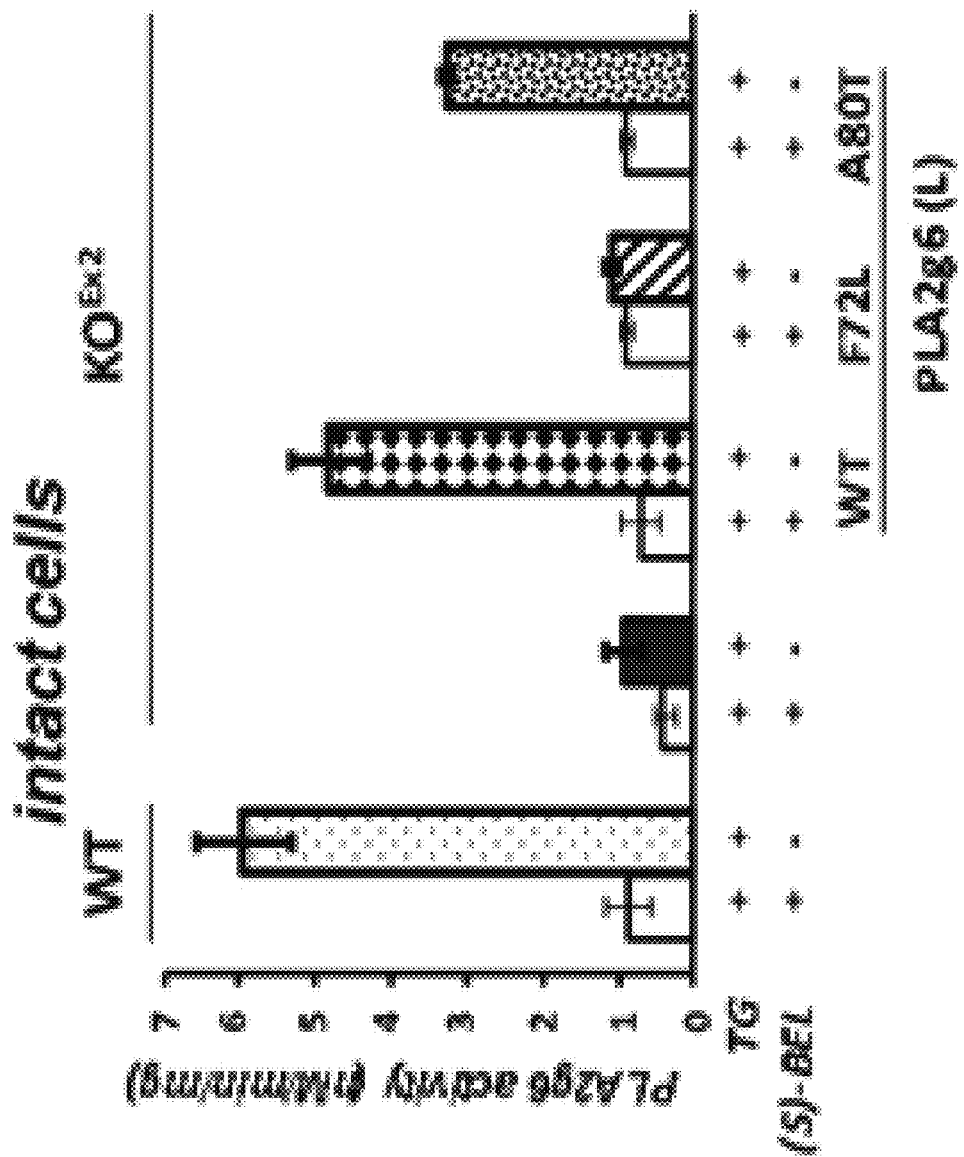
Figure 14N:
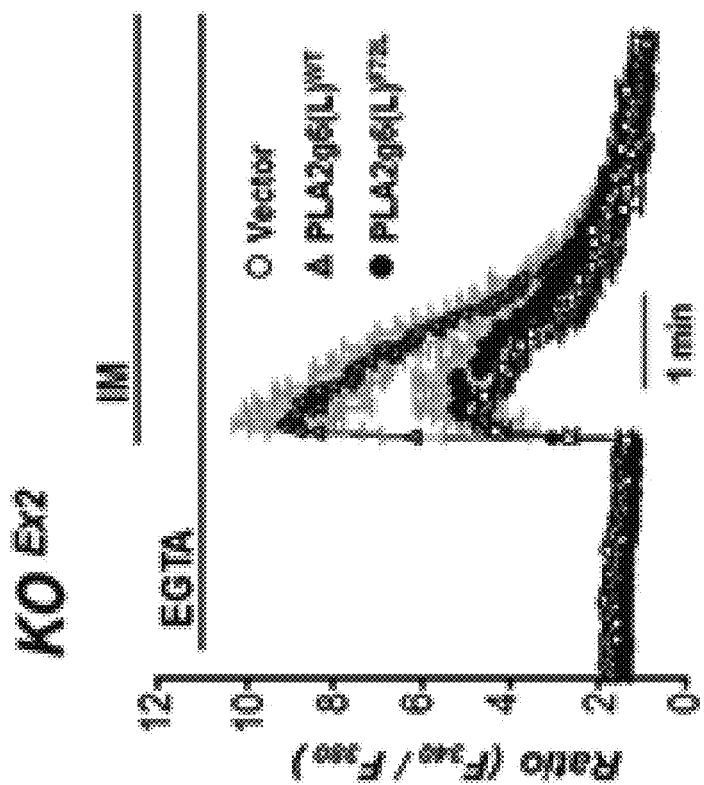
Figure 14M:
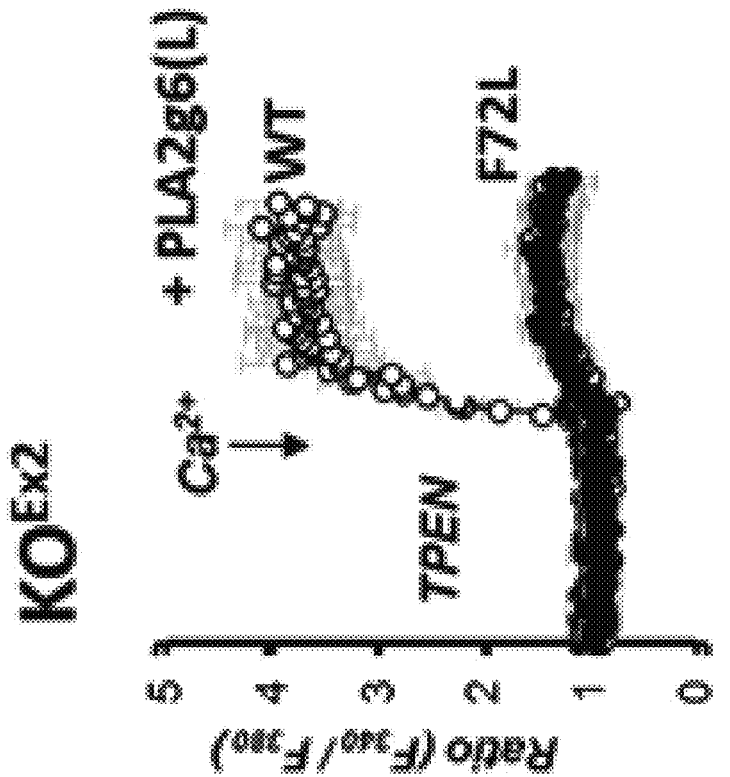

FIGS. 14A to 14N show that genetic deletion of Exon 2 and oblation of N-terminus of PLA2g6 impairs store-operated activation of PLA2g6 (A) and SOCE (B,C,D), and causes depletion of intracellular Ca$^{2+}$ stores (FIG. 14H,I) in KO$^{Ex2}$ MEFs, which can be rescued (E-K) by full length (L), but not (S) variant of PLA2g6. It also shows that human PD mutant (F72L) mimics KO$^{Ex2}$ deficiency in store-operated activation (I), SOCE impairment (FIG. 14M) and depletion of ER Ca stores (N). (A): Comparative analysis of PLA2g6 activity in intact WT and KO$^{Ex2}$ MEFs under basal condition, after TG (5 µM)-induced depletion of the stores in intact cells, and its inhibition by S-BEL (50 µM). (B and C): Store-operated TPEN (400 µM)-induced Ca$^{2+}$ influx in intact WT and KO$^{Ex2}$ MEFs: representative traces show Ca$^{2+}$ responses (average±SEM) in the groups of cells in control, and after pretreatment with S-BEL (50 µM for 20 min). (D): Summary data from experiments shown in B,C. (E): TG-induced PLA2g6 activation in intact KO$^{Ex2}$ MEFs is rescued by expression of PLA2g6(L), but not PLA2g6(S); experiment similar to (a). (F and G): Rescue of TPEN-induced Ca$^{2+}$ influx in KO$^{Ex2}$ MEFs by PLA2g6(L) in experiments similar to (c). (H and I): Comparative analysis of ionomycin (IM, 1 µM)-induced Ca$^{2+}$ release from intracellular stores (in the presence of extracellular EGTA) in WT and KO$^{Ex2}$ MEFs: Ca$^{2+}$ traces (average±SEM) from the groups of cells (h), and (i) summary of the results. (J and K): Rescue of IM-induced Ca$^{2+}$ release in KO$^{Ex2}$ MEFs by PLA2g6(L), but not PLA2g6(S). (L): Store depletion-induced activation of PLA2g6 in intact KO$^{Ex2}$ MEFs can be rescued by WT PLA2g6(L), or non-PD mutant (A80T), but not by F72L mutant that is associated with human PD. (M): SOCE in KO$^{Ex2}$ cells can be rescued by expression of WT PLA2g6(L), but not by F72L mutant. (N): Depleted ER Ca stores in KO$^{Ex2}$ cells can be rescued (refilled) by expression of WT PLA2g6(L), but not by F72L mutant. All summary data in this figure show average±SEM from at least 3 independent experiments per each condition, the number of cells for each condition is specified above the bars, ($p<0.01$), *($p<0.001$).

FIGS. 15A and 15B show an alignment of the human PLA2g6 protein (SEQ ID NO: 1) with the mouse PLA2g6 protein (SEQ ID NO: 2)s. The amino acids are shaded at positions F72, D331, Q452, R632, R635, R741, and R747, and appear to be conserved between the mouse and human sequences. Mutations at these positions have been associated with Parkinson's disease. The point at M179 is shown by the arrow, which identifies the starting point of the N-terminally truncated PLA2g6 protein in KO$^{Ex2}$ mice. This point is only 4 aa away from D183 (shown in bold), which is a natural caspase-3 cleavage site in both, human and mouse PLA2g6.

FIGS. 16A and 16B show various domains of the human PLA2g6 protein (SEQ ID NO: 1).

DETAILED DESCRIPTION

Unless otherwise defined herein, scientific and technical terms used in connection with the present disclosure shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well-known and commonly used in the art. Certain references and other documents cited herein are expressly incorporated herein by reference. Additionally, all Genbank or other sequence database records cited herein are hereby incorporated herein by reference. In case of conflict, the present specification, including definitions, will control. The materials, methods, and examples are illustrative only and not intended to be limiting.

The methods and techniques of the present disclosure are generally performed according to conventional methods well known in the art and as described in various general and more specific references that are cited and discussed throughout the present specification unless otherwise indicated. See, e.g., Sambrook et al., Molecular Cloning: A Laboratory Manual, 3d ed., Cold Spring Harbor Laboratory Press, Cold Spring Harbor, N.Y. (2001); Ausubel et al., Current Protocols in Molecular Biology, Greene Publishing Associates (1992, and Supplements to 2002); Taylor and Drickamer, Introduction to Glycobiology, Oxford Univ. Press (2003); Worthington Enzyme Manual, Worthington Biochemical Corp., Freehold, N.J.; Handbook of Biochemistry: Section A Proteins, Vol I, CRC Press (1976); Handbook of Biochemistry: Section A Proteins, Vol II, CRC Press (1976); Essentials of Glycobiology, Cold Spring Harbor Laboratory Press (1999).

This disclosure refers to sequence database entries (e.g., Genbank and UniProt records) for certain amino acid and nucleic acid sequences that are published on the internet, as well as other information on the internet. The skilled artisan understands that information on the internet, including sequence database entries, is updated from time to time and that, for example, the reference number used to refer to a particular sequence can change. Where reference is made to a public database of sequence information or other information on the internet, it is understood that such changes can occur and particular embodiments of information on the internet can come and go. Because the skilled artisan can find equivalent information by searching on the internet, a reference to an internet web page address or a sequence database entry evidences the availability and public dissemination of the information in question.

Before the present compositions, methods, and other embodiments are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

The term "comprising" as used herein is synonymous with "including" or "containing", and is inclusive or open-ended and does not exclude additional, unrecited members, elements or method steps.

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe).

As used herein, the term "isolated" refers to a substance or entity that has been (1) separated from at least some of the components with which it was associated when initially produced (whether in nature or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

As used herein, the terms "treat," "treatment," "treating," and "amelioration" refer to therapeutic treatments, wherein the object is to reverse, alleviate, ameliorate, inhibit, slow down and/or stop the progression or severity of a condition associated with a disease or disorder. The terms include reducing or alleviating at least one adverse effect or symptom of a condition, disease or disorder associated with a deficiency in motor function. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The terms "treat," "treatment," "treating," and "amelioration" in reference to a disease also include providing relief from the symptoms or side-effects of the disease (including palliative treatment).

As used herein "activating" means increasing the level of. For example, "activating SOCE in a cell" refers to increasing the level of SOCE in the cell. In some embodiments the starting level of SOCE in the cell may be below the level of detection or may be at least 10%, at least 20%, at least 30%, at least 40%, at least 50%, at least 60%, at least 70%, at least 80%, or at least 90% lower than a physiologically normal level of activity. In some embodiments activation results in a increase in level of at least 10%, at least 20%, at least 30%, at least 40%, at least 50%, at least 60%, at least 70%, at least 80%, or at least 90% or more. In some embodiments "activating" refers to maintenance of a level over time. So for example if in a disease state the level of SOCE would tend to deteriorate and a compound reduces at least one of the degree of and the rate of deterioration of level then the compound may be classified as an activator.

A. PLA2g6 Mutants

The structure of the human Pla2g6 gene and protein are shown in FIG. 6a. The full length protein is translated from a start codon located in exon 2 (identified as $ATG_1$) in FIG. 6a. Deletion of exon 2 results in a loss of $ATG_1$ and as shown in the examples section of this application, this causes a cryptic ATG located in exon 4 (labeled ATG in FIG. 6a) to serve as a translation initiation site in PLA2g6 $KO^{Ex2}$ mice disclosed herein. The PLA2g6 $KO^{Ex2}$ allele thus encodes a PLA2g6 protein that lacks the first 178 amino acids at the N-terminus of PLA2g6, and starts at M179 (as shown in FIG. 15). As shown in the examples this mutant (N terminal truncated) protein retains catalytic activity, but cells homozygous for this mutation display a phenotype of greatly impaired store-operated $Ca^{2+}$ entry (SOCE) and depleted ER Ca stores. Broadly speaking, any PLA2g6 mutant protein that retains catalytic activity but confers impaired store-operated $Ca^{2+}$ entry (SOCE) on a cell or animal that is homozygous for the mutant may be used in the methods of this disclosure, and is called a PLA2g6 mutant allele of this disclosure. This disclosure enables all such mutant alleles by showing that such mutants are possible. That is, by showing that it is possible to create mutants that combine retaining catalytic activity, but conferring on cells or animals homozygous for the mutant a phenotype of greatly impaired store-operated $Ca^{2+}$ entry (SOCE) and depletion of ER Ca stores, this disclosure enables the creation of mutant alleles with structures that vary from the alleles specifically disclosed in the examples. For example, using standard techniques established in the art an artisan can create mutant alleles having a different structure than the allele provided in Example 1. The artisan can then create animals or animal cells heterozygous or homozygous for the new mutant allele in order to determine whether the mutant protein encoded by the mutant allele retains catalytic activity, but cells homozygous for the mutant display a phenotype of greatly impaired store-operated $Ca^{2+}$ entry (SOCE) and/or depletion of ER Ca stores. Broadly speaking, any PLA2g6 mutant protein that retains catalytic activity but confers impaired store-operated $Ca^{2+}$ entry (SOCE) and/or depletion of ER $Ca^{2+}$ stores on a cell or animal that is homozygous for the mutant may be used in the methods of this disclosure. Any modified PLA2g6 gene that encodes such a protein is a PLA2g6 mutant allele of this disclosure. Accordingly, PLA2g6 mutant alleles of this disclosure include constitutive and conditional alleles. Many methods of making conditional alleles are known in the art, including for example the Cre-lox system. One example of such an allele is the Floxed-Ex2 animals and animal cells described in the examples. Such alleles can be turned into a wide variety of constitutive and conditional tissue or cell specific $KO^{Ex2}$ models by using Cre-Lox recombination techniques, and thus are included into definition of $KO^{Ex2}$ alleles of this disclosure.

Therefore, a mutant Pla2g6 protein comprises at least one amino acid change (addition, deletion, and/or substitution) relative to a wild type reference PLA2g6 protein. In some embodiments the mutant Pla2g6 protein is at least 70% identical, at least 75% identical, at least 80% identical, at least 90% identical, at least 95% identical, at least 96% identical, at least 97% identical, at least 98% identical, or at least 99% identical to a wild type reference PLA2g6 protein over its whole length or over at least 10 amino acids, at least 20 amino acids, at least 30 amino acids, at least 40 amino acids, at least 50 amino acids, or more. In some embodiments the mutant Pla2g6 protein comprises at least one deletion of at least 5, at least 10, at least 15, at least 20, at least 25, at least 30, at least 40, at least 50, at least 60, at least 70, at least 80, at least 90, at least 100, at least 110, at least 120, at least 130, at least 140, at least 150, at least 160, at least 170, at least 180, at least 190, or at least 200 amino acids at the N-terminus of the Pla2g6 protein. In some embodiments the N-terminal deletion begins at the N-terminal ATG of the wild type Pla2g6 protein while in other embodiments the N-terminus of the deletion is downstream of the N-terminal ATG.

FIGS. 15A and 15B align the human and mouse PLA2g6 proteins. As can be seen in FIG. 6A, the N-terminus of the protein forms a preAnk domain that extends from amino acids 1 to 151 in the human protein. As can be seen in FIG. 15A, the amino acids at the carboxy end of the preAnk domain are conserved in mouse and human. In some embodiments a mutant PLA2g6 protein is a protein that lacks an N-terminal preAnk domain. An Ankyrin repeat domain is located downstream of the preAnk domain of the wild type protein. In some embodiments a mutant PLA2g6 protein is a protein that lacks at least one Ankyrin repeat. The Ankyrin repeat domain is followed by a PIN domain. In some embodiments a mutant PLA2g6 protein is a protein that lacks a PIN domain. In some embodiments a mutant PLA2g6 protein is a protein that comprises at least one addition, deletion, and/or substitution of at least 1, 2, 3, 4, 5, 6, 7, 8, 9, 10 or more amino acids in at least one of these domains. In some embodiments a mutant PLA2g6 protein is a protein comprising a deletion of from 5 to 10, from 10 to 20, from 20 to 30, from 30 to 40, from 40 to 50, from 50 to 60, from 60 to 70, from 70 to 80, from 80 to 90, from 90 to 100, from 100 to 110, from 110 to 120, from 120 to 130, from 130 to 140, from 140 to 150, from 150 to 160, from 160 to 170, from 170 to 180, from 180 to 190, from 190 to 200, from 10 to 50, from 50 to 100, from 100 to 150, or from 150 to 200 amino acids from the N-terminus of the PLA2g6 protein.

Cells comprising a PLA2g6 mutant protein that retains catalytic activity but has an impaired store-operated $Ca^{2+}$ entry (SOCE) provide a tool for identification of additional PLA2g6 mutants that display a similar phenotype. Accordingly, cells can be created comprising one or two copies of the PLA2g6 $KO^{Ex2}$ mutant allele and used to screen for additional mutations in PLA2g6 that display a similar phenotype. Moreover, cells can be created comprising one or two copies of any PLA2g6 mutant allele that confers a similar phenotype and used to screen for additional mutations in PLA2g6 that display a similar phenotype. For example if the cell is heterozygous for the PLA2g6 $KO^{Ex2}$ mutant allele the cell can be mutagenized and the cell or its progeny screened to identify additional mutant alleles. Alternatively, if the cell is homozygous for the PLA2g6 $KO^{Ex2}$ mutant allele it can be transfected with a vector or vector library that comprises nucleic acid sequences encoding modified PLA2g6 sequences to identify sequences that confer a phenotype similar to that seen in cells that are homozygous for the PLA2g6 $KO^{Ex2}$ mutant allele. In some embodiments the cell in in vivo and the screening is done in the context of the whole organism. Skilled artisans will appreciate that based on the teachings of this disclosure several alternative approaches are available to identify mutations in PLA2g6 that give rise to a PLA2g6 mutant protein that retains catalytic activity but has impaired activation by depletion of the stores, resulting in impaired store-operated $Ca^{2+}$ entry (SOCE) pathway activity.

The following mutations in human PLA2g6 have been associated with Parkinson's Disease: F72L, D331Y, Q452X, R632W, R635Q, R741Q, and R747W. As shown in FIGS. 15A and 15B, the amino acids at each of those positions are conserved in the mouse PLA2g6 protein. Thus, in some embodiments a PLA2g6 mutant protein is a human protein that comprises at least one mutation selected from an addition, deletion, and/or substitution at a position selected from F72, D331, Q452, R632, R635, R741, and R747. In some embodiments the mutant protein is a non-human protein that comprises at least one mutation selected from an addition, deletion, and/or substitution at a position homologous to a position selected from F72, D331, Q452, R632, R635, R741, and R747 of the human protein. In some embodiments the mutant protein is a mouse protein that comprises at least one mutation selected from an addition, deletion, and/or substitution at a position homologous to a position selected from F72, D331, Q452, R632, R635, R741, and R747 of the human protein.

In some embodiments a PLA2g6 mutant protein is a human protein that comprises at least one substitution at a position selected from F72, D331, Q452, R632, R635, R741, and R747. In some embodiments the at least one substitution is selected from F72L, D331Y, Q452X, R632W, R635Q, R741Q, and R747W.

In some embodiments the mutant protein is a non-human protein that comprises at least one substitution at a position homologous to a position selected from F72, D331, Q452, R632, R635, R741, and R747 of the human protein. In some embodiments the at least one substitution is selected from F72L, D331Y, Q452X, R632W, R635Q, R741Q, and R747W.

In some embodiments the mutant protein is a mouse protein that comprises at least one substitution at a position homologous to a position selected from F72, D331, Q452, R632, R635, R741, and R747 of the human protein. In some embodiments the at least one substitution is selected from F72L, D331Y, Q452X, R632W, R635Q, R741Q, and R747W. This disclosure also provides nucleic acid sequences that encode a PLA2g6 mutant protein of this disclosure and fragments and homologues thereof. In some embodiments the nucleic is operably linked to an expression control sequence. In some embodiments the nucleic acid is in a vector and comprises the nucleic acid sequence.

This disclosure also provides a cell comprising a nucleic acid sequence that encodes a PLA2g6 mutant protein of this disclosure or a fragment or homologue thereof. In some embodiments the nucleic is operably linked to an expression control sequence. In some embodiments the nucleic acid is in a vector and comprises the nucleic acid sequence.

B. Genetically Modified Animals

Genetically modified animals comprising a mutant allele of PLA2g6 that encodes a mutant PLA2g6 protein wherein store-operated $Ca^{2+}$ entry (SOCE) is impaired in the genetically modified animal may be any animal that comprises a PLA2g6 homologue. In some embodiments the animal is heterozygous for at least one mutant PLA2g6 allele of this disclosure. In some embodiments the animal is homozygous for mutant PLA2g6 allele of this disclosure. In some embodiments the animal comprises at least one conditional mutant PLA2g6 allele of this disclosure, which may be a conditional allele that has been recombined to delete a portion of the PLA2g6 gene or an allele that has not been so recombined but is capable of such recombination. For example, the genetically modified animal can be a mammal, such as a rodent (e.g., mouse, rat), a horse, a cow, a sheep, a pig, a non-human primate, or a human. The genetically modified animal can also be a fish (such as a zebra fish), a *Drosophila*, or a nematode worm. Techniques are well known in each of these systems for generation of random and/or targeted mutations in genes and skilled artisans can use the teachings of this disclosure to create genetically modified animals comprising a mutant allele of PLA2g6 that encodes a mutant PLA2g6 protein comprising an impaired store-operated Ca2+ entry (SOCE) pathway activity and depletion of ER $Ca^{2+}$ stores.

In some embodiments the genetically modified animal comprises one mutant allele of PLA2g6 that encodes a mutant PLA2g6 protein, wherein the mutant allele when homozygous confers on a homozygous animal an impairment of SOCE. In some embodiments the genetically modified animal comprises two mutant alleles of PLA2g6 and SOCE is impaired in the genetically modified animal. In some embodiments the two mutant alleles of PLA2g6 are the same allele while in other embodiments the alleles are different, meaning that the alleles comprise different nucleotide sequences and/or comprise different regulatory sequences that cause a difference in their expression.

C. Genetically Modified Animal Cells

Genetically modified animal cells comprising a mutant allele of PLA2g6 that encodes a mutant PLA2g6 protein wherein store-operated $Ca^{2+}$ entry (SOCE) is impaired in the genetically modified animal cell may be any cell type of any animal that comprises a PLA2g6 homologue. For example, the genetically modified animal cell can be a mammal cell, such as a rodent (e.g., mouse, rat), a horse, a cow, a sheep, a pig, a non-human primate, or a human cell. The genetically modified animal cell can also be a fish (such as a zebra fish), a *Drosophila*, or a nematode worm cell. The genetically modified animal cell can be an in vivo or in vitro cell. Techniques are well known in each of these systems for generation of random and/or targeted mutations in genes and skilled artisans can use the teachings of this disclosure to create genetically modified animals comprising a mutant allele of PLA2g6 that encodes a mutant PLA2g6 protein comprising an impaired store-operated $Ca^{2+}$ entry (SOCE) pathway activity In some embodiments the genetically modified animal cell is a pluripotent cell such as a stem cell (e.g., embryonic stem cell or induced pluripotent stem cell) or a neural precursor cell. In some embodiments the genetically modified animal cell is made by first making a genetically modified pluripotent cell and then differentiating the genetically modified animal cell into a different cell type. In some embodiments the genetically modified cell is a cell line, such as a 3T2 fibroblast or an established embryonic stem cell line. In other embodiments the genetically modified animal cell is a primary cell. In some embodiments the genetically modified animal cell is a cell that is obtained from a genetically modified animal. For example, a genetically modified mouse comprising a mutant allele of PLA2g6 that encodes a mutant PLA2g6 protein can be used as a source of isolated genetically modified mouse cells comprising a mutant allele of PLA2g6.

In some embodiments the genetically modified animal cell is a neural cell such as a neuron or a glial cell. In some embodiments the genetically modified animal cell is a dopaminergic neuron. In some embodiments the genetically modified animal cell is a non-neural cell. In some embodiments the genetically modified animal cell is a macrophage, smooth muscle cell, pancreatic beta cell, platelet, or lymphocyte.

In some embodiments the genetically modified animal cell comprises one mutant allele of PLA2g6 that encodes a mutant PLA2g6 protein, wherein the mutant allele when homozygous confers on a homozygous animal an impairment of SOCE. In some embodiments the genetically modified animal cell comprises two mutant alleles of PLA2g6 and SOCE is impaired in the genetically modified animal. In some embodiments the two mutant alleles of PLA2g6 are the same allele while in other embodiments the alleles are different, meaning that the alleles comprise different nucleotide sequences and/or comprise different regulatory sequences that cause a difference in their expression.

D. Screening Methods

The genetically modified animals and animal cells provided herein that comprise a mutant allele of PLA2g6 can be used in screening methods and systems to identify compounds that modulate the SOCE pathway. Broadly speaking the methods comprise providing a test compound to a genetically modified animal or animal cell comprising a mutant allele of PLA2g6, wherein store-operated $Ca^{2+}$ entry (SOCE) is impaired in the genetically modified animal or animal cell; and determining the effect of the compound on SOCE pathway activation and ER $Ca^{2+}$ in the animal or animal cell. The effect of a compound on SOCE pathway activation in an animal may be determined by removing at least one cell from the animal and then determining SOCE pathway activity in the cell for example. In some embodiments the animal or animal cell comprises two mutant alleles of PLA2g6. In such embodiments the assay may comprise measuring at least one feature of SOCE to determine if it is rescued (increased) in the presence of the compound. If so, the compound is identified as a SOCE activator. In some embodiments the animal cell used in the method comprises one mutant allele of PLA2g6. In such embodiments the assay may comprise measuring at least one feature of SOCE to determine if it is decreased in the presence of the compound. If so, the compound is identified as a SOCE inhibitor.

In some embodiments of the methods the mutant PLA2g6 protein(s) encoded by the mutant allele(s) in the animals or animal cells used in the methods retain a substantially wild-type catalytic activity. In some embodiments of the methods SOCE pathway activation by depletion of endoplasmic reticulum (ER) $Ca^{2+}$ stores is impaired in the genetically modified animal or animal cell.

In some embodiments the methods comprise providing a test compound to a genetically modified animal or animal cell comprising a mutant allele of PLA2g6 wherein store-operated $Ca^{2+}$ entry (SOCE) is impaired in the genetically modified animal or animal cell; and determining the effect of the compound on SOCE in the animal cell. In some embodiments the animal or animal cell comprises two mutant alleles of PLA2g6. In such embodiments the assay may comprise measuring at least one feature of SOCE or ER $Ca^{2+}$ to determine if it is rescued (or increased) in the presence of the compound. If so, the compound is identified as a SOCE activator. In some embodiments the animal or animal cell used in the method comprises one mutant allele of PLA2g6. In such embodiments the assay may comprise measuring at least one feature of SOCE or ER $Ca^{2+}$ to determine if it is decreased in the presence of the compound. If so, the compound is identified as a SOCE inhibitor.

In some embodiments of the methods the mutant PLA2g6 protein(s) encoded by the mutant allele(s) in the animal or animal cell used in the methods retain a substantially wild-type catalytic activity. In some embodiments of the methods SOCE pathway activation by depletion of endoplasmic reticulum (ER) $Ca^{2+}$ stores is impaired in the genetically modified animal cell.

In embodiments of the methods that utilize a genetically modified animal the methods may further comprise assessing at least one parameter associated with PD-related deficit in an animal. The phenotype may be assessed by measuring the number of dopaminergic neurons in the animal, or by using at least one method to measure the health or function of dopaminergic neurons in the animal, or by using at least one method to measure motor function of the animal (e.g., by using any of the in vivo techniques known in the art for this purpose). For example, a region of the animal's central nervous system that contains dopaminergic neurons may be stained for a marker of dopaminergic neurons, such as tyrosine hydroxylase, and the number of dopaminergic neurons may be quantified to determine whether there is a difference between the genetically modified animal that received the test compound and a control that did not. Another example can be analysis of morphology or different parameters of cellular function in dopaminergic neurons (mitochondrial function, oxidative stress, autophagy, or any other parameter of cellular function) to determine whether there is a difference between the genetically modified animal that received the test compound and a control that did not. Another example is the results of the rotarod test or balance beam test, or any other test that can detect impaired motor function in live animals.

In some embodiments the methods comprise providing a test compound to a genetically modified animal comprising a mutant allele of PLA2g6 wherein store-operated $Ca^{2+}$ entry (SOCE) is impaired, or ER $Ca^{2+}$ is depleted in the genetically modified animal; and determining the effect of the compound on dopaminergic neurons in the animal. In some embodiments the animal comprises two mutant alleles of PLA2g6 and store-operated $Ca^{2+}$ entry (SOCE) is impaired in the genetically modified animal. In such embodiments the assay may comprise measuring at least one feature of dopaminergic neuron function to determine if it is improved in the presence of the compound. If so, the compound is identified as a PD-preventer. In some embodiments the animal used in the method comprises two WT, or one mutant allele of PLA2g6. In such embodiments the assay may comprise measuring at least one feature of dopaminergic neuron function to determine if its function is impaired in the presence of the compound. If so, the compound is identified as a PD enhancer.

In some embodiments of the methods the mutant PLA2g6 protein(s) encoded by the mutant allele(s) in the animal(s) used in the methods retain a substantially wild-type catalytic activity. In some embodiments of the methods SOCE pathway activation by depletion of endoplasmic reticulum (ER) $Ca^{2+}$ stores is impaired in the genetically modified animal cell.

Test compounds that may be characterized by the methods include any substance, including without limitation a peptide, a polypeptide, a protein (such as for example an antibody or antibody fragment), a nucleotide, an oligonucleotide, a polynucleotide, a lipid, a sugar, or a naturally occurring or non-naturally occurring derivative of any such substances or small molecules. The test compounds, whether also fitting within one or more of the previously listed classes, may be a small organic molecule or a complex organic molecule.

Generally, though not necessarily, compounds are tested at several different concentrations and administered one or more times to optimize the chances that SOCE pathway modulation will be detected and recognized if present. Typically assays are performed in triplicate, for example, and vary within experimental error by less than about 15%. Each experiment is typically repeated about three or more times with similar results.

E. Uses of SOCE Activators

Compounds that activate SOCE are useful, for example, to activate SOCE and refill depleted ER Ca stores in an animal or an in vitro animal cell. Because impaired SOCE activation is found to be a feature of conditions (such as PD) that are characterized by age-dependent motor deficit in an animal, the compounds are for example useful for treating or preventing PD-related deficit(s) in an animal. Accordingly, compounds identified as activators of SOCE using the methods of this disclosure may be used for treating or preventing PD-related deficit(s) in an animal. For example, in some embodiments such treatment methods comprise treating or preventing PD-related deficit(s) in an animal by a method comprising: a) characterizing a compound as a SOCE activator by a method of this disclosure; and b) administering an effective amount of the compound to the animal to thereby treat or prevent the PD-related deficit(s) in the animal. Accordingly, this disclosure provides methods of treating or preventing PD-related deficit(s) in an animal. In some embodiments the animal is a human and deficit is Parkinson's disease.

Pharmaceutical compositions for use in the methods of treatment herein are formulated to contain therapeutically effective amounts of at least one SOCE activator. The pharmaceutical compositions are useful, for example, in the treatment of at least one PD-related deficit(s) in an animal.

In some embodiments, the at least one SOCE activator is formulated into a suitable pharmaceutical preparation such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the SOCE activator described above is formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more SOCE activators or pharmaceutically acceptable derivatives is (are) mixed with a suitable pharmaceutical carrier or vehicle.

Pharmaceutically acceptable derivatives include acids, bases, enol ethers and esters, salts, esters, hydrates, solvates and prodrug foul's. The derivative is selected such that its pharmacokinetic properties are superior with respect to at least one characteristic to the corresponding neutral agent. The SOCE activator may be derivatized prior to formulation.

The concentrations of the SOCE activators in the compositions are effective for delivery of an amount, upon administration, that treats one or more of the symptoms of at least one disease state characterized by PD-related deficit(s) in an animal, for example.

Typically, by way of example and without limitation, the compositions are formulated for single dosage administration. To formulate a composition, the weight fraction of SOCE activator is dissolved, suspended, dispersed or otherwise mixed in a selected vehicle at an effective concentration such that the treated condition is relieved or ameliorated. Pharmaceutical carriers or vehicles suitable for administration of the SOCE activator include any such carriers known to those skilled in the art to be suitable for the particular mode of administration.

In addition, the SOCE activator may be formulated as the sole active agent in the composition or may be combined with other active agents. Liposomal suspensions, including tissue-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a SOCE activator provided herein in phosphate buffered saline lacking divalent cations (PBS) is added and the flask shaken until the lipid film is dispersed. The resulting vesicles are washed to remove unencapsulated SOCE activator, pelleted by centrifugation, and then resuspended in PBS.

The active SOCE activator is included in the pharmaceutically acceptable carrier in an amount sufficient to exert a therapeutically useful effect in the absence of undesirable side effects on the patient treated. The therapeutically effective concentration may be determined empirically by testing the agents in in vitro and in vivo systems described herein and in International Patent Application Publication Nos. 99/27365 and 00/25134 and then extrapolated there from for dosages for humans.

The concentration of active SOCE activator in the pharmaceutical composition will depend on absorption, inactivation and excretion rates of the active agent, the physicochemical characteristics of the agent, the dosage schedule, and amount administered as well as other factors known to those of skill in the art. For example, the amount that is delivered is sufficient to treat at least one disease state characterized by at least one age-dependent motor deficit, as described herein.

Typically a therapeutically effective dosage should produce a serum concentration of active agent of from about 0.1 ng/ml to about 50-100 µg/ml, for example. The pharmaceutical compositions typically should provide a dosage of from about 0.001 mg to about 2000 mg of SOCE activator per kilogram of body weight per day, such as from about 0.01 mg to about 200 mg of SOCE activator per kilogram of body weight per day, or from about 0.1 mg to about 20 mg of SOCE activator per kilogram of body weight per day, or from about 1 mg to about 10 mg of SOCE activator per kilogram of body weight per day, or from about 1 mg to about 5 mg of SOCE activator per kilogram of body weight per day. Pharmaceutical dosage unit forms are prepared to provide from about 1 mg to about 1000 mg, such as from about 10 to about 500 mg of the active agent or a combination of agents per dosage unit form.

The active agent may be administered at once, or may be divided into a number of smaller doses to be administered at intervals of time. It is understood that the precise dosage and duration of treatment is a function of the disease state being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed methods.

Thus, effective concentrations or amounts of one or more SOCE activator or pharmaceutically acceptable derivatives thereof are mixed with a suitable pharmaceutical carrier or vehicle for systemic, topical or local administration to form pharmaceutical compositions. SOCE activators are included in an amount effective for treating at least one disease state characterized by age-dependent motor deficit. The concentration of active agent in the composition will depend on absorption, inactivation, excretion rates of the active agent, the dosage schedule, amount administered, particular formulation as well as other factors known to those of skill in the art.

The compositions are intended to be administered by a suitable route, including by way of example and without limitation orally, parenterally, rectally, topically and locally. For oral administration, capsules and tablets can be used. The compositions are in liquid, semi-liquid or solid foul and are formulated in a manner suitable for each route of administration.

Solutions or suspensions used for parenteral, intradermal, subcutaneous, or topical application can include any of the following components, in any combination: a sterile diluent, including by way of example without limitation, water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampoules, disposable syringes or single or multiple dose vials made of glass, plastic or other suitable material.

In instances in which the agents exhibit insufficient solubility, methods for solubilizing agents may be used. Such methods are known to those of skill in this art, and include, but are not limited to, using co-solvents, such as dimethylsulfoxide (DMSO), using surfactants, such as TWEEN®, or dissolution in aqueous sodium bicarbonate. Pharmaceutically acceptable derivatives of the agents may also be used in formulating effective pharmaceutical compositions.

Upon mixing or addition of the agent(s), the resulting mixture may be a solution, suspension, emulsion or the like. The form of the resulting mixture depends upon a number of factors, including the intended mode of administration and the solubility of the agent in the selected carrier or vehicle. The effective concentration is sufficient for treating one or more symptoms of at least one disease state characterized by reduced platelet count and/or function and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the agents or pharmaceutically acceptable derivatives thereof. The pharmaceutically therapeutically active agents and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active agent sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain along with the active agent, for example and without limitation: a diluent such as lactose, sucrose, dicalcium phosphate, or carboxymethylcellulose; a lubricant, such as magnesium stearate, calcium stearate and talc; and a binder such as starch, natural gums, such as gum acacia gelatin, glucose, molasses, polyvinylpyrrolidone, celluloses and derivatives thereof, povidone, crospovidones and other such binders known to those of skill in the art. Liquid pharmaceutically administrable compositions can, for example, be prepared by dissolving, dispersing, or otherwise mixing an active agent as defined above and optional pharmaceutical adjuvants in a carrier, such as, by way of example and without limitation, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, such as, by way of example and without limitation, acetate, sodium citrate, cyclodextrin derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active agent in an amount sufficient to alleviate the symptoms of the treated subject.

Dosage forms or compositions containing active agent in the range of 0.005% to 100% with the balance made up from non-toxic carrier may be prepared. For oral administration, a pharmaceutically acceptable non-toxic composition is formed by the incorporation of any of the normally employed excipients, such as, for example and without limitation, pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%-100% active agent, such as 0.1-85%, or such as 75-95%.

The active agents or pharmaceutically acceptable derivatives may be prepared with carriers that protect the agent against rapid elimination from the body, such as time release formulations or coatings. The compositions may include other active agents to obtain desired combinations of properties. SOCE activators or pharmaceutically acceptable derivatives thereof, may also be advantageously administered for therapeutic or prophylactic purposes together with another pharmacological agent known in the general art to be of value in treating at least one disease state characterized by reduced platelet counts and/or function.

Oral pharmaceutical dosage forms include, by way of example and without limitation, solid, gel and liquid. Solid dosage forms include tablets, capsules, granules, and bulk powders. Oral tablets include compressed, chewable lozenges and tablets which may be enteric-coated, sugar-coated or film-coated. Capsules may be hard or soft gelatin capsules, while granules and powders may be provided in non-effervescent or effervescent forms with the combination of other ingredients known to those skilled in the art.

In some embodiments, the formulations are solid dosage forms, such as capsules or tablets. The tablets, pills, capsules, troches and the like can contain any of the following ingredients, or agents of a similar nature: a binder; a diluent; a disintegrating agent; a lubricant; a glidant; a sweetening agent; and a flavoring agent.

Examples of binders include, by way of example and without limitation, microcrystalline cellulose, gum tragacanth, glucose solution, acacia mucilage, gelatin solution, sucrose, and starch paste. Lubricants include, by way of example and without limitation, talc, starch, magnesium or calcium stearate, lycopodium and stearic acid. Diluents include, by way of example and without limitation, lactose, sucrose, starch, kaolin, salt, mannitol, and dicalcium phosphate. Glidants include, by way of example and without limitation, colloidal silicon dioxide. Disintegrating agents include, by way of example and without limitation, crosscarmellose sodium, sodium starch glycolate, alginic acid, corn starch, potato starch, bentonite, methylcellulose, agar and carboxymethylcellulose. Coloring agents include, by way of example and without limitation, any of the approved certified water soluble F1) and C dyes, mixtures thereof; and water insoluble ID and C dyes suspended on alumina hydrate. Sweetening agents include, by way of example and without limitation, sucrose, lactose, mannitol and artificial sweetening agents such as saccharin, and any number of spray dried flavors. Flavoring agents include, by way of example and without limitation, natural flavors extracted from plants such as fruits and synthetic blends of agents which produce a pleasant sensation, such as, but not limited to peppermint and methyl salicylate. Wetting agents include, by way of example and without limitation, propylene glycol monostearate, sorbitan monooleate, diethylene glycol monolaurate, and polyoxyethylene laural ether. Emetic-coatings include, by way of example and without limitation, fatty acids, fats, waxes, shellac, ammoniated shellac and cellulose acetate phthalates. Film coatings include, by way of example and without limitation, hydroxyethylcellulose, sodium carboxymethylcellulose, polyethylene glycol 4000 and cellulose acetate phthalate.

If oral administration is desired, the agent could be provided in a composition that protects it from the acidic environment of the stomach. For example, the composition can be formulated in an enteric coating that maintains its integrity in the stomach and releases the active agent in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The agents can also be administered as a component of an elixir, suspension, syrup, wafer, sprinkle, chewing gum or the like. A syrup may contain, in addition to the active agents, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents may be used in any of the above dosage forms.

Solvents, include by way of example and without limitation, glycerin, sorbitol, ethyl alcohol and syrup. Examples of preservatives include without limitation glycerin, methyl and propylparaben, benzoic add, sodium benzoate and alcohol. Non-aqueous liquids utilized in emulsions, include by way of example and without limitation, mineral oil and cottonseed oil. Emulsifying agents, include by way of example and without limitation, gelatin, acacia, tragacanth, bentonite, and surfactants such as polyoxyethylene sorbitan monooleate. Suspending agents include, by way of example and without limitation, sodium carboxymethylcellulose, pectin, tragacanth, Veegum and acacia. Diluents include, by way of example and without limitation, lactose and sucrose. Sweetening agents include, by way of example and without limitation, sucrose, syrups, glycerin and artificial sweetening agents such as saccharin. Wetting agents, include by way of example and without limitation, propylene glycol monostearate, sorbitan monooleate, diethylene glycol monolaurate, and polyoxyethylene lauryl ether. Organic acids include, by way of example and without limitation, citric and tartaric acid. Sources of carbon dioxide include, by way of example and without limitation, sodium bicarbonate and sodium carbonate. Coloring agents include, by way of example and without limitation, any of the approved certified water soluble FD and C dyes, and mixtures thereof. Flavoring agents include, by way of example and without limitation, natural flavors extracted from plants such fruits, and synthetic blends of agents which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, for example in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active agent or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603. Briefly, such formulations include, but are not limited to, those containing an agent provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Tablets and capsules formulations may be coated as known by those of skill in the art in order to modify or sustain dissolution of the active ingredient. Thus, for example and without limitation, they may be coated with a conventional enterically digestible coating, such as phenylsalicylate, waxes and cellulose acetate phthalate.

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients, include by way of example and without limitation, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a AhR modulator is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The agent diffuses through the outer polymeric membrane in a release rate controlling step. The percentage of active agent contained in such parenteral compositions is highly dependent on the specific nature thereof, as well as the activity of the agent and the needs of the subject.

Parenteral administration of the SOCE activators includes and not limited to intravenous, subcutaneous, intramuscular, intracranial and other ways of administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Aqueous vehicles include, by way of example and without limitation, Sodium Chloride Injection, Ringers Injection, Isotonic Dextrose Injection, Sterile Water Injection, Dextrose and Lactated Ringers Injection. Nonaqueous parenteral vehicles include, by way of example and without limitation, fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include, by way of example and without limitation, sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include, by way of example and without limitation, ethyl alcohol, polyethylene glycol and propylene glycol for water miscible vehicles and sodium hydroxide, hydrochloric acid, citric acid or lactic acid for pH adjustment.

The concentration of the pharmaceutically active agent is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. Preparations for parenteral administration should be sterile, as is known and practiced in the art.

Illustratively, intravenous or intraarterial infusion of a sterile aqueous solution containing an active agent is an effective mode of administration. Another embodiment is a sterile aqueous or oily solution or suspension containing an active agent injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of the active agent to the treated tissue(s). The active agent may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The agent may be suspended in micronized or other suitable form or may be derivatized, e.g., to produce a more soluble active product or to produce a prodrug or other pharmaceutically acceptable derivative. The form of the resulting mixture depends upon a number of factors, including the intended mode of administration and the solubility of the agent in the selected carrier or vehicle. The effective concentration is sufficient for ameliorating the symptoms of the condition and may be empirically determined.

Lyophilized powders can be reconstituted for administration as solutions, emulsions, and other mixtures or formulated as solids or gels.

The sterile, lyophilized powder is prepared by dissolving an agent provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain, by way of example and without limitation, a single dosage (10-1000 mg, such as 100-500 mg) or multiple dosages of the agent. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, such as about 5-35 mg, for example, about 9-30 mg of lyophilized powder, is added per mL of sterile water or other suitable carrier. The precise amount depends upon the selected agent. Such amount can be empirically determined.

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The agents or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microtine powder for insufflation, alone or in combination with an inert carrier such as lactose. In such a case, the particles of the formulation will, by way of example and without limitation, have diameters of less than about 50 microns, such as less than about 10 microns.

The agents may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active agent alone or in combination with other pharmaceutically acceptable excipients can also be administered.

These solutions, particularly those intended for ophthalmic use, may be formulated, by way of example and without limitation, as about 0.01% to about 10% isotonic solutions, pH about 5-7, with appropriate salts.

Other routes of administration, such as transdermal patches, and rectal administration are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957.

Pharmaceutical dosage thin's for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is, by way of example and without limitation, about 2 to 3 gm.

Tablets and capsules for rectal administration are manufactured using the same pharmaceutically acceptable substance and by the same methods as for formulations for oral administration.

The SOCE activators, or pharmaceutically acceptable derivatives thereof, may also be formulated to be targeted to a particular tissue, receptor, or other area of the body including brain of the subject to be treated. Many such targeting methods are well known to those of skill in the art. Such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In some embodiments, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of an agent provided herein in phosphate buffered saline lacking divalent cations (PBS) is added and the flask shaken until the lipid film is dispersed. The resulting vesicles are washed to remove unencapsulated agent, pelleted by centrifugation, and then resuspended in PBS.

The SOCE activators or pharmaceutically acceptable derivatives for use in the methods may be packaged as articles of manufacture containing packaging material, a SOCE activator or pharmaceutically acceptable derivative thereof, which is effective for modulating the activity of SOCE or for treatment, of one or more symptoms of at least one disease state characterized by reduced platelet count and/or platelet function within the packaging material, and a label that indicates that the SOCE activator or composition, or pharmaceutically acceptable derivative thereof, is used for modulating the activity of SOCE for treatment of one or more symptoms of at least one disease state characterized by age-dependent motor deficit.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

F. Uses of Modified PLA2g6 Proteins Resistant to Caspase-3 Cleavage

The data presented in Example 3 demonstrate that the plasma membrane-associated (L), but not cytosolic (S) variant of PLA2g6 is involved in SOCE and ER $Ca^{2+}$ refilling, and impairment of signal transduction from STIM1 to PLA2g6(L) results in depletion of intracellular $Ca^{2+}$ stores, which can be associated with the PD-like phenotype in $KO^{Ex2}$ mice. Expression of PLA2g6 (L) is able to rescue the phenotype of homozygous $KO^{Ex2}$ cells. Mechanistically, deletion of the N terminus of PLA2G6(L) that is similar to that achieved genetically in homozygous $KO^{Ex2}$ mice, can also naturally occur through its Caspase3-induced cleavage. FIG. 15 shows close proximity of genetic $KO^{Ex2}$ site of N terminal truncation, and the site of caspase 3 cleavage of PLA2g6 protein. Either of such modification of PLA2g6 protein will result in deletion of N terminus, which will result in an impairment of the signal transduction events by disrupting the ability of PLA2g6(L) to bind STIM1 (Ca sensor in ER membrane). So, similar to genetic truncation of N terminus in $KO^{Ex2}$, Caspase 3 induced cleavage of N terminus of PLA2g6 will impair transduction of STIM1-initiated signal to Orai1 (store-operated plasma membrane channel). As demonstrated in Example 3, disruption of this PLA2g6-mediated SOCE pathway causes age-dependent death of dopaminergic neurons and development of PD-like phenotype in mutant mice. Thus, PLA2g6-mediated SOCE mechanism appeared to be extremely important for dopaminergic neurons. Since caspase 3 is known to be activated by numerous triggers of PD in humans, its age-dependent activation can lead to cleavage of PLA2g6 and creation of N-terminally truncated PLA2g6 protein that will be uncapable of performing normal SOCE function, leading to impairment of SOCE and pathological consequences for dopaminergic neurons that are described in Example 3. On the basis of these findings and the role of caspase-3 activation in neuropathology of age-dependent PD, it is hypothesized that expression of modified forms of PLA2g6(L) in cells will prevent caspase-3 dependent impairment of SOCE, and treat or prevent pathological cycle of deleterious events leading to age-dependent PD phenotype. For example, modified forms of PLA2g6 that are resistant to caspase-3 cleavage may be introduced into dopaminergic neurons or other cells to provide a source of functional PLA2g6 that will be resistant to caspase-3 cleavage. Such modified forms include forms that comprise a modified caspase-3 cleavage site that is substantially resistant to caspase-3 cleavage. In humans the caspase-3 cleavage site is at D183 (see FIGS. 15 and 16). Accordingly, in some embodiments modified forms of PLA2g6 that are resistant to caspase-3 cleavage comprise at least one addition, subtraction, and/or deletion of at least one amino acid that comprises a change to the caspase-3 cleavage site of the PLA2g6 protein. For example, in human the at least one addition, subtraction, and/or deletion may comprise deletion or substitution of D183. For example, in a non-human animal the at least one addition, subtraction, and/or deletion may comprise deletion or substitution of an amino acid at a position homologous to D183 of the human PLA2g6 protein.

Accordingly, this disclosure also provides methods of treating or preventing PD-related deficit(s) in an animal, comprising administering a caspase-3 cleavage-resistant PLA2g6 protein to dopaminergic neurons of the mammal. Because the modified PLA2g6 proteins are resistant to caspase-3 cleavage the presence of the modified PLA2g6 proteins in the cell renders the SOCE signaling activity of PLA2g6 in the cell at least partially independent of caspase-3 activity, thus preserving at least in part its normal function that supports dopaminergic neuron health and survival.

In some embodiments a modified PLA2g6 proteins resistant to caspase-3 cleavage is administered to the cell directly. However, in other embodiments the modified PLA2g6 protein resistant to caspase-3 cleavage is administered to the cell indirectly, by introducing a nucleic acid encoding the modified PLA2g6 protein into the cell so that the nucleic acid is transcribed and translated in the cell to thereby administer the modified PLA2g6 proteins resistant to caspase-3 cleavage to the cell.

The nucleic acid encoding the modified PLA2g6 protein will typically be administered to the cell operably linked to expression control sequences sufficient for expression in the cell. Often, though not necessarily, this is accomplished by placing the nucleic acid encoding the modified PLA2g6 protein in a vector that further comprises the expression control sequences. Any vector that supports expression of a heterologous nucleic acid in an animal cell may be used.

In some embodiments a viral vector is used in the methods. Suitable viral vectors include recombinant Adeno-Associated virus (rAAV), Lentivirus (LV), Adenovirus (Ad), and Herpes-Simplex virus (HSV).

Recombinant AAV supports a genomic/gene carrying capacity of roughly 6 kb, and the only viral elements remaining in the recombinant virus are the inverted terminal repeats in the distal ends of the genome, structures required for helper mediated replication and capsid packaging. Following infection, rAAV supports transgene expression in post-mitotic cells for the lifetime of the individual. Serotype 2 has been utilized in CNS clinical trials and displayed an excellent safety profile. Recently, a plethora of additional serotypes have been identified from a variety of species. In addition, the mixing of viral genomes of one serotype with capsids from another serotype creating mosaic "pseudotypes" of rAAV have displayed a wide range of neuronal tropisms and efficacies. Many of these "newer" rAAV vectors have displayed greater transduction efficiency and transgene expression than that of rAAV2. Moreover, efforts are underway to selectively alter the processing of the viral capsid as well as random shuffling of portions of the capsid between various serotypes in order to maximize transgene levels and viral distribution. Historically, rAAV has only been a neurotrophic virus in the context of the CNS;

however, with the identification of recent serotypes, as well as the production of higher titer vector preparations, increasing frequency of infection of non-neuronal cell-types of the CNS has been observed. Accordingly, in some embodiments a nucleic acid sequence encoding a modified PLA2g6 proteins resistant to caspase-3 cleavage is introduced into a rAAV vector in functional association with expression regulatory elements and introduced into the CNS of a mammal to treat or prevent PD-related deficit(s) in the mammal. In some embodiments the mammal is a human. In some embodiments the age-dependent motor deficit is PD. In some embodiments the rAAV vector is serotype 2. In some embodiments the rAAV vector is a pseudotyped vector.

Though the use of rAAV results in a very acceptable safety profile, the limited genomic carrying capability may be a limitation for certain indications. Other vectors such as Adenovirus (Ad) (8-30 kb) or HSV (40-150 kb) could be utilized to introduce a larger nucleic acid insert. For example, Ad has been utilized in CNS clinical trials targeting brain tumors. Two types of Ad viral vectors have been extensively used. First generation Ad, based on Ad type 5, has the early genes E1a and E1b removed. Next generation Ad vectors, referred to as "gutless" or "high-capacity" Ad have all of the viral genome removed, resulting in greater transgene capacity. Ad displays a rather promiscuous tropism when targeted to the CNS, infecting neurons and glial cells equally. However, the large carrying capacity allows for the use of cell-specific promoters, thus allowing for cell-specific expression of transgene(s). Accordingly, in some embodiments a nucleic acid sequence encoding a modified PLA2g6 proteins resistant to caspase-3 cleavage is introduced into an Ad vector in functional association with expression regulatory elements and introduced into the CNS of a mammal to treat or prevent PD-related deficit(s) in the mammal. In some embodiments the mammal is a human. In some embodiments the age-dependent motor deficit is PD.

Wild type HSV is a naturally neurotrophic virus with a very large (152 kb) genome. HSV vectors based on HSV type 1 exist in two forms: recombinant vectors and amplicons. Recombinant vectors retain some of the normally very large HSV genome. Amplicon vectors which contain a minimal portion of the HSV DNA genome, are replication deficient, and require helper functions for production. Developments in production methods now allow for the production of high titer vectors which are devoid of helper DNA. Clinical trials involving HSV have involved the over-expression of preproenkephalin A in dorsal root ganglia in order to treat chronic pain. Accordingly, in some embodiments a nucleic acid sequence encoding a modified PLA2g6 protein resistant to caspase-3 cleavage is introduced into a HSV vector in functional association with expression regulatory elements and introduced into the CNS of a mammal to treat or prevent PD-related deficit(s) in the mammal. In some embodiments the mammal is a human. In some embodiments the age-dependent motor deficit is PD.

Lentivirus (Lv) belongs to a subclass of retroviruses that integrate into the host cell genome. Early Lv vectors, based largely on human immunodeficiency virus 1 (HIV-1), include components of the HIV genome, but most of these elements have been removed in the newest generations. Recently developed vectors lack integrase. The resulting non-integrating lentiviral vectors (NIL) have been shown to lead to extra-genomic vector DNA being maintained either in a circular or linear fashion. Due to its natural ability to integrate, LV has been extensively utilized for ex vivo gene transfer, especially considering the strong tropism for neural stem and progenitor cells, effectively rendering the cell-line transgenic, allowing for transplantation and over-expression of the therapeutic gene. Lv shows a lot of promise in CNS applications. Accordingly, in some embodiments a nucleic acid sequence encoding a modified PLA2g6 proteins resistant to caspase-3 cleavage is introduced into a Lv vector in functional association with expression regulatory elements and introduced into the CNS of a mammal to treat or prevent PD-related deficit(s) in the mammal. In some embodiments the mammal is a human. In some embodiments the deficit is Parkinson's Disease.

EXAMPLES

A. Materials and Methods

1. Mice

Figure 1:
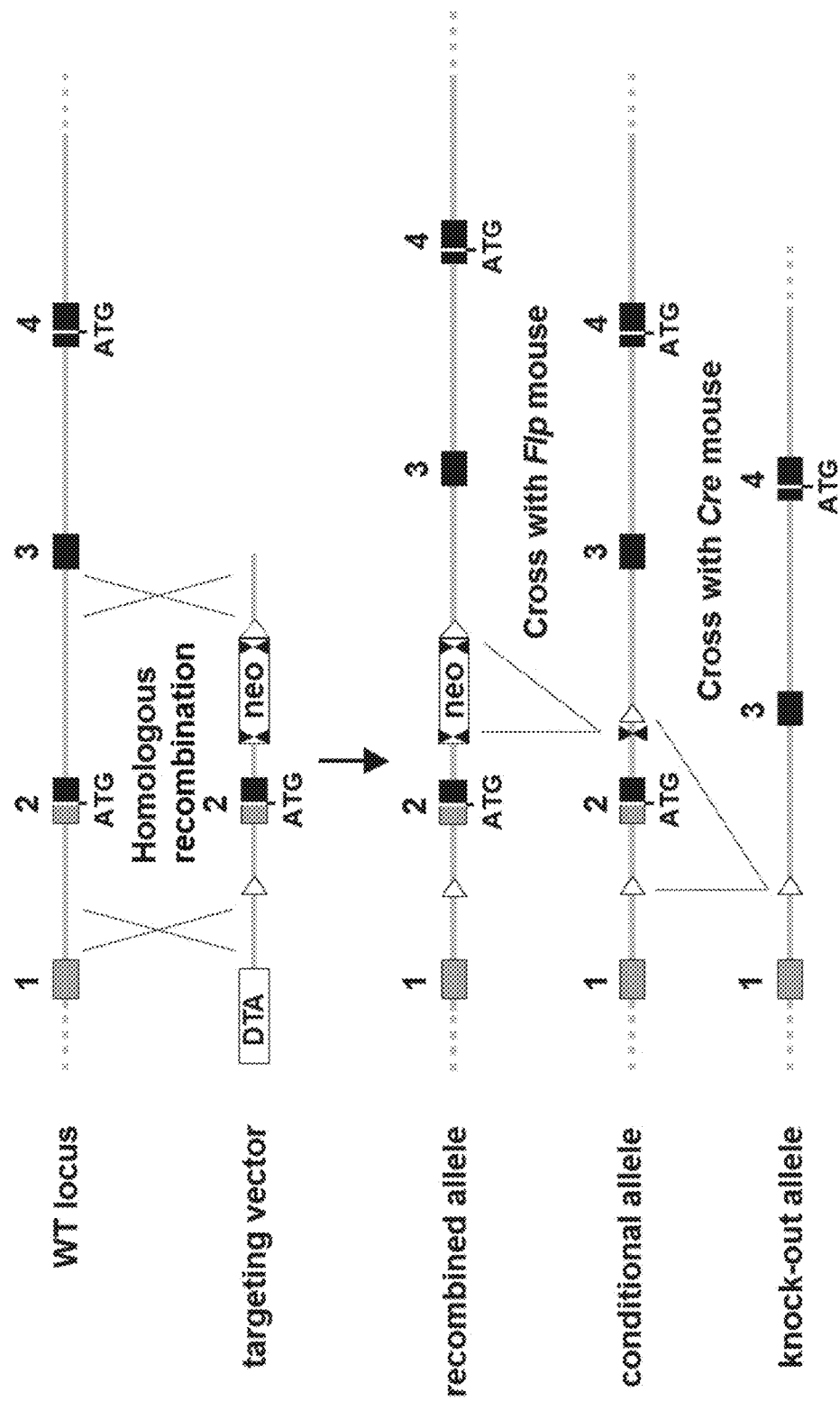
FIG. 1 shows generation of a new PLA2g6 mouse model by deletion of Exon 2. WT Pla2g6 locus and the targeting vector are schematically represented at the top of the panel. Exon 2 of Pla2g6, containing the translation initiation codon, is flanked by two loxP sites (open triangles), whereas the neomycin cassette (Neo) is immediately flanked by two FRT sites (double filled triangles). As depicted, the expected homologous recombination event creates the recombined (foxed) locus and removes Diphtheria Toxin A (DTA) negative selection marker. Crossing a recombined Pla2g6 locus mouse with a ubiquitous Flp recombinase C57BL/6 animal allowed for excision of the FRT-flanked region, creating an animal carrying conditional Pla2g6Ex2 allele without neomycin selection cassette. Breeding the heterozygous recombined F1 mouse with a ubiquitous Cre recombinase C57BL/6 animal resulted in the Cre-mediated excision of the floxed exon 2 region, creating a total Pla2g6 Ex2 knockout ($KO^{Ex2}$) mouse.
Figure 2:
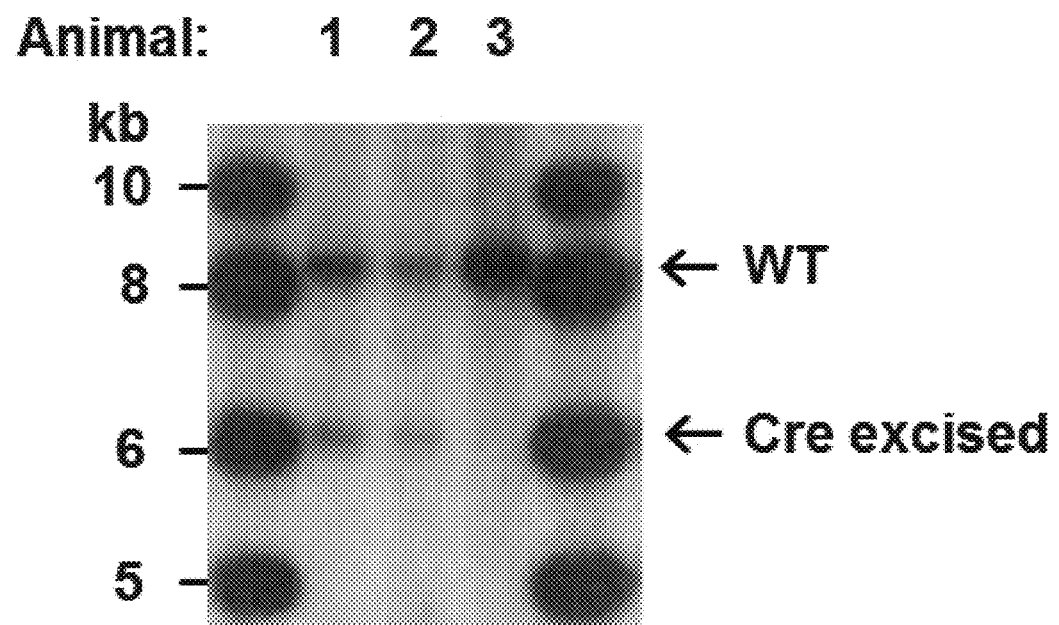
FIG. 2 shows southern blot confirmation of the constitutive Pla2g6 exon 2 knockout. The genomic DNA of the 2 tested F1 mice (lanes 1 and 2) were compared with wild-type DNA (lane 3). The HpaI/NheI digested DNAs were blotted on nylon membrane and hybridized with the probe expected to anneal to the 3' end of homology arm of the targeting vector to validate the zygocity of the $Pla2g6^{Ex2}$ constitutive knock-out gene mutation in these animals. The expected fragments are: 8.2, 9, and 6.1 kb for WT allele, recombined/floxed allele, and constitutive knock-out allele (foxed region deleted), respectively.

PLA2g6$^{Ex2}$ conditional and constitutive knockout (KO$^{Ex2}$) mouse models were created using the strategy outlined in FIG. 1. Briefly, a DNA fragment containing exon 2 and adjacent intron regions of the PLA2g6 gene was isolated by PCR from the 129Sv/Pas genetic background mouse, and subcloned into the pCR4-TOPO vector (Invitrogen). To construct a targeting vector, a fragment including exon 2 (containing ATG$_1$ codon) and a fragment located in the third intron of the PLA2g6 gene were used to flank a neomycin selection cassette (FRT site-MC1-Neo-FRT site-loxPsite), and a distal loxP site in intron 1. Mouse 129Sv ES cells (GenOway, France) were electroporated with the linearized targeting construct and homologous recombination was assessed in 1408 selected ES cell clones via PCR and Southern blot (FIG. 2). One of the PLA2g6 recombined ES cell clones was microinjected into C57BL/6 blastocysts, and gave rise to male chimeras with significant ES cell contribution as determined by an agouti coat color >50%. After mating the chimeras with C57BL/6 females, the agouti colored F1 offspring were genotyped for germ line transmission of the PLA2g6 recombined allele. Floxed heterozygous PLA2g6 conditional knockout animals were generated by Flp-mediated excision of the neomycin resistance gene. The heterozygous constitutive PLA2g6$^{Ex2}$ knockout mice were generated by breeding of foxed conditional heterozygous mice with ubiquitous Cre recombinase C57BL/6 mice, and Cre-mediated excision of targeted exon 2 was verified by genotyping of tail DNA via PCR (FIG. 3). Due to infertility of homozygous PLA2g6$^{Ex2}$ KO males, and inability of females to produce/sustain live pups, cross-breeding of heterozygous KO$^{Ex2}$ mice was used to produce homozygous (KO$^{Ex2}$) animals. Experimental sets of homozygous (KO$^{Ex2}$) and wild type (WT) littermates were housed (and aged) together in the same cage until used for the studies. Animals were maintained in advanced pathogen-free facility with veterinary service and unlimited access to food and water. All experimental procedures were approved by the Institutional Animal Care and Use Committee of Boston University.

2. Motor Coordination Tests

Figure 6C:
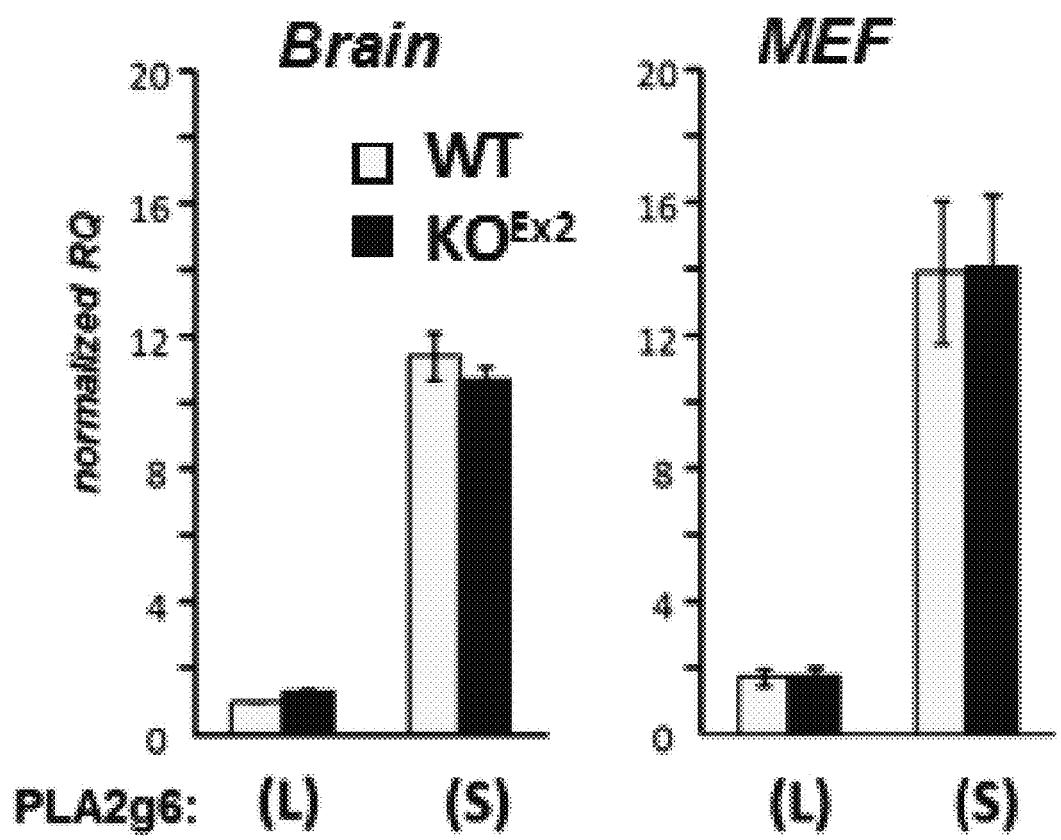
Figure 6D:
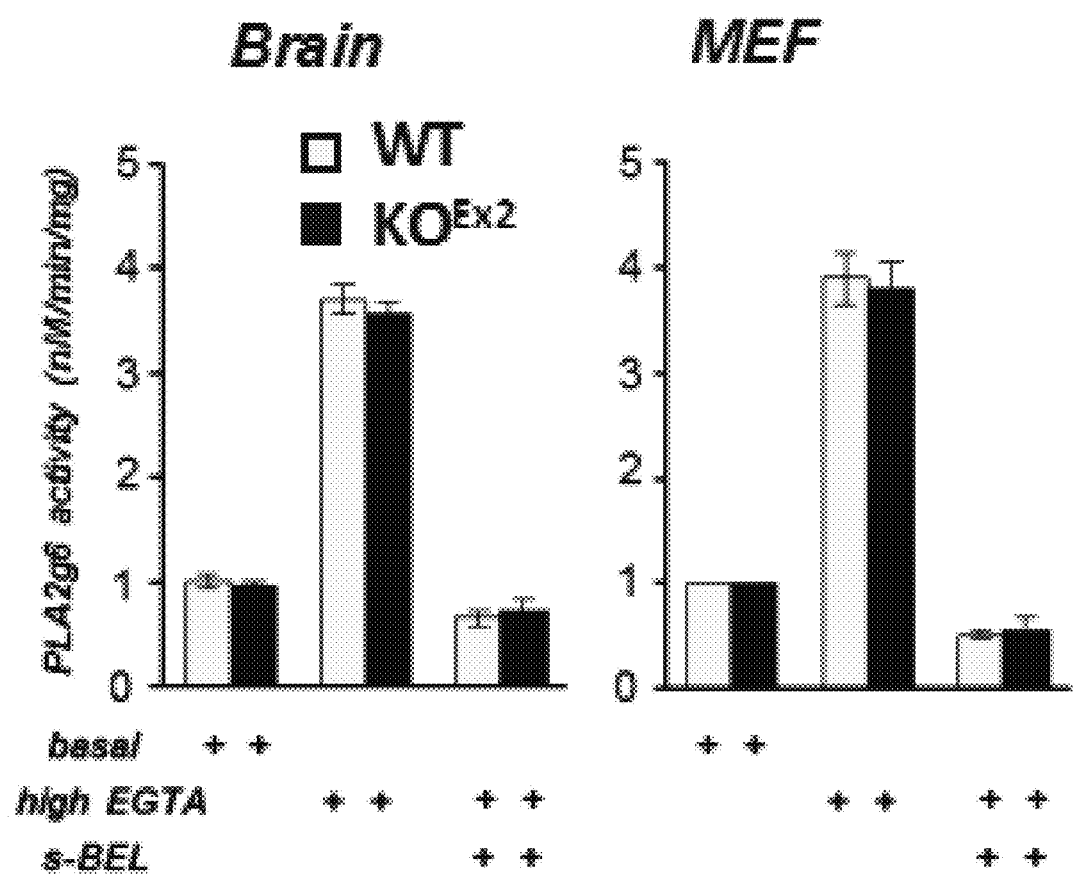
Figure 6E:
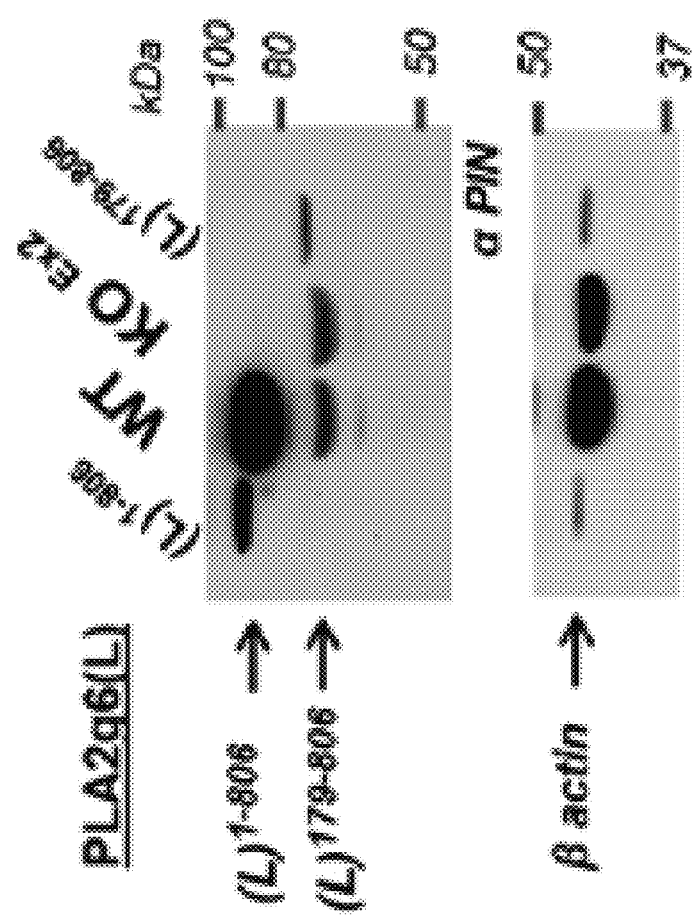
Figure 6F:
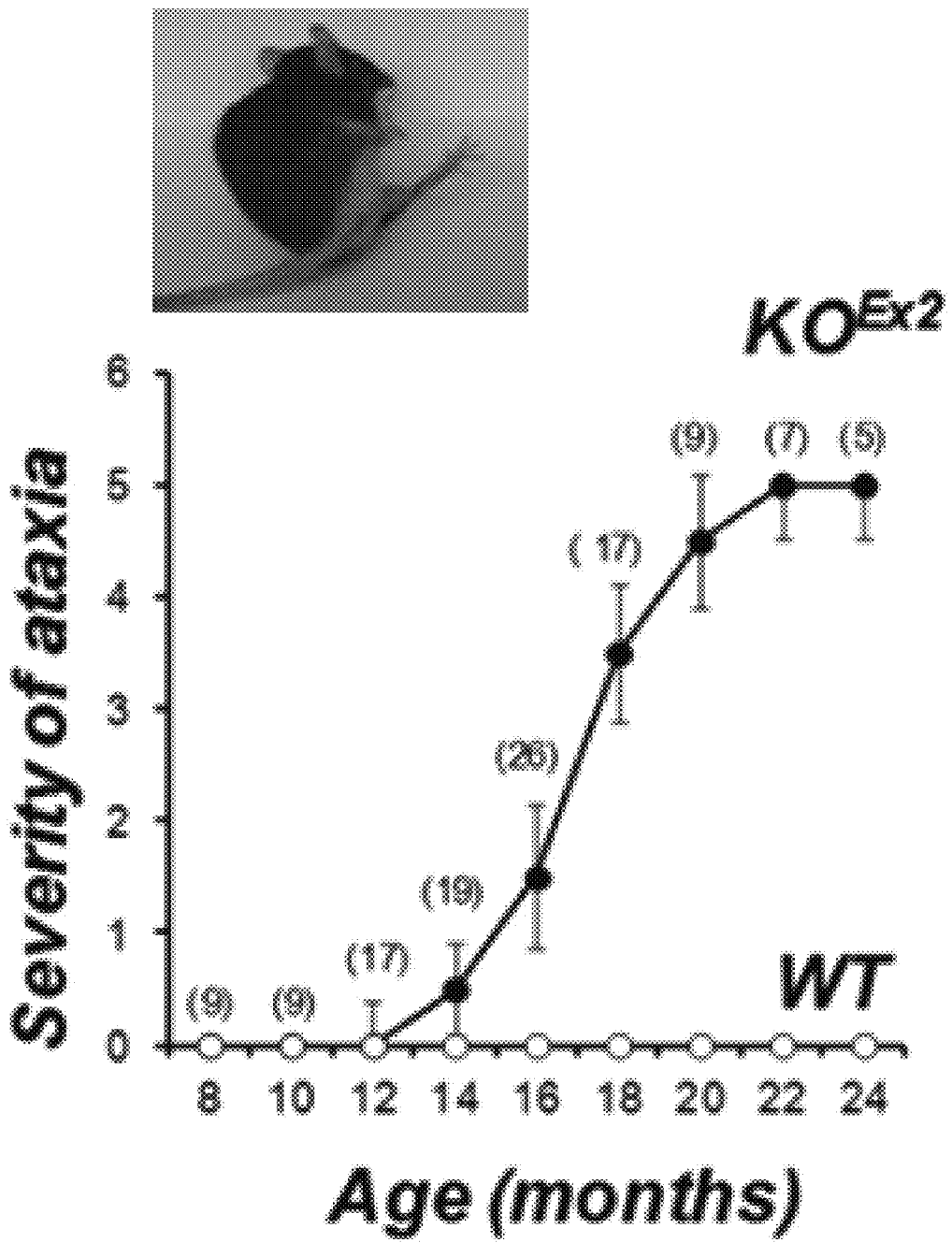
Figure 6H:
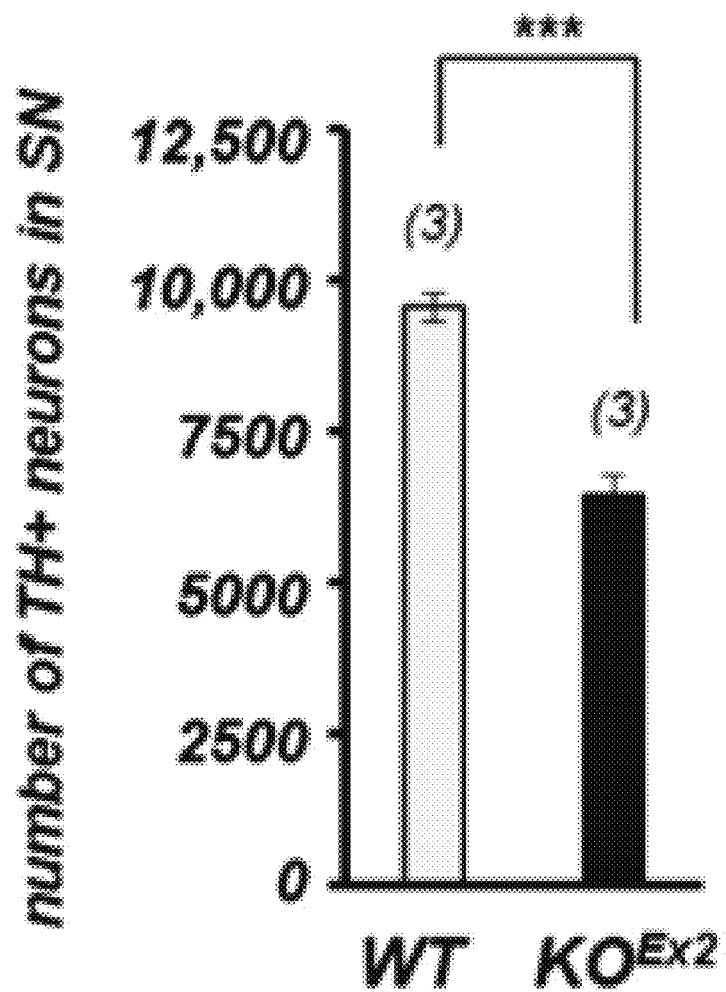

To assess age dependency of progressive motor deficit, KO$^{Ex2}$ and WT mice were evaluated weekly for the signs and severity of ataxia symptoms. Motor deficit was assessed in arbitrary units (AU) using the following scale: 0=No abnormalities noted; 1=first subtle signs of ataxia; 2=obvious signs of movement impairment, but normal postural stability; 3=obvious signs of impairment in movement and occasional postural instability; 4=strong ataxia and instability, but no difficulty with eating, drinking and grooming; 5=very strong ataxia resulting in difficulty with keeping sternal/upright position, and frequently falls when walking, but still can eat, drink and groom, although with some difficulty; 6=death. FIG. 6f shows the time course of motor deficit development, and each point indicates median severity (±SEM) of the symptoms in a number of animals (identified on the graph) tested at different time points.

The grip test (FIG. 10c) was performed using standard approach (54). Grip Strength Meter (GSM) (Columbus Instruments, Columbus, Ohio) was used to objectively quantify the muscular strength of the forelimbs and hind limbs of sex- and age-matched $KO^{ex2}$ and WT animals (between 16 and 18 months of age). All tests (4 repetitions) were performed at the same time in the morning. Strength force was normalized to body weight, which was measured each time after the test. The data were summarized for each group as mean±SEM; the numbers of animals used for these studies is identified on the graphs.

The rotarod test (FIG. 10b) was performed using standard approach (55). Age-matched male $KO^{ex2}$ and WT animals (between 16 and 18 months of age) were tested, and the length of time each mouse can maintain its balance and stay on a rotating rod (3 cm diameter) was analyzed. Before actual experiment, mice were trained on the Rotarod during four sessions (2/day): each training session lasted 120 seconds at a speed of 5 revolutions per minute (rpm). The actual test was performed in the next 2 days (2 times/day): each test consisted of placing the mouse on the rod at 5 rpm for 60 seconds (stabilizing period) followed by acceleration to 25 rpm within the first 60 seconds until the animal fell from the rod, or until total of 240 seconds were reached. Average of 4 measurements of the latency to fall (in seconds) was determined for each mouse and data summarized for each group as mean±SEM; the numbers of animals used for these studies is identified on the graphs.

The balance beam test (FIG. 10d) was performed using standard approach (55). The balance beam test showed the ability of mice to maintain balance while walking along a narrow (2 cm) beam placed 20 cm above a soft mattress. $KO^{ex2}$ and WT males from 8 to 24 month of age were tested. Each mouse was placed on a beam for 2 minutes, and its movement was recorded by video camera. The total travel distance, the number of missteps (paw faults, or slips) during travel were analyzed for each mouse, and data summarized for each group as mean±SEM; the numbers of animals used for each time point is identified on the graphs.

L-DOPA challenge test (FIG. 10e) was performed on $KO^{ex2}$ and WT littermates mice at 12, 16 and 24 months of age. Control beam balance test was performed in the morning a day before L-DOPA challenge. In the morning of the following day, all mice received a single dose of L-3,4-dihydroxyphenylalanine (L-DOPA) via peritoneal injection. Three different doses (5, 10 and 25 mg/kg, Sigma) were tested on the same groups of animals in separate experiments performed with 2-3 days intervals. During each test 20 minutes before L-DOPA administration, mice were given 6 mg/kg of Benserazide (Sigma) to inhibit peripheral DOPA decarboxylase. Beam balance test was done 1 h after L-DOPA injection, as described above. Video-recorded data for each mouse were analyzed later, and summarized for each group as mean±SEM; the numbers of animals used for these studies is identified on the graphs.

3. Brain Slice Preparation and Analysis

Brain was extracted following paraformaldehyde (PFA, 4%) perfusion, and stored in 4% PFA at 4° C. Brain slices were prepared and stained using standard protocols (58). Briefly, the brain was embedded in OCT Tissue-Tek, and a small cut was placed on the right side of the frozen OCT block near the right cortex for side identification. WT and $KO^{Ex2}$ brains were sectioned coronally (30 μm thick) with a cryostat microtome (Thermo Scientific). Free-floating sections were collected in a 24-well plate (BD Falcon) with PBS, sealed and stored in 4° C. The sections of the substantia nigra (SN) were collected in a staggering method, and several sets of six tissue sections were collated: each set contained similar sections from the front, middle, and back of the SN region. The same procedure was done for the caudate putamen (CPu) region. Immunostaining of tyrosine hydroxylase (TH) rabbit monoclonal antibody (Calbiochem) and DAB (Vector Laboratories) was done using standard technique. The endogenous peroxidase activity was blocked by 3% hydrogen peroxide in PBS (20 min at room temperature). The sections were then washed, immersed in 0.1% Triton X-100/PBS for 30 minutes and moved to a blocking buffer of 5% normal goat serum in 0.1% Triton/PBS for 60 minutes. Stained with tyrosine hydroxylase (TH) rabbit monoclonal antibody (1:1000 dilution) was done at 4° C. overnight followed by washing in 0.1% Triton/PBS and immersion in Envision™+ Rabbit (Dako) solution at room temperature for 1 hour. After washing with 0.1% Triton/PBS, DAB (Vector Laboratories) staining was developed. The stained sections were mounted on gelatin-coated slides, counterstained with Gill's hematoxylin and sealed with Permount.

The total numbers of TH-positive neurons (left plus right side) was counted in each of 6 sections using standard blind stereology technique, and the total number of TH+ neurons in substantia nigra of each animal was estimated using standard algorithm used for stereological studies. The number of TH-positive neurons were compared between age-matched WT and $KO^{Ex2}$ male mice (n=3 animals in each group).

4. Primary MEF Preparation and Transfection

MEF cells were isolated from embryos (14.5 days old) obtained from either WT females (mated with WT males), or homozygote KOEx2 females (mated with het KOEx2 males). Each embryo was genotyped. Head, vertebral column, dorsal root ganglia and all internal organs were removed and discarded; the remaining embryonic tissue was manually dissociated and incubated in 0.25% trypsin (Sigma) for 15-30 min. Cells from each embryo were plated onto a 10 cm tissue culture dish in MEF media (Dulbecco's modified Eagle medium (DMEM; Mediatech Inc.) containing 10% fetal bovine serum (FBS; Hyclone), non-essential amino acids, sodium pyruvate and penicillin/streptomycin (Invitrogen). After reaching confluence, primary MEFs from WT and $KO^{Ex2}$ embryos were collected and stored in liquid nitrogen for future use. All experiments were done on passage 2 (P2) or P3 cells.

Transfection of MEFs was performed using the Amaxa Nucleofector™ system (Lonza, Allendale, N.J., USA). Briefly, the cells were thawed and grown for 24 h, and then lifted, and re-plated in a 6-well plate at a density of 200,000 cells per well. After 24 h the cells from each well were collected, centrifuged, re-suspended in 100 μl of electroporation solution (Minis Bio, Madison, Wis., USA), mixed with 2 μg of the recombinant plasmid DNA and transfected using T020 program. After electroporation, the cells were added to 2 ml of warm DMEM containing 10% FBS and 1% penicillin/streptomycin, and grown for the next 24-72 hours as specified. Transfection efficiency (verified by GFP expression) was >70%.

5. $Ca^{2+}$ Imaging

MEFs were cultured in glass bottom dishes coated with fibronectin (2.5 μg/cm$^2$, Sigma, St. Louis, Mo., USA) for 24-48 hours. Intracellular $Ca^{2+}$ measurements were done similar to published earlier (57). Briefly, the cells were loaded with fura-2/AM (5 μM) (Invitrogen), and cytosolic Ca$^{2+}$ (measured as $_{F340/F380}$ ratio) was recorded simultaneously in 10-20 individual cells using a dual-excitation fluorescence imaging system (Intracellular Imaging, USA): representative traces show an average (±SEM) for 10-20 cells recorded simultaneously. Ca$^{2+}$ changes were calculated as Δ Ratio$_{(F340/F380)}$, which is the difference between the basal and peak values of Ca$^{2+}$ responses. Summary data show the average (±SEM) responses of more than 100 cells from at least 3 independent experiments for each condition.

The following treatments were used in Ca$^{2+}$ studies (FIG. 14): TPEN (N,N,N',N'-Tetrakis(2-pyridylmethyl)ethylenediamine, Sigma, USA) was applied (400 μM) directly to the cells during recording, 3 min before 2 mM Ca$^{2+}$ addition; (S)-BEL ((S)-bromoenol lactone, Cayman, USA) was applied (50 μM for 20 min in serum-free medium at 37° C.) to the cells after their loading with fura-2/AM, and was washed away before the start of experiment; EGTA (2.5 mM) was added to 2 mM Ca$^{2+}$-containing bath solution right before ionomycin (IM, 1 μM) application.

6. PLA2g6 Activity

The activity of PLA2g6 (FIG. 14) was determined using modified PLA2 assay kit (Cayman, USA), as previously described (56, 63). Briefly, after each experimental treatment, MEFs were homogenized using a cold lysis buffer (10 mM Tris-HCl, pH 7.0, 300 mM sucrose, 0.5% Triton X-100). To identify specific activity of Ca$^{2+}$-independent PLA2g6, the assay buffers were modified to contain no Ca$^{2+}$, and phospholipase activity was assayed by incubating the samples with the substrate, 1-hexadecyl-2-arachidonoylthio-2-deoxy-sn-glycero-3-phosphorylcholine for 1 h at room temperature in a modified Ca$^{2+}$-free assay buffer (10 mM HEPES, pH 7.4, 300 mM NaCl, 60% glycerol, 8 mM Triton X-100, 4 mM EGTA, and 2 mg/ml bovine serum albumin). The generated free thiols were visualized by the addition of DTNB (5,5'-dithiobis(2-dinitrobenzoic acid)) for 5 min, and the absorbance was determined at 405 nm using a standard microplate reader. In calculations of specific PLA2g6 activity a value of 10 mM$^{-1}$ was used as extinction coefficient for DTNB at 405 nm. Summary data present average (±SEM) from 3 independent experiments for each condition.

7. Antibodies

Figure 4A:
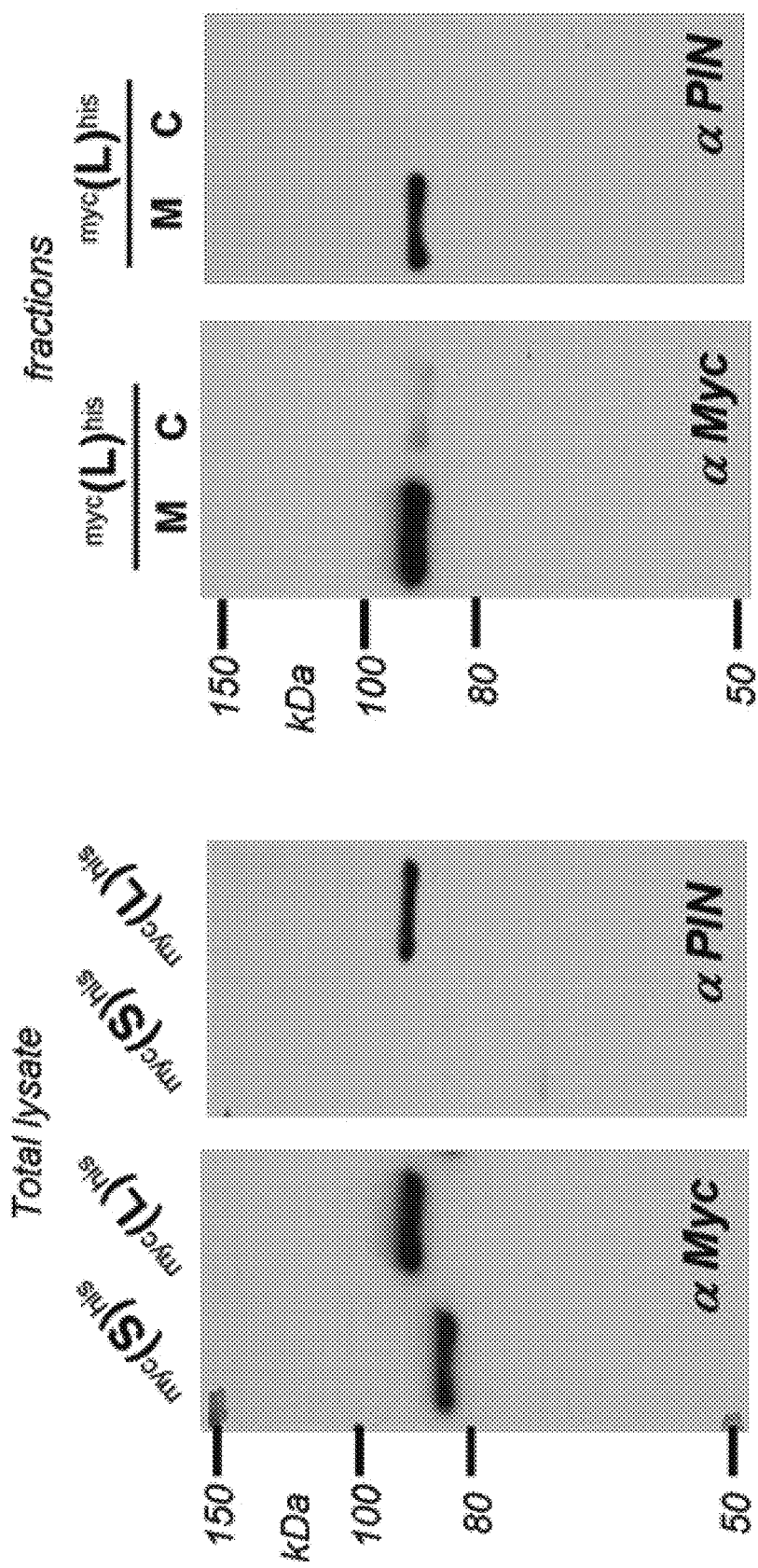
FIGS. 4A and 4B show specificity of PIN antibody to (L) variant of PLA2g6, and its association with membrane fraction. A: WB on the left shows that while (S) and (L) variants of mycPLA2g6his (expressed in HEK293-F) could be recognized by Myc antibody, PIN antibody (specific to human PIN region of PLA2g6(L)) recognizes only (L) variant. WB on the right shows that (L) variant of PLA2g6 could be detected by Myc and PIN antibodies in the membrane fraction of HEK293-F cells.
Figure 4B:
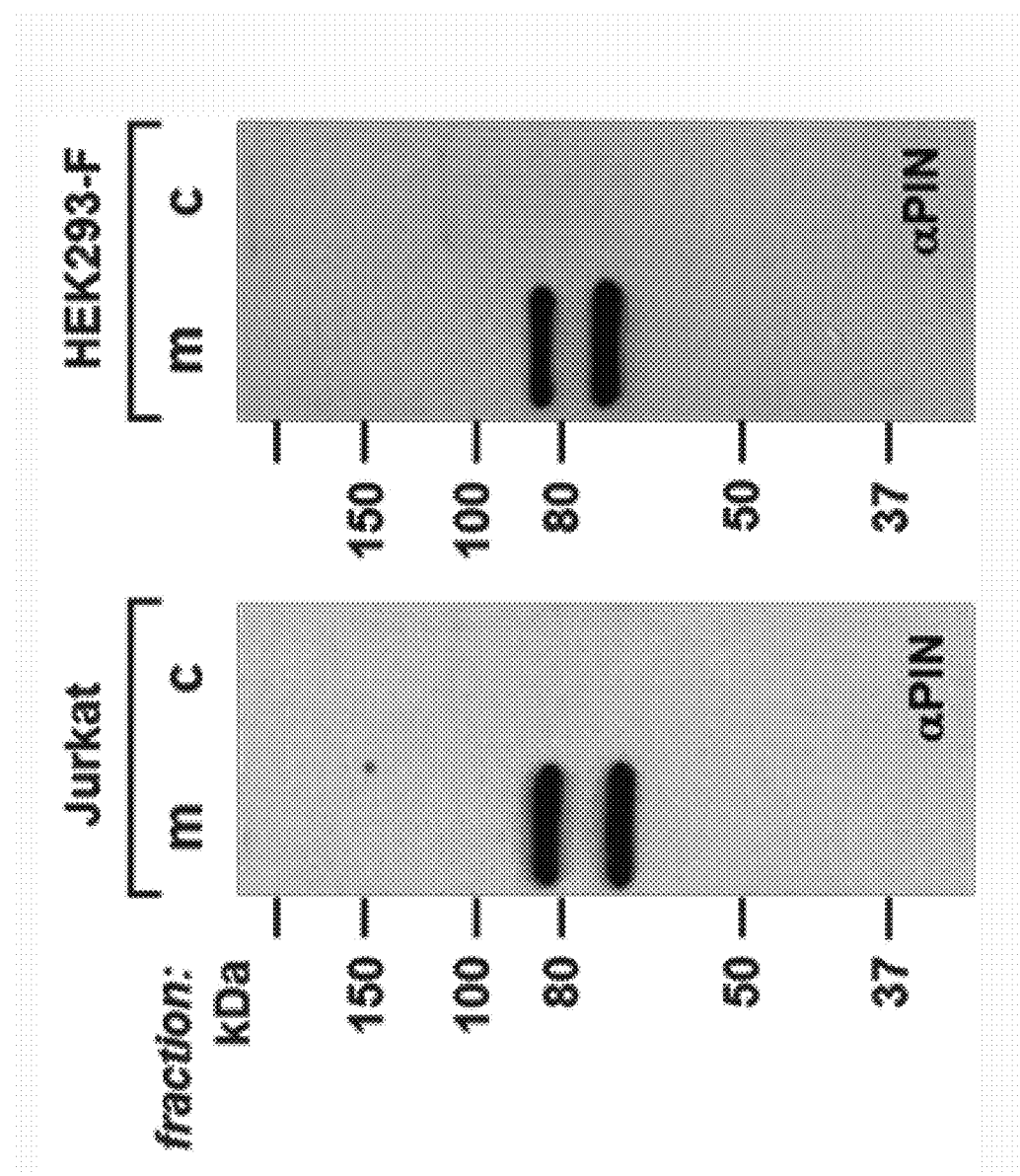

Polyclonal antibodies targeting PIN insert that is present in (L), but spliced out in (S) variant of PLA2g6, were custom made by Yenzym Antibodies, LLC (San Francisco, Calif.). Briefly, the rabbits, from which pre-immune serum has first been obtained, were immunized with keyhole limpet hemocyanin-conjugated peptide (CSTEQGSAAATHPLFSLDRTQPP-amide (SEQ ID NO: 3)) corresponding to residues 422-443 of mouse PLA2g6(L). Desired pool of antibodies was purified from the collected serum by antigen-specific affinity chromatography. Final preparation of the antibody was obtained in PBS stabilized by sodium azide and diluted 1:1 (to 0.5 mg/ml antibody concentration) with 100% glycerol. Specificity of αPIN to PLA2g6(L) is shown in FIGS. 4 and 5. Commercial anti-STIM1 mouse monoclonal Ab CDN3H4 (Novus Biologicals) was used for Western blot and P-LISA detection of endogenous STIM1 as described below.

8. Western Blot

Mouse tissue was homogenized using RIPA buffer (50 mM Tris-HCl, pH 7.4, 150 mM NaCl, 1% NP-40, 0.5% Sodium deoxycholate, 0.1% SDS, 3 mM DTT, and 1× HALT protease inhibitors (Pierce)), sonicated and centrifuged. Protein concentration was determined by a Bradford protein assay (Bio-Rad). Proteins were electrophoresed through a 10% SDS-polyacrylamide gel and transferred to a supported nitrocellulose membrane (Bio-Rad) by electroblotting. The membranes were incubated in blocking buffer (5% nonfat dried milk in TBST) for 1 h before immunoblotting was performed with primary anti-PLA2g6(L) (αPIN, 1:1,000 dilution), R-actin (Sigma, 1:10,000 dilution) antibody at 4° C. overnight. HRP-conjugated mouse Ab was used as secondary Ab. The blots were developed with SuperSignal West Dura Extended Duration Substrate (Thermo Scientific). Experiments were repeated more than three times. The samples obtained after immunoprecipitation and pull-downs were analyzed similarly, with the respective primary antibodies (FIGS. 11, 12, 13). Full blots for each representative panel in FIG. 11 are shown in FIGS. 12 and 13.

9. Immunoprecipitation

Custom-made rabbit polyclonal PIN antibody (αPIN) was used to immunoprecipitate endogenous PLA2g6(L) from homogenates obtained from testes of 2-4 months old WT mice. Testes were extracted, snap-frozen in liquid nitrogen and stored at −80° C. until used. Each testis was homogenized in 2 mL of ice-cold lysis buffer (LB; 25 mM Tris-HCl, pH 7.5, 50 mM NaCl, 5% glycerol, 5 mM EDTA, 5 mM EGTA, 1 mM PMSF, 1× HALT Protease Inhibitors (Pierce)) and sonicated. The resulting homogenate was supplemented with 150 mM NaCl and centrifuged at 3000 g at 4° C. for 20 min. Cleared supernatant was collected, brought to the desired concentration and ~1.5-3 mg of protein was supplemented with either 8 μg of αPIN, or equivalent amount of the pre-immunized serum from the same rabbit as a control, and incubated for 1 h at 4° C. Antigen-antibody complexes were precipitated by Protein G-agarose (Sigma IP kit) by overnight incubation at 4° C. Following the incubation, Protein G-agarose was filtered and washed 5× with 600 μL of IP buffer (Sigma IP kit), 4× with IP buffer supplemented with 500 mM NaCl, 1× with 0.1×IP buffer, and finally 2× with PBS. The immunoprecipitated complexes were eluted with 100 μL of 3× Laemmli buffer by 15 min incubation at 95° C., and analyzed by Western blot (FIGS. 11a and 13).

10. Proximity Ligation In Situ Assay (P-LISA) (64)

P-LISA was performed on MEFs (FIG. 11c) using similar approaches successfully used by others (61, 62). MEFs (P2) were seeded on glass cover slips coated with fibronectin (2.5 μg/cm$^2$, Sigma, USA), cultured for 24 h, treated with 10 μM TG or DMSO (as control) for 10 min at room temperature, and then fixed with 1:1 acetone:methanol for 5 min at −20° C. Following 3 washes with PBS, the cells were permeabilized with 0.5% Tween 20 in PBS, blocked with 3% BSA in PBS (blocking solution) for 1 h, and then incubated overnight at 4° C. with the custom made rabbit polyclonal anti-PLA2g6 (αPIN) and mouse monoclonal anti-STIM1 (Novus Biologicals) antibodies, both at 10 μg/mL, in blocking solution. Subsequently, the cover slips were washed 3 times with blocking solution supplemented with 0.2% Tween 20, and the P-LISA staining procedure was performed according to manufacturer's instructions (Duolink® In Situ kit, Olink Bioscience). Briefly, the fixed cells were incubated with PLA Probe Anti-Rabbit MINUS and PLA Probe Anti-Mouse PLUS diluted 1:5 in blocking solution for 1 h at 37° C., and then washed twice with blocking solution supplemented with 0.2% Tween 20, and twice with PBS. Proximity ligation and the rolling circle amplification were performed under conditions described by the manufacturer. After washing, the cells were stained with 300 nM DAPI and fixed with a Fluoromount mounting solution (SIGMA), supplemented with DABCO. For imaging we used Nikon Eclipse Ti inverted fluorescence microscope with 60×/1.4

Apo-Plan oil objective (Nikon) and filter sets for TexasRed (part number: 96365, ex/em: 540-580/600-660, Nikon) illumination. For analysis, images were processed using ImageJ (Wayne Rasband, Maximum intensity Z-projections were analyzed for the number of the particles. A threshold equal to 3 times the background value was applied, binary image was formed and analyzed using the "particle analysis" feature of ImageJ (parameters used at default values). This analysis yielded a very conservative estimate of the number of particles per each cell, as the clusters of particles (formed after TG treatment) would tend to be counted as a single large particle 11. Pull-Down Experiments (FIGS. 11a and 12)

FreeStyleT 293-F cells (Life Technologies) were cultured in serum-free FreeStyleT 293 Expression Medium (Life Technologies) without antibiotics, as suspension 30 mL cultures at 37° C. in a humidified atmosphere of 8% CO2 on an orbital shaker. To obtain bait protein extracts, suspension cultures were transfected with either the empty pSNAP-tag (m) vector (New England Biolabs), or with the C-terminally SNAP-tagged human PLA2g6(L) constructs: full length $(L)^{1-806}$, $(L)^{179-806}$, or $(L)^{1-150}$. The cells were harvested 48 h after transfection, lysed on ice in lysis buffer (25 mM Tris-HCl, pH 7.5, 150 mM NaCl, 0.5% NP-40, 5% glycerol, 2 mM DTT, 1× HALT Protease inhibitors cocktail (Pierce), 1 mM PMSF) and the extracts were cleared by centrifugation for 15 min at 16,000 g at 4° C. Each SNAP-tagged protein was covalently immobilized by incubating ~800 µL of the extract with 25 µL bed volume of SNAP Capture Resin (New England Biolabs), equilibrated with Resin Wash Buffer (RWB; 25 mM Tris-HCl, pH 7.5, 150 mM NaCl, 5% glycerol), for 16 hat 6° C. Control sample of each extract was incubated under the same conditions in the absence of the resin. Following immobilization, the resin was collected in the mini spin column (Pierce), washed 5 times on ice with 600 µL of RWB, combined with the prey protein extract, and incubated with orbital mixing at ~600-800 rpm for 6 h at 4° C. Prey protein extracts were prepared similar to the bait protein by lysing Jurkat T lymphocyte cells or FreeStyleT 293-F cells transfected with $^{YFP}$STIM1 construct (kind gift from Dr. T. Meyer, Stanford University, Stanford, Calif.) in the lysis buffer without DTT. After incubation, the resin was washed 5 times on ice with 600 µL of RWB, 3 times with 600 µL of RWB supplemented to 500 mM NaCl, and once again with 600 µL of RWB, and then all non-covalently bound prey protein was eluted by incubating the resin with 100 µL of 2× Laemmli sample buffer (Bio-Rad) at 95° C. for 7 min, and analyzed by Western blot.

12. Quantitative RT-PCR

Total RNA was isolated from individual testis, or hemispheres of brains of age-matched $KO^{Ex2}$ and WT mice, as well as from primary MEFs using High Pure RNA tissue kit, or High Pure RNA isolation kit (Roche Applied Science), respectively. Concentration and quality of samples was confirmed spectrophotometrically. RNA was reverse-transcribed using High Capacity RNA-to-cDNA Kit (Life Technologies), and equivalent of 150 ng of RNA was analyzed per sample replicate in quantitative PCR on StepOnePlusT Real Time PCR System (Applied Biosystems) using the following TaqMan® gene expression assays: Mm03929082_m1 for PLA2g6(L), Mm03010833_m1 for PLA2g6(S), Mm01299488_m1 for PLA2g6 transcripts encompassing exon 2, and 4352932 for mouse glyceraldehyde-3-phosphate dehydrogenase (GAPDH). The relative quantity data for biological duplicates of each sample was analyzed using ΔΔCT method and normalized internally to the level of GAPDH and externally to the average amount of PLA2g6(L) in the brains of WT mice of C57BL/6J genetic background.

13. DNA Constructs and Oligonucleotides

Human PLA2g6(L) variant (59, 60) (Genbank #AF064594) was a kind gift from Dr. Brian P. Kennedy, Karolinska Institute, Stockholm, Sweden), and was used for creation of all other constructs. C-terminally SNAP-tagged expression constructs of human PLA2g6 were created by inserting sequences coding for the full-length long variant of human PLA2g6(L)$^{1-806}$, PLA2g6 residues 1-150 (L)$^{1-150}$ or residues 179-806$^{(L)179-806}$ between EcoRV and EcoRI sites of the pSNAP-tag(m) vector (New England Biolabs). The sequences of primers used for cloning were as follows:

```
                                          (SEQ ID NO: 4)
F1: aatttagatatc-atgcagttctttggccgcc
(forward for PLA2g6 and (L)^{1-150})

(SEQ ID NO: 5)
F2: aatttagatatcatggatgtcaccgactacaaggg
(forward for (L)^{179-806})

(SEQ ID NO: 6)
R1: aataaggaattcgggtgagagcagcaggtgg
(reverse for PLA2g6 and (L)^{179-806})

(SEQ ID NO: 7)
R2: aatatcgaattcctcgttctccgcgcaattg
(reverse for (L)^{1-150}).
```

The EcoRV and EcoRI restriction sites used for cloning purposes are underlined.

His-tagged and/or myc-tagged expression constructs of PLA2g6(L) were obtained by PCR-subcloning of the full-length long variant of human PLA2g6 into pcDNA3.1 plasmid with polylinker between restriction sites NheI and PmeI exchanged for the following sequence: gct agc gttaac acc ggt atg gaattc gaa caa aaa ctc atc tca gaa gag gat ctg gat atc cct gca ggc taa gga tcc cac gtg ctc gag cgt ctc caa ttg gcg gcc gca aga gga tcg cat cac cat cac cat cac tag agt gaa gct taa gtt taa ac (SEQ ID NO: 8), allowing for expression of various double- and single-tagged fusions with myc and/or his tags (italicized). The sequence coding for PLA2g6(L)$^{1-806}$ or PLA2g6(L)179-806 was cloned between HpaI and EcoRI (for C-terminal myc-tagging), or EcoRV and BsmBI sites (for N-terminal myc- and C-terminal his-tagging) of the modified MCS using primers F1 and R1, or F2 and R1 (see above).

A cDNA construct coding for the full-length short variant of human PLA2g6 (PLA2g6(S)) was constructed using a clone of human PLA2g6(L) by removal of the region coding for the PIN (equivalent to exon 8b, see FIG. 1a). A two-insert mutagenesis strategy was designed, and cDNA coding for PLA2g6(S) was PCR-amplified using the following pairs of primers: F1 and R3: aat tta cgtctc ctag ttg tct gcc gat ttt gga ggc tag (SEQ ID NO: 9); and F3: aat tta cgtctc aa cta caa gac ttg atg cat ata agt cg (SEQ ID NO: 10) and R2. The BsmBI restriction sites used for cloning purposes are underlined, and the cohesive overhangs designed to ligate the fragments are italicized. Sequences of all target protein-coding fragments of the final clones were confirmed by DNA sequencing.

Oligonucleotides used as PCR genotyping primers (see FIG. 3) were as follows: set 1: gtgaacacacaggctaaggctc-caatcta (SEQ ID NO: 11) and tcaacaagcaaaggacagacatcccac (SEQ ID NO: 12); set 2: agcagaggggcaggctgggtctctc (SEQ ID NO: 13) and aggaacacagttgttgggctggggttgtc (SEQ ID NO: 14); set 3: tatcttctcgagttctctagcctc-caatcctggg (SEQ ID NO: 15) and cacatagaattcgtccccttgcacagcgtaatgg (SEQ ID NO: 16); and set 4: agcagaggggcaggctgggtctctc (SEQ ID NO: 13) and cacatagaattcgtccccttgcacagcgtaatgg (SEQ ID NO: 16).--.

14. Statistical Analysis

A Student's t test and two-way analysis of variance (ANOVA) were used for comparison among different groups. Differences were considered significant at p<0.05, p values were identified in the figures as *(p<0.05), (p<0.01), *(p<0.001).

B. Results

Example 1: Creation of PLA2g6 KO$^{Ex2}$ Mice

The inventor hypothesized that impairment of a specific $Ca^{2+}$ signaling function of PLA2g6 may be a new key to Parkinson's Disease as DA neurons in SNpc were found to be particularly vulnerable to $Ca^{2+}$ influx through voltage-gated $Ca^{2+}$ channels[26-29]. To test this idea, mice comprising a constitutively deleted Exon 2 coding for the translation initiation ($ATG_1$) of PLA2g6 (FIG. 6a) were created (FIG. 6a-b and FIGS. 1-3). It was hypothesized that such deletion could result in either a total ablation of all splice variants of PLA2g6, or (in view of the presence of a cryptic $ATG_2$ in Exon 4) in creation of a genetically truncated PLA2g6 lacking the first 178 amino acids in N terminus (FIG. 6a and FIG. 15). The function of N-terminus of PLA2g6 was unknown, but its truncation was hypothesized to not affect catalytic activity, as this function is encoded by C-terminus of PLA2g6. This strategy resulted in generation of PLA2g6 Exon 2 constitutive, as well as conditional knockout (KO$^{Ex2}$) mouse models (see Methods and FIGS. 1-3).

Comparative analysis of PLA2g6 expression (FIG. 6.c), overall catalytic activity (FIG. 1d), and endogenous PLA2g6 protein (FIG. 6.e) revealed important similarities and differences between KO$^{Ex2}$ and WT animals. Deletion of Exon 2 did not change mRNA levels of long (L) and short (S) variants of PLA2g6. Importantly, analysis identified no differences in overall PLA2g6 catalytic activity (FIG. 6.d), its activation by high EGTA (which directly displaces inhibitory CaM[30,31]), and its inhibition by S-BEL (chiral-specific suicidal inhibitor[32]) in homogenates of the brain, or mouse embryonic fibroblasts (MEFs) from KO$^{Ex2}$ and WT animals. To detect endogenous protein, a new custom polyclonal antibody (αPIN) was created to specifically target PIN domain that is present in plasma membrane-associated (L) variant, but spliced out in cytosolic (S) variant of PLA2g6 (FIGS. 4 and 5). Western blot analysis of protein samples from the WT and KO$^{Ex2}$ mice (FIG. 6e) confirmed that the full length PLA2g6(L) was present in WT, but absent in KO$^{Ex2}$ mice. However, a shorter product could be detected, and appeared to be similar to recombinant PLA2g6(L)$^{179-806}$ that mimics a protein expected from translation initiation at cryptic $ATG_2$ in Exon 4. The presence of N terminally truncated PIN containing PLA2g6 (L) protein in TH positive (dopaminergic) neurons in substantia nigra was also confirmed by immunostaining of brain slices from KO$^{Ex2}$ mice (data not shown). Thus, deletion of exon 2 resulted in ablation of the full length PLA2g6 while N-terminally truncated protein is present and catalytically active in KO$^{Ex2}$ mice. It is important to emphasize that normal catalytic PLA2g6 activity (FIG. 6d) clearly discriminates the KO$^{Ex2}$ mouse provided by this disclosure from any other PLA2g6 KO models[22-25,33], in which catalytic activity was specifically impaired.

Example 2: Phenotype of PLA2g6 KO$^{Ex2}$ Mice

Figure 10B:
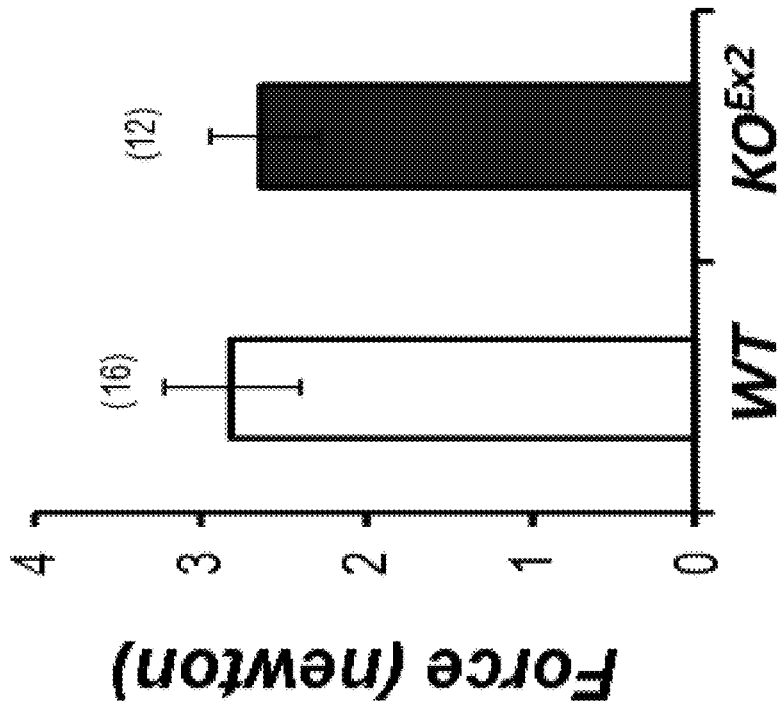
Figure 10C:
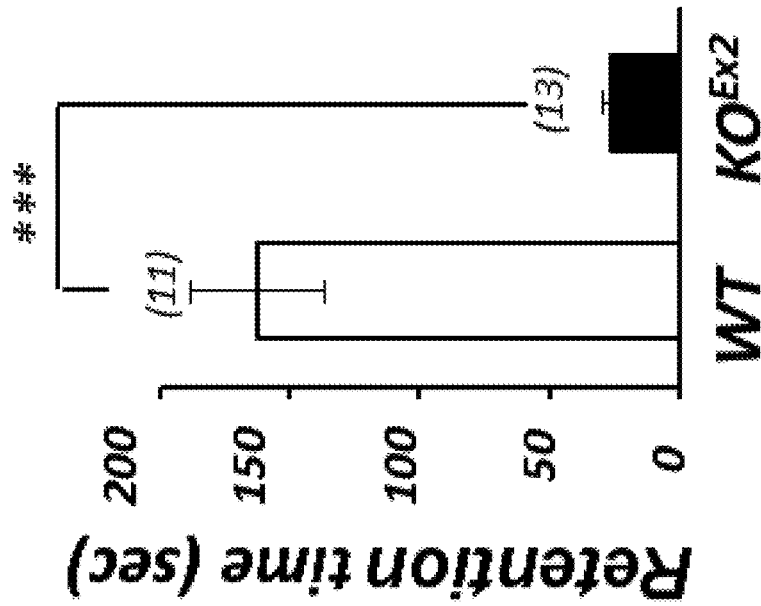
Figure 10D:
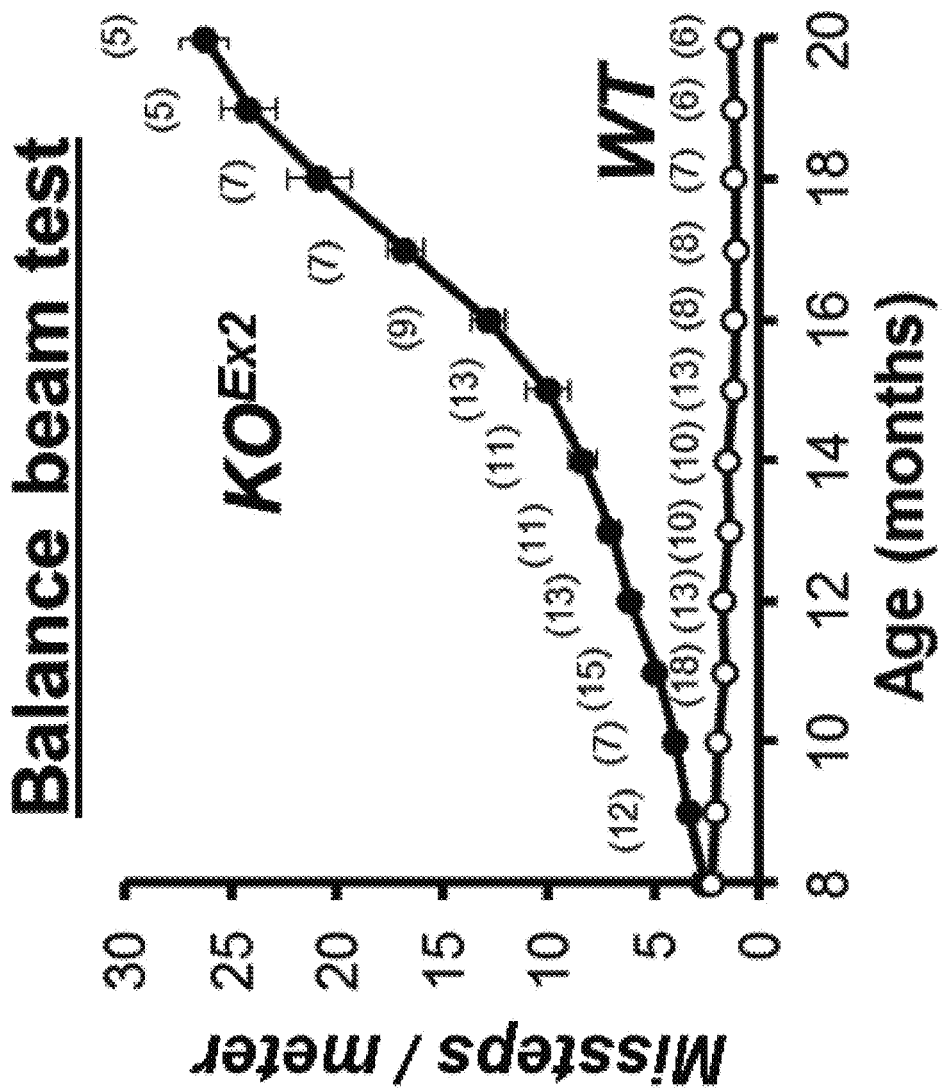
Figure 10E:
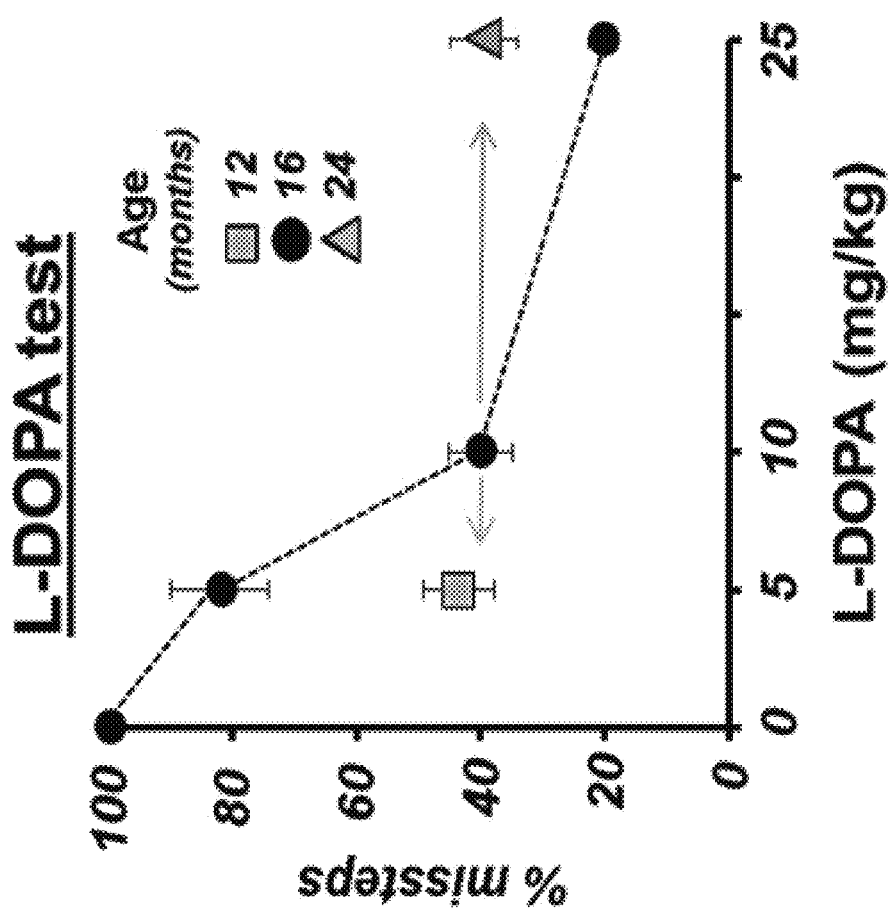

The PD-like phenotype became apparent when aging KO$^{Ex2}$ animals developed tremor and agitation, closely followed by the onset of ataxia and postural instability (FIG. 6f). The age-dependent progression of motor dysfunction was best seen in Balance beam test (FIG. 10d). By 20 months of age all KO$^{Ex2}$ mice of both sex showed severe motor impairment, while WT and heterozygous littermates retained totally normal motor functions until the end of experiment (24 months), which mimicked autosomal recessive inheritance of the Pla2g6 mutation known as PARK14-related PD in humans.

Importantly, there was a progressive age-dependent loss of DA neurons in SNpc of the KO$^{Ex2}$ animals. Staining with tyrosine hydroxylase (TH) antibody showed significant (about 30%) reduction in the number of dopaminergic TH+ neurons in the SNpc of KO$^{Ex2}$ mice at 16 months of age (FIG. 6g, h), and significant reduction in TH+ staining of DA projections to striatum of KO$^{Ex2}$ animals (FIG. 7). At 24 months of age, KO$^{Ex2}$ animals had 50-75% loss of TH+ neurons. In contrast, analysis of hippocampus, motor and temporal cortices (FIG. 8) revealed no differences between WT and KO$^{Ex2}$ littermates, showing that the genetic targeting of PLA2g6$^{Ex2}$ did not result in a widespread nonspecific neuronal loss. Also, no difference in DA neurons was found in SNpc of young (6-8 months old) KO$^{Ex2}$ animals (FIG. 9), consistent with no motor dysfunction found in KO$^{Ex2}$ mice at that early age (FIG. 10d).

To evaluate motor dysfunction and relate it to PD, rotarod (FIG. 10b), grip strength (FIG. 10c), and beam balance tests (FIG. 10d,e) were performed on age-matched KO$^{Ex2}$ and WT mice. While the grip strength did not change (FIG. 10c), the motor function of KO$^{Ex2}$ animals was significantly impaired, as the rotarod retention time decreased 8 fold (FIG. 10b), and age-dependent progressive increase in the number of missteps (FIG. 10d) was evident in beam tests. Importantly, similar to humans[34] administration of L-DOPA (5-25 mg/kg) improved motor performance of KO$^{Ex2}$ mice and significantly reduced the number of missteps (FIG. 10e) in dose and age-dependent manner. Taken together, these results strongly support the dopaminergic (L-DOPA-sensitive) nature of the observed motor dysfunction, and are fully consistent with significant loss of DA neurons found in SNpc (FIG. 6g, h).

Example 3: Characterization of PLA2g6-Dependent $Ca^{2+}$ Signaling

The $Ca^{2+}$ signaling function of PLA2g6 (originally called iPLA$_2$β)[39], and accumulated evidence for its role as endogenous mediator of the store-operated $Ca^{2+}$ entry (SOCE) pathway (for review see[35,36]), together with the phenotype observed in the mutant mice reported herein, suggested that impairment of this specific function of PLA2g6 may be a new key to PD. Indeed, SOCE is activated upon depletion of endoplasmic reticulum (ER) $Ca^{2+}$ stores and ensures their timely refilling[37-39]. $Ca^{2+}$ signaling is very important for neuronal function[49-42], and sustained depletion of $Ca^{2+}$ stores can lead to ER stress, abnormal protein degradation, mitochondrial dysfunction and other pathological events that are known to be the hallmarks of human PD[3,43,44]. While PLA2g6 was found to be important for endogenous SOCE in some cells including neurons[45,46], the molecular mechanism of this phenomenon, and its role in Parkinson's disease has been unknown. Based on the functional studies[46,47] PLA2g6 can be located between STIM1 ($Ca^{2+}$ sensor in ER membrane) and Orai1 ($Ca^{2+}$ channel in PM) in the SOCE signaling pathway, but the molecular mechanism of PLA2g6-dependent signal transduction remained a mystery, and the KO$^{Ex2}$ mice of this disclosure presented a new key for its resolution.

Molecular pull-down, co-IP and Proximity Ligation In Situ Assay (P-LISA) were used to identify molecular mechanism and requirements for interaction between PM-associated PLA2g6(L) and STIM1. FIG. 11a and FIG. 12 show that endogenous STIM1 (as well as overexpressed $^{YFP}$-STIM1) could be pulled down by a full length PLA2g6(L), but not by PLA2g6(L)$^{179-896}$, which lacks N terminus and mimics the product of PLA2g6 translation from cryptic ATG$_2$ (FIG. 6a, b). Moreover, it was found that the first 150aa of PLA2g6 are not only required, but also sufficient for STIM1 pull down (FIG. 11a). In addition, FIG. 11b (and FIG. 13) shows co-immunoprecipitation of endogenous STIM1 in a complex with endogenous PLA2g6(L), which further confirms their ability to interact. To test for interaction between endogenous PLA2g6(L) and STIM1 in individual cells, Proximity Ligation In Situ Assay (P-LISA)[48] was employed (see Methods and citation 48 for details). FIG. 11c shows images of MEFs from WT mice with red dots representing proximity ligation events in control and TG (10 μM)-treated WT cells. Quantitative analysis (FIG. 11c) revealed a 5 fold increase in the number of such events after TG treatment, suggesting that depletion of the stores promote co-localization and interaction of endogenous STIM1 and PLA2g6(L). Importantly, such interaction was severely impaired in MEFs from KO$^{Ex2}$ mice in which PLA2g6(L) lacks its N-terminus (FIG. 11c). Thus, N terminus of PLA2g6(L) (PLA2g6$^{1-150}$) appeared to be essential for store-dependent co-localization and molecular interaction of endogenous STIM1 with PLA2g6(L).

To determine the impact of the loss of N terminus of PLA2g6 on store-operated Ca$^{2+}$ signaling, and to identify which specific variant of PLA2g6 is involved, primary MEFs from WT and KO$^{Ex2}$ mice were used as a model cell system (FIG. 14). First, it was found that while deletion of N terminus did not affect catalytic activity of PLA2g6 (FIG. 6d), its activation by TG-induced store depletion in intact WT cells[31] was totally disrupted in KO$^{Ex2}$ MEFs (FIG. 14a). Second, endogenous SOCE appeared to be significantly impaired in KO$^{Ex2}$ MEFs (FIG. 14b, c, d): TPEN, known to mimic TG-induced ER depletion[31,49], activated S-BEL-sensitive Ca$^{2+}$ entry in MEFs from WT, but not KO$^{Ex2}$ mice. Thus, deletion of N-terminus of PLA2g6 prevented its activation by store depletion, and abolished PLA2g6-dependent SOCE in KO$^{Ex2}$ cells. To verify these important findings, rescue experiments were performed. FIG. 14e demonstrates that store depletion-induced activation of PLA2g6 in intact MEFs from KO$^{Ex2}$ mice could be fully restored by expression of the full length (L), but not (S) splice variant of PLA2g6. Expression of PLA2g6(L) also restored S-BEL-sensitive SOCE in KO$^{Ex2}$ cells (FIG. 14f, g), confirming its critical role for SOCE. Since one of the major physiological functions of SOCE is refilling of ER Ca$^{2+}$ stores, an analysis of how PLA2g6-dependent SOCE deficiency may affect intracellular Ca$^{2+}$ stores was performed. As predicted by the results presented herein, impairment of SOCE in the cells from KO$^{Ex2}$ mice resulted in constitutive depletion of intracellular Ca$^{2+}$ stores (FIG. 14h, i), as shown by a 60% decrease in the peak of Ca$^{2+}$ release caused by ionomycin in MEFs from KO$^{Ex2}$ mice compared to WT. Importantly, depletion of Ca$^{2+}$ stores in KO$^{Ex2}$ cells could be rescued by expression of a full length (L), but not (S) PLA2g6 (FIG. 14j, k). Thus, the data presented herein demonstrate that specific plasma membrane-associated (L), but not cytosolic (S) variant of PLA2g6 is required and directly involved in SOCE and ER Ca$^{2+}$ refilling. Impairment of signal transduction from STIM1 to PLA2g6(L) (by genetic truncation of N terminus of PLA2g6) results in depletion of intracellular Ca$^{2+}$ stores, which can be associated with PD-like phenotype in KO$^{Ex2}$ mice. It is important to emphasize that the same results are expected in the case of caspase 3-induced cleavage of the same N terminus of PLA2g6. Further, FIG. 14l,m,n shows that PLA2g6 carrying human PD-associated mutation (F72L) exhibits the same impairment of Ca$^{2+}$ signaling function as was found in KO$^{Ex2}$ mice. Indeed, expression of F72L mutant did not restore PLA2g6 activation by depleted stores (FIG. 14l), did not restore normal SOCE (FIG. 14m) and did not rescue ER Ca$^{2+}$ stores (FIG. 14n).

Thus, PD-associated genetic mutation(s) in PLA2g6, as well as truncation of its N terminus (genetically, or post-translational via caspase-3 dependent cleavage) results in impairment of SOCE and depletion of ER Ca$^{2+}$ stores, which can be a trigger and/or accelerator of age-dependent progressive death of dopaminergic neurons in substantia nigra, and can be a previously unknown cause of age-dependent PD.

C. Discussion

High vulnerability to Ca$^{2+}$ disturbance[50], low Ca$^{2+}$ buffering capacity and other factors can make DA neurons in SN particularly sensitive to dysfunction of Ca$^{2+}$ signaling. The late age-dependent onset of the PD-like phenotype in KO$^{Ex2}$ mice (resembling PD in ageing humans) indicates that age-dependent process(es) may participate in a final demise of DA neurons in KO$^{Ex2}$ mice. Oxidative stress, mitochondrial dysfunction, and/or protein misfolding are the hallmarks of a normal ageing process[51], and while they do not by themselves cause PD in ageing WT mice, they may become lethal for DA neurons weakened by sustained Ca$^{2+}$ store depletion and ER stress, as in the case of KO$^{Ex2}$ mice. The results reported herein support the idea that nigrostriatal degenerative process in a complex phenomenon[50,52,53] that involve newly discovered specific PARK14/PLA2g6-dependent Ca$^{2+}$ signaling mechanism that is located upstream from autophagic dysfunction, alpha synuclein aggregation, mitochondrial dysfunction, oxidative damage and protein degradation. The KO$^{Ex2}$ mouse model unmasked new targets and molecular interactions involved in store-operated Ca$^{2+}$ signaling, impairment of which can initiate, or in tandem with other processes exacerbate a sequence of pathological events leading to demise of DA neurons in SNpc and PD-like motor dysfunction.

Discovery of a causal relationship between impaired PARK14/PLA2g6-dependent SOCE, depletion of intracellular Ca$^{2+}$ stores, the loss of DA neurons in SN and development of PD-like phenotype in aging KO$^{Ex2}$ mice presents a novel molecular mechanism of PARK14 association with PD, and a new store-dependent Ca$^{2+}$ signaling axes that can be critically involved in familial, as well as age-dependent PD in humans. This is a starting point for unveiling mechanistically and clinically important relationships between PLA2g6-dependent Ca$^{2+}$ signaling and the processes involving other PARKs. The KO$^{Ex2}$ mouse model opens new unique opportunities for understanding the details of this complex process, and provides a powerful new tool for identification of methods and compositions for prevention and treatment of PD, a devastating neurodegenerative human disease that is waiting for its cure.

CITATIONS 1. de Lau, L. M. and Breteler, M. M. "Epidemiology of Parkinson's disease," *The Lancet Neurology* 5, 525 (2006).

2. Fahn, S. "Parkinson's disease: 10 years of progress, 1997-2007," *Mov Disord* 25, S2-S14 (2010).
3. Zimprich, A. "Genetics of Parkinson's disease and essential tremor," 24 (2011).
4. Paisan-Ruiz, C., et al. "Characterization of PLA2G6 as a locus for dystonia-parkinsonism," *Ann Neurol* 65, 19 (2009).
5. Sina, F., Shojaee, S., Elahi, E., and Paisan-Ruiz, C. "R632W mutation in PLA2G6 segregates with dystonia-parkinsonism in a consanguineous Iranian family," *Eur J Neurol* 16, 101 (2009).
6. Paisan-Ruiz, C., et al. "Early-onset L-dopa-responsive parkinsonism with pyramidal signs due to ATP13A2, PLA2G6, FBXO7 and spatacsin mutations," *Mov Disord* 25, 1791 (2010).
7. Yoshino, H., et al. "Phenotypic spectrum of patients with PLA2G6 mutation and PARK14-linked parkinsonism," *Neurology* 75, 1356 (2010).
8. Kauther, K. M., Hoft, C., Rissling, I., Oertel, W. H., and Moller, J. C. "The PLA2G6 gene in early-onset Parkinson's disease," *Mov Disord*,—n/a (2011).
9. Tomiyama, H., et al. "PLA2G6 variant in Parkinson's disease," *J Hum Genet* 56, 401 (2011).
10. Lu, C. S., et al. "PLA2G6 mutations in PARK14-linked young-onset parkinsonism and sporadic Parkinson's disease," *Am J Med Genet* 159B, 183 (2012).
11. Dennis, E. A., Cao, J., Hsu, Y. H., Magrioti, V., and Kokotos, G. "Phospholipase A2 enzymes: physical structure, biological function, disease implication, chemical inhibition, and therapeutic intervention," *Chem Rev* 111, 6130 (2011).
12. Albin, R. L., Young, A. B., and Penney, J. B. "The functional anatomy of disorders of the basal ganglia," *Trends in Neurosciences* 18, 63 (1995).
13. Morgan, N. V., et al. "PLA2G6, encoding a phospholipase A2, is mutated in neurodegenerative disorders with high brain iron," *Nat Genet* 38, 752 (2006).
14. Gregory, A., et al. "Neurodegeneration associated with genetic defects in phospholipase A(2)," *Neurology* 71, 1402 (2008).
15. Gregory, A., Polster, B. J., and Hayflick, S. J. "Clinical and genetic delineation of neurodegeneration with brain iron accumulation," *J Med Genet* 46, 73 (2009).
16. Paisan-Ruiz, C., et al. "Widespread Lewy body and tau accumulation in childhood and adult onset dystonia-parkinsonism cases with PLA2G6 mutations," *Neurobiol Aging* (2010).
17. Tonelli, A., et al. "Novel splice-site mutations and a large intragenic deletion in PLA2G6 associated with a severe and rapidly progressive form of infantile neuroaxonal dystrophy," *Clin Genet* 78, 432 (2010).
18. Engel, L. A., Jing, Z., O'Brien, D. E., Sun, M., and Kotzbauer, P. T. "Catalytic function of PLA2G6 is impaired by mutations associated with infantile neuroaxonal dystrophy but not dystonia-parkinsonism," *PLoS One* 5, e12897 (2010).
19. Schneider, S. A., Hardy, J., and Bhatia, K. P. "Syndromes of neurodegeneration with brain iron accumulation (NBIA): An update on clinical presentations, histological and genetic underpinnings, and treatment considerations," *Mov Disord*, n/a (2011).
20. Strokin, M., Seburn, K. L., Cox, G. A., Martens, K. A., and Reiser, G. "Severe disturbance in the Ca2+ signaling in astrocytes from mouse models of human infantile neuroaxonal dystrophy with mutated Pla2g6," 21, 2807 (2012).
21. Malik, I., et al. "Disrupted membrane homeostasis and accumulation of ubiquitinated proteins in a mouse model of infantile neuroaxonal dystrophy caused by PLA2G6 mutations," *Am J Pathol* 172, 406 (2008).
22. Shinzawa, K., et al. "Neuroaxonal dystrophy caused by group VIA phospholipase A2 deficiency in mice: a model of human neurodegenerative disease," *J Neurosci* 28, 2212 (2008).
23. Wada, H., et al. "Establishment of an improved mouse model for infantile neuroaxonal dystrophy that shows early disease onset and bears a point mutation in Pla2g6," *Am J Pathol* 175, 2257 (2009).
24. Beck, G., et al. "Neuroaxonal dystrophy in calcium-independent phospholipase A2beta deficiency results from insufficient remodeling and degeneration of mitochondrial and presynaptic membranes," *J Neurosci* 31, 11411 (2011).
25. Zhao, Z., et al. "Genetic Ablation of PLA2G6 in Mice Leads to Cerebellar Atrophy Characterized by Purkinje Cell Loss and Glial Cell Activation," 6, e26991 (2011).
26. Surmeier, D. J., Guzman, J. N., Sanchez-Padilla, J., and Schumacker, P. T. "The role of calcium and mitochondrial oxidant stress in the loss of substantia nigra pars compacta dopaminergic neurons in Parkinson's disease," 198, 221 (2011).
27. Surmeier, D. J., Guzman, J. N., and Sanchez-Padilla, J. "Calcium, cellular aging, and selective neuronal vulnerability in Parkinson's disease," 47, 175 (2010).
28. Surmeier, D. J. "A lethal convergence of dopamine and calcium," *Neuron* 62, 163 (2009).
29. Chan, C. S., Gertler, T. S., and Surmeier, D. J. "Calcium homeostasis, selective vulnerability and Parkinson's disease," *Trends Neurosci* 32, 249 (2009).
30. Smani, T., et al. "A novel mechanism for the store-operated calcium influx pathway," 6, 113 (2004).
31. Csutora, P., et al. "Activation mechanism for CRAC current and store-operated $Ca^{2+}$ entry: calcium influx factor and $Ca^{2+}$-independent phospholipase $A_2$b-mediated pathway.," *J Biol Chem* 281, 34926 (2006).
32. Jenkins, C. M., Han, X., Mancuso, D. J., and Gross, R. W. "Identification of Calcium-independent Phospholipase A2 (iPLA2) beta, and Not iPLA2gamma, as the Mediator of Arginine Vasopressin-induced Arachidonic Acid Release in A-10 Smooth Muscle Cells. Enantioselective mechanism-based discrimination of mammalian iPLA2s," *J Biol Chem* 277, 32807 (2002).
33. Bao, S., et al. "Male mice that do not express group VIA phospholipase A2 produce spermatozoa with impaired motility and have greatly reduced fertility," *J Biol Chem* 279, 38194 (2004).
34. Savitt, J. M., Dawson, V. L., and Dawson, T. M. "Diagnosis and treatment of Parkinson disease: molecules to medicine," 116, 1744 (2006).
35. Bolotina, V. M. "Orai, STIM1 and iPLA2beta: a view from a different perspective," 586, 3035 (2008).
36. Bolotina, V. M. "Microdomain Organization and the Role of Second Messengers. Store-Operated Ca Entry: Endogenous Messengers and Mediators," in *Store-Operated Calcium Entry (SOCE) Pathways*, edited by Groschner, K. (Springer-Verlag/Wien, 2012).
37. Putney, J. W. "Capacitative calcium entry: from concept to molecules," *Immunol Rev* 231, 10 (2009).
38. Parekh, A. B. "Store-operated CRAC channels: function in health and disease," *Nat Rev Drug Discov* 9, 399 (2010).
39. Putney, J. W. "The physiological function of store-operated calcium entry," *Neurochem Res* 36, 1157 (2011).

40. Berridge, M. J. "Neuronal calcium signaling," *Neuron* 21, 13 (1998).
41. Putney, J. W., Jr. "Capacitative calcium entry in the nervous system," 34, 339 (2003).
42. Bollimuntha, S., Pani, B., and Singh, B. B. "Pathophysiological Perspective of Neuronal Store-Operated Ca2+ Signaling. Store-Operated Calcium Entry Pathways," in edited by Groschner, K. and Romanin, C. (Springer Heidelberg, 2012), pp. 417-434.
43. Cali, T., Ottolini, D., and Brini, M. "Mitochondria, calcium, and endoplasmic reticulum stress in Parkinson's disease," 37, 228 (2011).
44. Selvaraj, S., et al. "Neurotoxin-induced ER stress in mouse dopaminergic neurons involves downregulation of TRPC1 and inhibition of AKT/mTOR signaling," *J Clin Invest* 122, 1354 (2012).
45. Singaravelu, K., Lohr, C., and Deitmer, J. W. "Calcium-independent phospholipase A2 mediates store-operated calcium entry in rat cerebellar granule cells," *Cerebellum* 7, 467 (2008).
46. Csutora, P., et al. "Novel Role for STIM1 as a Trigger for Calcium Influx Factor Production," *J Biol Chem* 283, 14524 (2008).
47. Gwozdz, T., Dutko-Gwozdz, J., Zarayskiy, V., Peter, K., and Bolotina, V. M. "How strict is the correlation between STIM1 and Orai1 expression, puncta formation, and ICRAC activation?," 295, C1133-C1140 (2008).
48. Soderberg, O., et al. "Direct observation of individual endogenous protein complexes in situ by proximity ligation," *Nat Methods* 3, 995 (2006).
49. Hofer, A. M., Fasolato, C., and Pozzan, T. "Capacitative $Ca^{2+}$ entry is closely linked to the filling state of internal $Ca^{2+}$ stores: A study using simultaneous measurements of $I_{crac}$ and intraluminal $[Ca^{2+}]$," *J Cell Biol* 140, 325 (1998).
50. Surmeier, D. J., Guzman, J. N., Sanchez, J., and Schumacker, P. T. "Physiological phenotype and vulnerability in Parkinson's disease," *Cold Spring Harb Perspect Med* 2, a009290 (2012).
51. Collier, T. J., Kanaan, N. M., and Kordower, J. H. "Ageing as a primary risk factor for Parkinson's disease: evidence from studies of non-human primates," *Nat Rev Neurosci* 12, 359 (2011).
52. Dehay, B. and Bezard, E. "New animal models of Parkinson's disease," *Mov Disord* 26, 1198 (2011).
53. Chesselet, M. F. and Richter, F. "Modelling of Parkinson's disease in mice," *The Lancet Neurology* 10, 1108 (2011).
54. Brooks, S. P. and Dunnett, S. B. "Tests to assess motor phenotype in mice: a user's guide," *Nat Rev Neurosci* 10, 519 (2009).
55. Chen, P. C., et al. "Ubiquitin homeostasis is critical for synaptic development and function," *J Neurosci* 31, 17505 (2011).
56. Csutora, P., et al. "Activation mechanism for CRAC current and store-operated Ca2+ entry: calcium influx factor and Ca2+-independent phospholipase A2b-mediated pathway.," *J Biol Chem* 281, 34926 (2006).
57. Gwozdz, T., Dutko-Gwozdz, J., Schafer, C., and Bolotina, V. M. "Overexpression of Orai1 and STIM1 Proteins Alters Regulation of Store-operated Ca2+ Entry by Endogenous Mediators," *J Biol Chem* 287, 22865 (2012).
58. Jackson-Lewis, V. and Przedborski, S. "Protocol for the MPTP mouse model of Parkinson's disease," *Nat Protocols* 2, 141 (2007).
59. Larsson Forsell, P. K. A., Kennedy, B. P., and Claesson, H. E. "The human calcium-independent phospholipase A2 gene: Multiple enzymes with distinct properties from a single gene," *Eur J Biochem* 262, 575 (1999).
60. Larsson, P. K., Claesson, H. E., and Kennedy, B. P. "Multiple splice variants of the human calcium-independent phospholipase A2 and their effect on enzyme activity," *J Biol Chem* 273, 207 (1998).
61. Nakakuki, T., et al. "Ligand-specific c-Fos expression emerges from the spatiotemporal control of ErbB network dynamics," 141, 884 (2010)
62. Reinhardt, C., et al. "Tissue factor and PAR1 promote microbiota-induced intestinal vascular remodelling," *Nature* 483, 627 (2012).
63. Smani, T., et al. "A novel mechanism for the store-operated calcium influx pathway," 6, 113 (2004).
64. Soderberg, O., et al. "Direct observation of individual endogenous protein complexes in situ by proximity ligation," *Nat Methods* 3, 995 (2006).

What is claimed is:

1. A method of maintaining or restoring normal store-operated $Ca^{2+}$ entry (SOCE) function and ER $Ca^{2+}$ stores in a mammalian cell, comprising expressing a sufficient amount of a functional caspase-3 cleavage-resistant PLA2g6 protein in the cell to thereby maintain or restore normal store-operated $Ca^{2+}$ entry (SOCE) function and ER $Ca^{2+}$ stores in the mammalian cell;
    wherein the functional caspase-3 cleavage-resistant PLA2g6 protein has an amino acid sequence at least 99% identical to SEQ ID NO: 1; and
    wherein the functional caspase-3 cleavage-resistant PLA2g6 protein comprises a deletion or substitution of the aspartic acid residue at the amino acid position corresponding to amino acid position D183 of SEQ ID NO: 1.

2. The method of claim 1, wherein the amino acid sequence of the functional caspase-3 cleavage-resistant PLA2g6 protein is 100% identical to SEQ ID NO: 1 except for a deletion or substitution of the aspartic acid residue at the amino acid position corresponding to amino acid position D183 of SEQ ID NO: 1.

3. The method of claim 1, wherein the mammalian cell is a human cell.

4. The method of claim 1, wherein the mammalian cell is a mouse cell.

5. The method of claim 1, wherein the functional caspase-3 cleavage-resistant PLA2g6 protein is expressed in the mammalian cell by introduction of a nucleic acid encoding the functional caspase-3 cleavage-resistant PLA2g6 protein into the cell.

6. The method of claim 1, wherein the mammalian cell is cultured in vitro.

7. The method of claim 6, wherein the mammalian cell is a neuron.

8. The method of claim 1, wherein the mammalian cell is an in vivo cell.

9. A method of treating or preventing Parkinson's disease (PD)-related deficit(s) in a mammal, comprising expressing a sufficient amount of a functional caspase-3 cleavage-resistant PLA2g6 protein in neurons of the mammal to thereby treat or prevent Parkinson's disease (PD)-related deficit(s) in the mammal;
    wherein the functional caspase-3 cleavage-resistant PLA2g6 protein has an amino acid sequence at least 99% identical to SEQ ID NO: 1; and
    wherein the functional caspase-3 cleavage-resistant PLA2g6 protein comprises a deletion or substitution of the aspartic acid residue at the amino acid position corresponding to amino acid position D183 of SEQ ID NO: 1.

10. The method of claim 9, wherein the amino acid sequence of the functional caspase-3 cleavage-resistant PLA2g6 protein is 100% identical to SEQ ID NO: 1 except for a deletion or substitution of the aspartic acid residue at the amino acid position corresponding to amino acid position D183 of SEQ ID NO: 1.

11. The method of claim 9, wherein the mammal is a human.

12. The method of claim 9, wherein the mammal is a mouse.

13. The method of claim 9, wherein the functional caspase-3 cleavage-resistant PLA2g6 protein is expressed in the neurons by introduction of a nucleic acid encoding the functional caspase-3 cleavage-resistant PLA2g6 protein into the neurons.

* * * * *

SEQUENCE LISTING

<160> NUMBER OF SEQ ID NOS: 16

<210> SEQ ID NO 1
<211> LENGTH: 806
<212> TYPE: PRT
<213> ORGANISM: Homo sapiens

<400> SEQUENCE: 1

Met Gln Phe Phe Gly Arg Leu Val Asn Thr Phe Ser Gly Val Thr Asn
1               5                   10                  15

Leu Phe Ser Asn Pro Phe Arg Val Lys Glu Val Ala Val Ala Asp Tyr
            20                  25                  30

Thr Ser Ser Asp Arg Val Arg Glu Gly Gln Leu Ile Leu Phe Gln
        35                  40                  45

Asn Thr Pro Asn Arg Thr Trp Asp Cys Val Leu Val Asn Pro Arg Asn
    50                  55                  60

Ser Gln Ser Gly Phe Arg Leu Phe Gln Leu Glu Leu Glu Ala Asp Ala
65                  70                  75                  80

Leu Val Asn Phe His Gln Tyr Ser Ser Gln Leu Leu Pro Phe Tyr Glu

```
              85                  90                  95
Ser Ser Pro Gln Val Leu His Thr Glu Val Leu Gln His Leu Thr Asp
            100                 105                 110

Leu Ile Arg Asn His Pro Ser Trp Ser Val Ala His Leu Ala Val Glu
            115                 120                 125

Leu Gly Ile Arg Glu Cys Phe His His Ser Arg Ile Ile Ser Cys Ala
            130                 135                 140

Asn Cys Ala Glu Asn Glu Glu Gly Cys Thr Pro Leu His Leu Ala Cys
145                 150                 155                 160

Arg Lys Gly Asp Gly Glu Ile Leu Val Glu Leu Val Gln Tyr Cys His
                165                 170                 175

Thr Gln Met Asp Val Thr Asp Tyr Lys Gly Glu Thr Val Phe His Tyr
            180                 185                 190

Ala Val Gln Gly Asp Asn Ser Gln Val Leu Gln Leu Leu Gly Arg Asn
            195                 200                 205

Ala Val Ala Gly Leu Asn Gln Val Asn Asn Gln Gly Leu Thr Pro Leu
            210                 215                 220

His Leu Ala Cys Gln Leu Gly Lys Gln Glu Met Val Arg Val Leu Leu
225                 230                 235                 240

Leu Cys Asn Ala Arg Cys Asn Ile Met Gly Pro Asn Gly Tyr Pro Ile
                245                 250                 255

His Ser Ala Met Lys Phe Ser Gln Lys Gly Cys Ala Glu Met Ile Ile
            260                 265                 270

Ser Met Asp Ser Ser Gln Ile His Ser Lys Asp Pro Arg Tyr Gly Ala
            275                 280                 285

Ser Pro Leu His Trp Ala Lys Asn Ala Glu Met Ala Arg Met Leu Leu
            290                 295                 300

Lys Arg Gly Cys Asn Val Asn Ser Thr Ser Ala Gly Asn Thr Ala
305                 310                 315                 320

Leu His Val Ala Val Met Arg Asn Arg Phe Asp Cys Ala Ile Val Leu
                325                 330                 335

Leu Thr His Gly Ala Asn Ala Asp Ala Arg Gly Glu His Gly Asn Thr
            340                 345                 350

Pro Leu His Leu Ala Met Ser Lys Asp Asn Val Glu Met Ile Lys Ala
            355                 360                 365

Leu Ile Val Phe Gly Ala Glu Val Asp Thr Pro Asn Asp Phe Gly Glu
            370                 375                 380

Thr Pro Thr Phe Leu Ala Ser Lys Ile Gly Arg Leu Val Thr Arg Lys
385                 390                 395                 400

Ala Ile Leu Thr Leu Leu Arg Thr Val Gly Ala Glu Tyr Cys Phe Pro
                405                 410                 415

Pro Ile His Gly Val Pro Ala Glu Gln Gly Ser Ala Ala Pro His His
            420                 425                 430

Pro Phe Ser Leu Glu Arg Ala Gln Pro Pro Ile Ser Leu Asn Asn
            435                 440                 445

Leu Glu Leu Gln Asp Leu Met His Ile Ser Arg Ala Arg Lys Pro Ala
            450                 455                 460

Phe Ile Leu Gly Ser Met Arg Asp Glu Lys Arg Thr His Asp His Leu
465                 470                 475                 480

Leu Cys Leu Asp Gly Gly Val Lys Gly Leu Ile Ile Gln Leu
                485                 490                 495

Leu Ile Ala Ile Glu Lys Ala Ser Gly Val Ala Thr Lys Asp Leu Phe
            500                 505                 510
```

Asp Trp Val Ala Gly Thr Ser Thr Gly Gly Ile Leu Ala Leu Ala Ile
            515                 520                 525

Leu His Ser Lys Ser Met Ala Tyr Met Arg Gly Met Tyr Phe Arg Met
        530                 535                 540

Lys Asp Glu Val Phe Arg Gly Ser Arg Pro Tyr Glu Ser Gly Pro Leu
545                 550                 555                 560

Glu Glu Phe Leu Lys Arg Glu Phe Gly Glu His Thr Lys Met Thr Asp
                565                 570                 575

Val Arg Lys Pro Lys Val Met Leu Thr Gly Thr Leu Ser Asp Arg Gln
            580                 585                 590

Pro Ala Glu Leu His Leu Phe Arg Asn Tyr Asp Ala Pro Glu Thr Val
        595                 600                 605

Arg Glu Pro Arg Phe Asn Gln Asn Val Asn Leu Arg Pro Pro Ala Gln
    610                 615                 620

Pro Ser Asp Gln Leu Val Trp Arg Ala Ala Arg Ser Ser Gly Ala Ala
625                 630                 635                 640

Pro Thr Tyr Phe Arg Pro Asn Gly Arg Phe Leu Asp Gly Gly Leu Leu
                645                 650                 655

Ala Asn Asn Pro Thr Leu Asp Ala Met Thr Glu Ile His Glu Tyr Asn
            660                 665                 670

Gln Asp Leu Ile Arg Lys Gly Gln Ala Asn Lys Val Lys Lys Leu Ser
        675                 680                 685

Ile Val Val Ser Leu Gly Thr Gly Arg Ser Pro Gln Val Pro Val Thr
    690                 695                 700

Cys Val Asp Val Phe Arg Pro Ser Asn Pro Trp Glu Leu Ala Lys Thr
705                 710                 715                 720

Val Phe Gly Ala Lys Glu Leu Gly Lys Met Val Val Asp Cys Cys Thr
                725                 730                 735

Asp Pro Asp Gly Arg Ala Val Asp Arg Ala Arg Ala Trp Cys Glu Met
            740                 745                 750

Val Gly Ile Gln Tyr Phe Arg Leu Asn Pro Gln Leu Gly Thr Asp Ile
        755                 760                 765

Met Leu Asp Glu Val Ser Asp Thr Val Leu Val Asn Ala Leu Trp Glu
    770                 775                 780

Thr Glu Val Tyr Ile Tyr Glu His Arg Glu Glu Phe Gln Lys Leu Ile
785                 790                 795                 800

Gln Leu Leu Leu Ser Pro
                805

<210> SEQ ID NO 2
<211> LENGTH: 807
<212> TYPE: PRT
<213> ORGANISM: Mus musculus

<400> SEQUENCE: 2

Met Gln Phe Phe Gly Arg Leu Val Asn Thr Leu Ser Ser Val Thr Asn
1               5                   10                  15

Leu Phe Ser Asn Pro Phe Arg Val Lys Glu Val Ser Leu Thr Asp Tyr
            20                  25                  30

Val Ser Glu Arg Val Arg Glu Gly Gln Leu Ile Leu Leu Gln
        35                  40                  45

Asn Val Ser Asn Arg Thr Trp Asp Cys Val Leu Val Ser Pro Arg Asn
    50                  55                  60

Pro Gln Ser Gly Phe Arg Leu Phe Gln Leu Glu Ser Glu Ala Asp Ala

-continued

```
                65                  70                  75                  80
Leu Val Asn Phe Gln Gln Phe Ser Ser Gln Leu Pro Pro Phe Tyr Glu
                    85                  90                  95

Ser Ser Val Gln Val Leu His Val Glu Val Leu Gln His Leu Thr Asp
                100                 105                 110

Leu Ile Arg Asn His Pro Ser Trp Thr Val Thr His Leu Ala Val Glu
                115                 120                 125

Leu Gly Ile Arg Glu Cys Phe His His Ser Arg Ile Ile Ser Cys Ala
                130                 135                 140

Asn Ser Thr Glu Asn Glu Glu Gly Cys Thr Pro Leu His Leu Ala Cys
145                 150                 155                 160

Arg Lys Gly Asp Ser Glu Ile Leu Val Glu Leu Val Gln Tyr Cys His
                165                 170                 175

Ala Gln Met Asp Val Thr Asp Asn Lys Gly Glu Thr Ala Phe His Tyr
                180                 185                 190

Ala Val Gln Gly Asp Asn Pro Gln Val Leu Gln Leu Leu Gly Lys Asn
                195                 200                 205

Ala Ser Ala Gly Leu Asn Gln Val Asn Asn Gln Gly Leu Thr Pro Leu
                210                 215                 220

His Leu Ala Cys Lys Met Gly Lys Gln Glu Met Val Arg Val Leu Leu
225                 230                 235                 240

Leu Cys Asn Ala Arg Cys Asn Ile Met Gly Pro Gly Gly Phe Pro Ile
                245                 250                 255

His Thr Ala Met Lys Phe Ser Gln Lys Gly Cys Ala Glu Met Ile Ile
                260                 265                 270

Ser Met Asp Ser Asn Gln Ile His Ser Lys Asp Pro Arg Tyr Gly Ala
                275                 280                 285

Ser Pro Leu His Trp Ala Lys Asn Ala Glu Met Ala Arg Met Leu Leu
                290                 295                 300

Lys Arg Gly Cys Asp Val Asp Ser Thr Ser Ser Ser Gly Asn Thr Ala
305                 310                 315                 320

Leu His Val Ala Val Met Arg Asn Arg Phe Asp Cys Val Met Val Leu
                325                 330                 335

Leu Thr Tyr Gly Ala Asn Ala Gly Ala Arg Gly Glu His Gly Asn Thr
                340                 345                 350

Pro Leu His Leu Ala Met Ser Lys Asp Asn Met Glu Met Val Lys Ala
                355                 360                 365

Leu Ile Val Phe Gly Ala Glu Val Asp Thr Pro Asn Asp Phe Gly Glu
                370                 375                 380

Thr Pro Ala Leu Ile Ala Ser Lys Ile Ser Lys Leu Ile Thr Arg Lys
385                 390                 395                 400

Ala Leu Leu Thr Leu Leu Lys Thr Val Gly Ala Asp His His Phe Pro
                405                 410                 415

Ile Ile Gln Gly Val Ser Thr Glu Gln Gly Ser Ala Ala Thr His
                420                 425                 430

Pro Leu Phe Ser Leu Asp Arg Thr Gln Pro Pro Ala Ile Ser Leu Asn
                435                 440                 445

Asn Leu Glu Leu Gln Asp Leu Met Pro Ile Ser Arg Ala Arg Lys Pro
                450                 455                 460

Ala Phe Ile Leu Ser Ser Met Arg Asp Glu Lys Arg Ser His Asp His
465                 470                 475                 480

Leu Leu Cys Leu Asp Gly Gly Gly Val Lys Gly Leu Val Ile Ile Gln
                485                 490                 495
```

```
Leu Leu Ile Ala Ile Glu Lys Ala Ser Gly Val Ala Thr Lys Asp Leu
                500                 505                 510

Phe Asp Trp Val Ala Gly Thr Ser Thr Gly Gly Ile Leu Ala Leu Ala
            515                 520                 525

Ile Leu His Ser Lys Ser Met Ala Tyr Met Arg Gly Val Tyr Phe Arg
        530                 535                 540

Met Lys Asp Glu Val Phe Arg Gly Ser Arg Pro Tyr Glu Ser Gly Pro
545                 550                 555                 560

Leu Glu Glu Phe Leu Lys Arg Glu Phe Gly Glu His Thr Lys Met Thr
                565                 570                 575

Asp Val Lys Lys Pro Lys Val Met Leu Thr Gly Thr Leu Ser Asp Arg
            580                 585                 590

Gln Pro Ala Glu Leu His Leu Phe Arg Asn Tyr Asp Ala Pro Glu Ala
        595                 600                 605

Val Arg Glu Pro Arg Cys Asn Gln Asn Ile Asn Leu Lys Pro Pro Thr
610                 615                 620

Gln Pro Ala Asp Gln Leu Val Trp Arg Ala Ala Arg Ser Ser Gly Ala
625                 630                 635                 640

Ala Pro Thr Tyr Phe Arg Pro Asn Gly Arg Phe Leu Asp Gly Gly Leu
                645                 650                 655

Leu Ala Asn Asn Pro Thr Leu Asp Ala Met Thr Glu Ile His Glu Tyr
            660                 665                 670

Asn Gln Asp Met Ile Arg Lys Gly Gln Gly Asn Lys Val Lys Lys Leu
        675                 680                 685

Ser Ile Val Val Ser Leu Gly Thr Gly Lys Ser Pro Gln Val Pro Val
        690                 695                 700

Thr Cys Val Asp Val Phe Arg Pro Ser Asn Pro Trp Glu Leu Ala Lys
705                 710                 715                 720

Thr Val Phe Gly Ala Lys Glu Leu Gly Lys Met Val Val Asp Cys Cys
                725                 730                 735

Thr Asp Pro Asp Gly Arg Ala Val Asp Arg Ala Arg Ala Trp Cys Glu
            740                 745                 750

Met Val Gly Ile Gln Tyr Phe Arg Leu Asn Pro Gln Leu Gly Ser Asp
        755                 760                 765

Ile Met Leu Asp Glu Val Ser Asp Ala Val Leu Val Asn Ala Leu Trp
770                 775                 780

Glu Thr Glu Val Tyr Ile Tyr Glu His Arg Glu Glu Phe Gln Lys Leu
785                 790                 795                 800

Val Gln Leu Leu Leu Ser Pro
                805

<210> SEQ ID NO 3
<211> LENGTH: 23
<212> TYPE: PRT
<213> ORGANISM: Mus musculus

<400> SEQUENCE: 3

Cys Ser Thr Glu Gln Gly Ser Ala Ala Ala Thr His Pro Leu Phe Ser
1               5                   10                  15

Leu Asp Arg Thr Gln Pro Pro
            20

<210> SEQ ID NO 4
<211> LENGTH: 31
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 4
aatttagata tcatgcagtt ctttggccgc c                                      31

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aatttagata tcatggatgt caccgactac aaggg                                  35

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aataaggaat tcgggtgaga gcagcaggtg g                                      31

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aatatcgaat tcctcgttct ccgcgcaatt g                                      31

<210> SEQ ID NO 8
<211> LENGTH: 164
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
gctagcgtta acaccggtat ggaattcgaa caaaaactca tctcagaaga ggatctggat       60
atccctgcag gctaaggatc ccacgtgctc gagcgtctcc aattggcggc cgcaagagga      120
tcgcatcacc atcaccatca ctagagtgaa gcttaagttt aaac                       164

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aatttacgtc tcctagttgt ctgccgattt tggaggctag                             40
```

```
<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aatttacgtc tcaactacaa gacttgatgc atataagtcg                           40

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtgaacacac aggctaaggc tccaatcta                                       29

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tcaacaagca aaggacagac atcccac                                         27

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agcagagggg caggctgggt ctctc                                           25

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aggaacacag ttgttgggct ggggttgtc                                       29

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tatcttctcg agttctctag cctccaatcc tggg                                 34

<210> SEQ ID NO 16
```

```
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cacatagaat tcgtcccctt gcacagcgta atgg                              34
```